United States Patent
Zhou et al.

(10) Patent No.: US 9,415,047 B2
(45) Date of Patent: Aug. 16, 2016

(54) USE OF BENZO FIVE-MEMBERED NITROGEN HETEROCYCLIC PIPERAZINE OR PIPERIDINE DERIVATIVES

(71) Applicants: Liaoning Emmy Biological Pharmaceutical Co., Ltd., Liaoning (CN); Shenyang Emmy Pharmaceutical Research Institute Co., Ltd., Liaoning (CN)

(72) Inventors: Yan Zhou, Liaoning (CN); Lirong Zhang, Liaoning (CN); Jie Zhou, Liaoning (CN); Xin Zhou, Liaoning (CN)

(73) Assignees: Liaoning Emmy Biological Pharmaceutical Co., Ltd., Liaoning (CN); Shenyang Emmy Pharmaceutical Research Institute Co., Ltd., Liaoning (CN)

(*) Notice: Subject to any disclaimer, the term of this patent is extended or adjusted under 35 U.S.C. 154(b) by 0 days.

(21) Appl. No.: 14/647,408

(22) PCT Filed: Nov. 25, 2013

(86) PCT No.: PCT/CN2013/001442
§ 371 (c)(1),
(2) Date: May 26, 2015

(87) PCT Pub. No.: WO2014/079155
PCT Pub. Date: May 30, 2014

(65) Prior Publication Data
US 2015/0297586 A1    Oct. 22, 2015

(30) Foreign Application Priority Data

Nov. 26, 2012  (CN) .......................... 2012 1 0486619
Nov. 26, 2012  (CN) .......................... 2012 1 0486967
Nov. 26, 2012  (CN) .......................... 2012 1 0487128

(51) Int. Cl.
*A61K 31/496*  (2006.01)
*A61K 31/454*  (2006.01)
(Continued)

(52) U.S. Cl.
CPC ............. *A61K 31/496* (2013.01); *A61K 31/454* (2013.01); *A61K 31/4545* (2013.01);
(Continued)

(58) Field of Classification Search
CPC .............. A61K 31/496; A61K 31/454; A61K 31/4545; A61K 31/506; C07D 209/08; C07D 231/56; C07D 235/08; C07D 235/14; C07D 235/22; C07D 401/06; C07D 401/12
USPC ............................................. 514/252.13, 254
See application file for complete search history.

(56) References Cited

U.S. PATENT DOCUMENTS 3,362,956 A * 1/1968 Archer ................. C07D 209/60
                                                         544/225
3,472,854 A * 10/1969 Archer ................. C07D 209/60
                                                         514/906
(Continued)

FOREIGN PATENT DOCUMENTS

CN      1154693 A     7/1997
CN      1944404 A     4/2007
CN    101759693 A     6/2010

OTHER PUBLICATIONS

Alessandro Boido et al., "Synthesis and pharmacological evaluation of aryl/heteroaryl piperazinyl alkyl benzotriazoles as ligands for some serotonin and dopamine receptor subtypes," IL FARMACO, 2001, vol. 56, pp. 263-275.*

(Continued)

*Primary Examiner* — Kamal Saeed
*Assistant Examiner* — Janet L Coppins
(74) *Attorney, Agent, or Firm* — Hultquist, PLLC; Steven J. Hultquist

(57) ABSTRACT

This invention relates to the use of a compound in formula (I) and its salts acceptable pharmaceutically in preparation of vasodilative drugs:

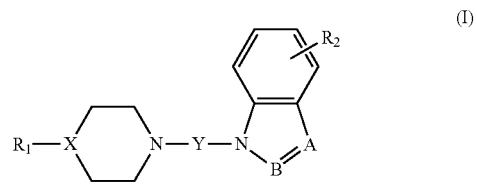

Wherein, $R_1$, $R_2$, X, Y, A and B are defined in the invention.

19 Claims, 11 Drawing Sheets

(51) Int. Cl.

| | |
|---|---|
| A61K 31/498 | (2006.01) |
| C07D 209/08 | (2006.01) |
| C07D 231/56 | (2006.01) |
| C07D 403/12 | (2006.01) |
| C07D 401/14 | (2006.01) |
| C07D 405/14 | (2006.01) |
| C07D 413/14 | (2006.01) |
| A61K 31/4545 | (2006.01) |
| C07D 235/08 | (2006.01) |
| C07D 401/06 | (2006.01) |
| C07D 401/12 | (2006.01) |
| C07D 405/12 | (2006.01) |
| C07D 413/12 | (2006.01) |
| C07D 417/12 | (2006.01) |
| C07D 417/14 | (2006.01) |
| C07D 249/18 | (2006.01) |
| A61K 31/506 | (2006.01) |
| C07D 235/10 | (2006.01) |
| C07D 235/14 | (2006.01) |
| C07D 235/22 | (2006.01) |
| A61K 45/06 | (2006.01) |

(52) U.S. Cl.
CPC .............. *A61K31/498* (2013.01); *A61K 31/506* (2013.01); *A61K 45/06* (2013.01); *C07D 209/08* (2013.01); *C07D 231/56* (2013.01); *C07D 235/08* (2013.01); *C07D 235/10* (2013.01); *C07D 235/14* (2013.01); *C07D 235/22* (2013.01); *C07D 249/18* (2013.01); *C07D 401/06* (2013.01); *C07D 401/12* (2013.01); *C07D 401/14* (2013.01); *C07D 403/12* (2013.01); *C07D 405/12* (2013.01); *C07D 405/14* (2013.01); *C07D 413/12* (2013.01); *C07D 413/14* (2013.01); *C07D 417/12* (2013.01); *C07D 417/14* (2013.01)

(56) References Cited

U.S. PATENT DOCUMENTS

2010/0329978 A1  12/2010  McCurdy et al.
2011/0306638 A1  12/2011  Li et al.

OTHER PUBLICATIONS

PubMed abstract of Dabire et al, "Central 5-hydroxytyptamine (5-HT) receptors in blood pressure regulation," Therapie, 1991, vol. 46(6), pp. 421-429.*

Boido, A., et al., "Synthesis and pharmacological evaluation of aryl/heteroaryl piperazinyl alkyl benzotriazoles as ligands for some serotonin and dopamine receptor subtypes", "IL Farmaco", Apr. 2001, pp. 263-275, vol. 56.

Boido, A., et al., "Alpha1- and alpha2-adrenoreceptor antagonist profiles of 1- and 2-[omega-(4-arylpiperazin-1-yl)alkyl]-1,2,3-benzotriazoles", "Chemistry & Biodiversity", Oct. 2005, pp. 1290-1304, vol. 2.

Caliendo, G., et al., "Synthesis and biological activity of benzotriazole derivatives structurally related to trazodone", "European Journal of Medicinal Chemistry", Jan. 1, 1995, pp. 77-84, vol. 30.

Caliendo, G., et al., "Structureaffinity relationship studies on benzotriazole derivatives binding to 5-HT receptor subtypes", "European Journal of Medicinal Chemistry", 1996, pp. 207-213, vol. 31.

Hoyer, D., et al., "International Union of Pharmacology classification of receptors for 5-hydroxytryptamine (Serotonin)", "Pharmacological Reviews", Jun. 1994, pp. 157-203, vol. 46, No. 2.

Mesangeau, C., et al., "Synthesis and pharmacological evaluation of indole-based sigma receptor ligands", "European Journal of Medicinal Chemistry", Aug. 29, 2011, pp. 5154-5161, vol. 46.

Mokrosz, M., et al., "Structure-activity relationship studies of CNS agents, Part 32: Effect of structural modifications in 1-arylpiperazine derivatives on alpha(1) -adrenoreceptor affinity", "Arch. Pharm. (Weinheim).", Jun. 1997, pp. 177-180, vol. 330.

Co-pending Unpublished U.S. Appl. No. 14/647,378, filed May 25, 2015.

* cited by examiner

USE OF BENZO FIVE-MEMBERED NITROGEN HETEROCYCLIC PIPERAZINE OR PIPERIDINE DERIVATIVES

CROSS-REFERENCE TO RELATED APPLICATIONS

This application is a U.S. national phase under the provisions of 35 U.S.C. §371 of International Patent Application No. PCT/CN13/01442 filed Nov. 25, 2013, which in turn claims priority of Chinese Patent Application No. 201210487128.6 filed Nov. 26, 2012, Chinese Patent Application No. 201210486967.6 filed Nov. 26, 2012, and Chinese Patent Application No. 201210486619.9 filed Nov. 26, 2012. The disclosures of such international patent application and Chinese priority patent applications are hereby incorporated herein by reference in their respective entireties, for all purposes.

FIELD OF THE INVENTION

The present invention relates to use of benzo five-membered nitrogen heterocyclic piperazine or piperidine derivatives in preparation of vasodilative drugs.

BACKGROUND OF THE INVENTION

Currently there are various categories of vasodilative drugs available in clinical field, e.g., $\alpha_1$ receptor blockers, including furazosin, doxazosin and terazosin, etc., which have obvious first dose effects or orthostatic hypotension, so their extensive application is limited in clinical practice. $Ca^{2+}$ channel blockers, including amlodipine, nifedipine and felodipine, etc. currently, which are still extensively applied in clinical practice, but also with risks of heart suppression.

Therefore, it is still necessary to develop new vasodilative drugs, improve efficacy, reduce drug resistance or minimize drug toxicity, to satisfy clinical demands of different patients.

CONTENTS OF THE INVENTION

This invention offers the use of a compound in formula (I) and its salts acceptable pharmaceutically in preparation of vasodilative drugs:

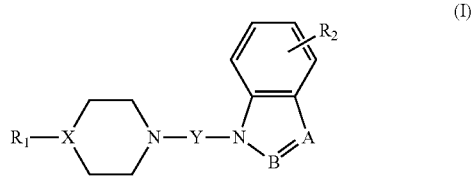

(I)

Wherein, $R_1$ indicates aromatic groups or alicyclic groups with mono or polysubstituted by $R_3$, wherein, $R_3$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms. If $R_3$ indicates polysubstituted group, $R_3$ is independently chosen from halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), alkyl parts in the above said groups are substituted by anyone or more halogen atoms.

A, B and X respectively indicate CH or N.

$R_2$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms. If $R_2$ indicates polysubstituted group, $R_2$ is independently chosen from halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), alkyl parts in the above said groups are substituted by anyone or more halogen atoms.

Y indicates saturated or unsaturated straight or branched hydrocarbon chain composed of 1-8 carbon atoms substituted by anyone or more halogen atoms, in which anyone or more carbon atoms are substituted by hetero atoms such as oxygen, sulfur or nitrogen.

ILLUSTRATION BY ACCOMPANYING FIGURES

SPECIFIC OPERATING PROCEDURE

Figure 1:
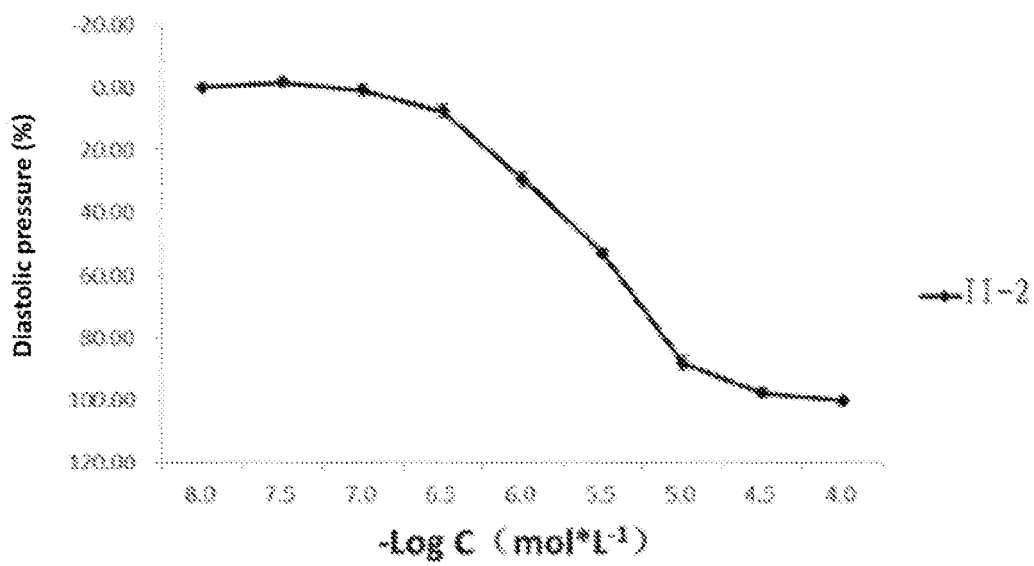
FIG. 1 illustrates the accumulated concentration effect curve of vasodilative effects of compound II-2 ($10^{-8}$-$10^{-4}$ mol·$L^{-1}$) versus vasoconstrictive effects of adrenaline ($10^{-5}$ mol·$L^{-1}$) on excised blood vessels from rabbits.

This invention offers the use of a compound in formula (I) and its salts acceptable pharmaceutically in preparation of vasodilative drugs:

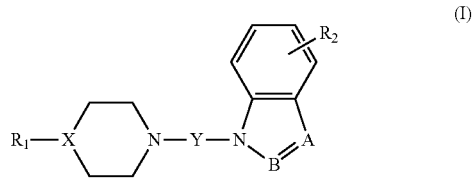

Wherein, $R_1$ indicates aromatic groups or alicyclic groups with mono or polysubstituted by $R_3$, wherein, $R_3$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, NO$_2$, NH$_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms. If $R_3$ indicates polysubstituted group, $R_3$ is independently chosen from halogen, CN, $C_1$-$C_6$ alkyl, $C_1$-$C_6$ alkoxyl, CHO, CO($C_1$-$C_6$ alkyl), COO($C_1$-$C_6$ alkyl), COOH, NO$_2$, NH$_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$ ($C_1$-$C_6$ alkyl), alkyl parts in the above said groups are substituted by anyone or more halogen atoms.

A, B and X respectively indicate CH or N.

$R_2$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, NO$_2$, NH$_2$, NH($C_1$-$C_6$ alkyl), N($C_1$-$C_6$ alkyl)$_2$, SH, S($C_1$-$C_6$ alkyl), —S(O) ($C_1$-$C_6$ alkyl) or —S(O)$_2$($C_1$-$C_6$ alkyl), alkyl parts in the above said groups are substituted by anyone or more halogen atoms. If $R_2$ indicates polysubstituted group, $R_2$ is independently chosen from halogen, CN, $C_1$-$C_6$ alkyl, $C_1$-$C_6$ alkoxyl, CHO, CO($C_1$-$C_6$ alkyl), COO($C_1$-$C_6$ alkyl), COOH, NO$_2$, NH$_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms.

Y indicates saturated or unsaturated straight or branched hydrocarbon chain composed of 1-8 carbon atoms substituted by anyone or more halogen atoms, in which anyone or more carbon atoms are substituted by hetero atoms such as oxygen, sulfur or nitrogen.

Preferably, $R_2$ in formula (I) in this invention is the mono or polysubstituted group in the said benzo five-membered nitrogen heterocyclic ring, e.g., $R_2$ indicates mono-, di- or trisubstituted group, etc. $R_2$ indicates the group linked to any carbon atoms on benzo five-membered nitrogen heterocyclic ring, e.g., when A (or B) is CH atom, to which $R_2$ can also be linked It should be understood that, in term "aromatic group" used in this document, at least one ring should be a $C_{5-12}$ hydrocarbon mono or bicyclic ring of aromatic rings, in which one or more carbon atoms are substituted by hetero atoms of oxygen, sulfur and nitrogen. The examples of aromatic groups include aryl and hetero aryl groups, such as phenyl, naphthyl, benzothiazolyl, benzisothiazolyl, benzoxazolyl, benzisoxazolyl, benzimidazoyl, benzopyrazol, benzofuranyl, benzopyrimidinyl, benzopyridyl, quinoxalinyl, furyl, pyridyl or pyrimidinyl groups.

It should be understood that, in term "alicyclic group" used in this document, $C_{3-12}$ saturated hydrocarbon monocycle or bicycle, in which one or more carbon atoms are substituted by hetero atoms of oxygen, sulfur and nitrogen. The examples of alicyclic group include cyclopropyl, cyclobutyl, cyclopentyl, cyclohexyl, cycloheptyl, tetrahydrofuranyl, piperidyl or piperazidinyl, etc.

Except for otherwise specified, the term "halogen" used in this document indicates fluorine, chlorine, bromine or iodine.

Term "alkyl" used in this document includes straight or branch alkyl. Examples of the said "$C_1$-$C_6$ alkyl" group include methyl, ethyl, n-propyl, isopropyl, n-butyl, isobutyl, teriary butyl, n-pentyl, isopentyl, teriary pentyl, n-hexyl, isohexyl, etc.

Term "alkoxyl" used in this document indicates —O-alkyl, wherein alkyl groups include straight or branch alkyl groups. Examples of the said "$C_1$-$C_6$ alkoxyl" groups include methoxyl, ethoxyl, propoxyl, butoxyl, pentyloxyl and hexaoxyl, etc.

As used herein, definitions including general, preferable, more preferable, further preferable, particularly preferable and most preferable can be mutually combined.

In an embodiment, this invention offers the use of a compound in formula (I) and its salts acceptable pharmaceutically in preparation of vasodilative drugs:

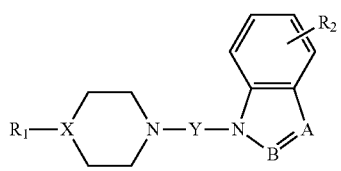

Wherein, $R_1$ indicates aromatic groups or alicyclic groups with mono or polysubstituted by $R_3$, wherein, The said aromatic groups preferably indicates phenyl, naphthyl, benzo five or six membered heterocyclic rings with hetero atoms of N, S or O, or five or six membered unsaturated heterocyclic rings. More preferably phenyl, naphthyl, benzothiazolyl, benzisothiazolyl, benzoxazolyl, benzisoxazolyl, benzimidazoyl, benzopyrazol, benzofuranyl, benzopyrimidinyl, benzopyridyl, quinoxalinyl, furyl, pyridyl or pyrimidinyl groups. Further preferably phenyl, benzisoxazolyl, benzisothiazolyl, benzopyrazol, benzofuranyl, naphthyl, furyl, pyridyl or pyrimidinyl, quinoxalinyl groups. Particularly preferably phenyl, benzisoxazolyl, benzisothiazolyl, benzofuranyl, quinoxalinyl, pyrimidinyl groups. Particularly preferably phenyl, benzisoxazolyl groups. Most preferably, when the said aromatic group is phenyl, X indicates N. Most preferably, when the said aromatic group is benzisoxazolyl, X indicates CH. Further preferably, when the said aromatic group is benzisoxazolyl, A indicates N.

The said alicyclic groups preferably indicates five or six membered saturated cycloalkyl groups, or five or six membered saturated heterocyclic groups with hetero atoms of N, S, O. More preferably cyclopentyl, cyclohexyl, tetrahydrofuryl, piperidyl or piperazinyl groups. Further preferably cyclohexyl, piperidyl or piperazinyl groups. Particularly preferably cyclohexyl group.

$R_3$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms. Preferably, $R_3$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl) or COOH, alkyl parts in the above said groups are substituted by anyone or more (e.g., 1-3 atoms) halogen atoms. More preferably, $R_3$ indicates H, F, Cl, Br, CN, $C_1$-$C_6$ alkyl or $C_1$-$C_6$ alkoxyl, CHO, COCH$_3$ or COOCH$_3$ in which alkyl parts are substituted 1-3 halogen atoms. Further preferably, $R_3$ indicates H, F, Cl, COCH$_3$, $C_1$-$C_4$ alkyl or $C_1$-$C_4$ alkoxyl in which alkyl parts are substituted 1-3 halogen atoms. Further more preferably, $R_3$ indicates H, F, Cl, CN, CF$_3$, CH$_3$, OCH$_3$ or COCH$_3$. Again preferably, $R_3$ indicates H, F, Cl, CN, CF$_3$, CH$_3$ or OCH$_3$. Most preferably, when X is N, $R_3$ indicates H, F, Cl or OCH$_3$. Particularly preferably, when X is CH, $R_3$ indicates H, F or CF$_3$, $R_3$ is more preferably F. If $R_3$ indicates polysubstituted group, $R_3$ is independently chosen from the above said groups.

A, B and X respectively indicate CH or N. Preferably, A and B all indicate N.

$R_2$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), alkyl parts in the above said groups are substituted by anyone or more halogen atoms. Preferably, $R_2$ indicates H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH or $NO_2$, alkyl parts in the above said groups are substituted by anyone or more (e.g., 1-3 atoms) halogen atoms. More preferably, $R_2$ indicates H, F, Cl, Br, CN, $NO_2$, $C_1$-$C_6$ alkyl or $C_1$-$C_6$ alkoxyl, CHO, COCH$_3$ or COOCH$_3$ in which alkyl parts are substituted 1-3 halogen atoms. Further preferably, $R_2$ indicates H, F, Cl, CN, CHO, COCH$_3$, COOCH$_3$, or $C_1$-$C_4$ alkyl or $C_1$-$C_4$ alkoxyl in which alkyl parts are substituted 1-3 halogen atoms. Further more preferably, $R_2$ indicates H, F, Cl, CN, CF$_3$, CH$_3$, OCH$_3$, CHO, COCH$_3$ or COOCH$_3$. Particularly preferably, when X indicates N, $R_2$ indicates H, F Cl, CN, CH$_3$ or COOCH$_3$, $R_2$ more preferably indicates H, F, Cl or CH$_3$. Particularly preferably, when X indicates CH, $R_2$ indicates H or OCH$_3$. Most preferably, $R_2$ indicates H. If $R_2$ indicates polysubstituted group, $R_2$ is independently chosen from the above said groups.

Y indicates saturated or unsaturated straight or branched hydrocarbon chain composed of 1-8 carbon atoms substituted by 1-3 halogen atoms, in which anyone or more carbon atoms are substituted by hetero atoms such as oxygen, sulfur or nitrogen. Preferably, Y indicates unsubstituted saturated alkyl group composed of 1-8 carbon atoms, or unsubstituted saturated alkyl group composed of 1-8 carbon atoms in which one carbon atom is replaced by oxygen or sulfur, e.g., —$C_{1-7}$ alkylidene-O—. More preferably, Y indicates methylene, ethylidene, propylidene, butylidene, pentylidene, hexylidene, heptylidene, caprylidene, oxymethylene, oxyethylidene, oxypropylidene, oxybutylidene, oxypentylidene, oxyhexylidene, oxyheptylidene, methyleneoxyl, ethylideneoxyl, propylideneoxyl, butylideneoxyl, pentylideneoxyl, hexylideneoxyl or heptylideneoxyl. Further more preferably, Y indicates methylene, ethylidene, propylidene, butylidene, pentylidene, hexylidene, heptylidene, caprylidene, methyleneoxyl, ethylideneoxyl, propylideneoxyl, butylideneoxyl, pentylideneoxyl, hexylideneoxyl or heptylideneoxyl. Particularly preferably, Y indicates ethylidene, propylidene, butylidene, ethylideneoxyl or propylideneoxyl. Further particularly preferably, Y indicates propylidene, butylidene or propylideneoxyl. Again particularly preferably, Y indicates propylidene or butylidene. Most preferably, when Y indicates butylidene, X indicates N. Most preferably, when Y indicates propylidene, X indicates CH.

In another embodiment, this invention offers the use of a compound in formula (I) and its salts acceptable pharmaceutically in preparation of vasodilative drugs:

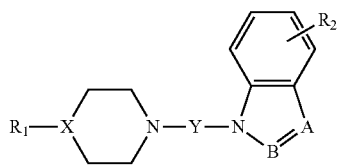

Wherein, $R_1$ indicates aromatic groups or alicyclic groups with mono or bisubstituted by $R_3$, wherein, The said aromatic groups indicate phenyl, benzisoxazolyl, benzofuranyl, benzisothiazolyl, benzopyranyl, benzopryazolyl or pyrimidinyl groups. The said alicyclic group indicates cyclohexyl.

Preferably, if X indicates N, $R_1$ indicates aromatic or alicyclic groups mono or bisubstituted by $R_3$, and the said aromatic groups indicate phenyl, benzisoxazolyl, benzofuranyl, benzisothiazolyl, benzopyranyl or pyrimidinyl groups. The said alicyclic group indicates cyclohexyl.

Preferably, if X indicates CH, $R_1$ indicates phenyl, benzisoxazolyl, benzisothiazolyl, benzofuranyl or benzopryazolyl groups mono or bisubstituted by $R_3$. More preferably, $R_1$ indicates aromatic groups monosubstituted by $R_3$, and the said aromatic groups preferably indicate phenyl or benzisoxazolyl. More preferably, when the said aromatic group is benzisoxazolyl, A indicates N.

$R_3$ indicates H, F, Cl, Br, CN, $C_1$-$C_6$ alkyl or $C_1$-$C_6$ alkoxyl, CHO, $COCH_3$, $COOCH_3$ in which alkyl parts are substituted 1-3 halogen atoms. Preferably, $R_3$ indicates H, F, Cl, CN, $CF_3$, unsubstituted $C_1$-$C_6$ alkyl or $C_1$-$C_6$ alkoxyl, CHO, $COCH_3$ or $COOCH_3$. More preferably, $R_3$ indicates H, F, Cl, $CH_3$, $OCH_3$, $COCH_3$ or $CF_3$. Further preferably, $R_3$ indicates H, F, Cl, $CF_3$, CN, $CH_3$ or $OCH_3$. Particularly preferably, $R_3$ indicates H, F, Cl, $CF_3$, $CH_3$ or $OCH_3$. Again preferably, R3 indicates H, F or $CF_3$. Most preferably, R3 indicates F. If $R_3$ indicates polysubstituted group, $R_3$ is independently chosen from the above said groups.

A, B and X respectively indicate CH or N. Preferably, A and B all indicate N.

$R_2$ indicates H, F, Cl, Br, CN, CHO, $COCH_3$, $COOCH_3$, or $C_1$-$C_6$ alkyl or $C_1$-$C_6$ alkoxyl in which alkyl parts are substituted 1-3 halogen atoms. Preferably, $R_2$ indicates H, F, Cl, CN, $CF_3$, $CH_3$, $OCH_3$, CHO, $COCH_3$ or $COOCH_3$. Further preferably, when X indicates N, $R_2$ indicates H, F, Cl or $CH_3$. Particularly preferably, when X indicates CH, $R_2$ indicates H, F Cl, CN, $CH_3$, $OCH_3$ or CHO, $R_2$ more preferably indicates H or $OCH_3$, $R_2$ most preferably indicates H. If $R_2$ indicates polysubstituted group, $R_2$ is independently chosen from the above said groups.

Y indicates saturated or unsaturated straight or branched hydrocarbon chain composed of 1-8 carbon atoms substituted by 2-3 halogen atoms, in which anyone or more carbon atoms are substituted by hetero atoms such as oxygen, sulfur or nitrogen. Preferably, Y indicates unsubstituted saturated alkyl group composed of 2-8 carbon atoms, or unsubstituted saturated alkyl group composed of 2-8 carbon atoms in which one carbon atom is replaced by oxygen or sulfur, e.g., —$C_{1-7}$ alkylidene-O—. More preferably, Y indicates ethylidene, propylidene, butylidene, pentylidene, hexylidene, ethylideneoxyl, propylideneoxyl or butylideneoxyl. Particularly preferably, Y indicates ethylidene, propylidene, butylidene or propylideneoxyl. Further preferably, Y indicates propylidene, butylidene or propylideneoxyl. Again preferably, Y indicates propylidene or butylidene. Most preferably, Y indicates propylidene.

In another embodiment, this invention offers the use of a compound in formula (I) and its salts acceptable pharmaceutically in preparation of vasodilative drugs:

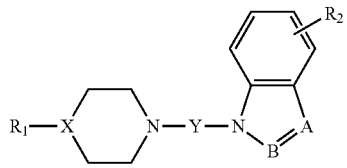

Wherein, $R_1$ indicates aromatic groups mono or bisubstituted by $R_3$, and the said aromatic groups indicate phenyl, benzisoxazolyl, benzofuranyl, benzopryazolyl or benzisothiazolyl groups. Preferably, when X indicates N, the said aromatic group indicates phenyl, benzisoxazolyl or benzisothiazolyl groups. Further preferably, when X indicates CH, the said aromatic group indicates phenyl, benzisoxazolyl, benzisothiazolyl, benzofuranyl or benzopryazolyl group.

More preferably, when X indicates CH, $R_1$ indicates aromatic groups monosubstituted by $R_3$, and the said aromatic groups preferably indicate phenyl or benzisoxazolyl. Preferably, when the said aromatic group is benzisoxazolyl, A indicates N.

$R_3$ indicates H, F, Cl, Br, CN, $C_1$-$C_6$ alkyl or $C_1$-$C_6$ alkoxyl in which alkyl parts are substituted 1-3 halogen atoms. Preferably, $R_3$ indicates H, F, Cl, CN, $CF_3$, unsubstituted $C_1$-$C_6$ alkyl or $C_1$-$C_6$ alkoxyl. More preferably, $R_3$ indicates H, F, Cl, $CF_3$, CN, $CH_3$ or $OCH_3$. More preferably, $R_3$ indicates H, F, Cl, $CH_3$, $OCH_3$ or $CF_3$. Particularly preferably, $R_3$ indicates H, F or $CF_3$. Most preferably, $R_3$ indicates F. If $R_3$ indicates polysubstituted group, $R_3$ is independently chosen from the above said groups.

A, B and X respectively indicate CH or N. Preferably, A and B all indicate N.

$R_2$ indicates H, F, Cl, Br, CN, CHO, $COCH_3$, or $C_1$-$C_6$ alkyl or $C_1$-$C_6$ alkoxyl in which alkyl parts are substituted 1-3 halogen atoms. More preferably, $R_2$ indicates H, F, Cl, CN, $CF_3$, $CH_3$, $OCH_3$ or $COCH_3$. Particularly preferably, $R_2$ indicates H, or $OCH_3$. Most preferably, R2 indicates H.

Y indicates saturated or unsaturated straight or branched hydrocarbon chain composed of 2-8 carbon atoms, in which anyone or more carbon atoms are substituted by hetero atoms such as oxygen, sulfur or nitrogen. Preferably, Y indicates unsubstituted saturated alkyl group composed of 2-8 carbon atoms, or unsubstituted saturated alkyl group composed of 2-8 carbon atoms in which one carbon atom is replaced by oxygen or sulfur, e.g., —$C_{1-7}$ alkylidene-O—. More preferably, Y indicates ethylidene, propylidene, butylidene or ethylideneoxyl. Particularly preferably, Y indicates propylidene or butylidene. Most preferably, Y indicates propylidene.

In another embodiment, this invention offers the use of a compound in formula (I) and its salts acceptable pharmaceutically in preparation of vasodilative drugs:

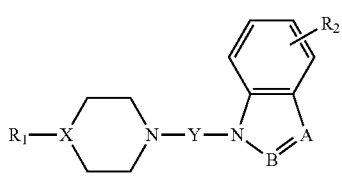

Wherein,

R₁ indicates aromatic groups mono or bisubstituted by $R_3$, wherein,

The said aromatic group indicates phenyl, benzisoxazolyl or benzisothiazolyl groups. Further preferably, when X indicates N, the said aromatic group indicates phenyl or benzisothiazolyl groups. Again preferably, when X indicates CH, the said aromatic group indicates phenyl or benzisoxazolyl group, more preferably benzisoxazolyl group.

$R_3$ indicates H, F, Cl, Br, $OCH_3$ or $CF_3$. Particularly preferably, $R_3$ indicates H, F, Cl or $CF_3$. Further preferably, when X indicates N, $R_3$ indicates H, Cl or $CF_3$. Again preferably, when X indicates CH, $R_3$ indicates H, F or $CF_3$. More preferably, R3 indicates F. If $R_3$ indicates polysubstituted group, $R_3$ is independently chosen from the above said groups.

A, B and X respectively indicate CH or N. Preferably, A and B all indicate N.

$R_2$ indicates H, F, Cl, Br, CN, $CH_3$ or $OCH_3$. Particularly preferably, $R_2$ indicates H, or $OCH_3$. Most preferably, R2 indicates H.

Y indicates saturated straight or branched hydrocarbon chain composed of 2-8 carbon atoms, in which anyone or more carbon atoms are substituted by hetero atoms of oxygen, sulfur or nitrogen, e.g., —$C_{1-7}$ alkylidene-O—. Preferably, Y indicates ethylidene, propylidene, butylidene or ethylideneoxyl. More preferably, Y indicates propylidene or butylidene. Further preferably, Y indicates butylidene, X indicates N. Again preferably, if Y indicates propylidene, X indicates CH.

In another embodiment, this invention offers the use of a compound in formula (I) and its salts acceptable pharmaceutically in preparation of vasodilative drugs:

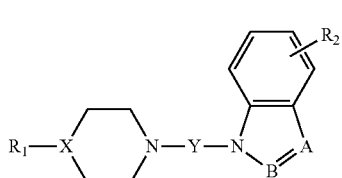

Wherein, when A, B and X all indicate N,

R₁ does not indicate phenyl group monosubstituted by H or $OCH_3$, and $R_2$ does not indicate H or $OCH_3$, $OCH_3$ is substituted on benzo five-membered nitrogen heterocyclic ring. And Y dose not indicate ethylidene, propylidene, butylidene or pentylidene.

In another embodiment, this invention offers the use of a compound in formula (I) or its salts acceptable pharmaceutically:

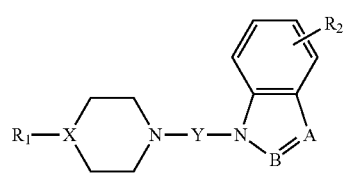

Wherein: when A and B all indicate N, and X indicates CH,

R₁ does not indicate benzoisoxazolyl substituted by 6-fluorine.

$R_2$ does not indicate H or Cl. And

Y dose not indicate ethylideneoxyl or propylideneoxyl.

In another embodiment, this invention offers the use of a compound in formula (I) or its salts acceptable pharmaceutically:

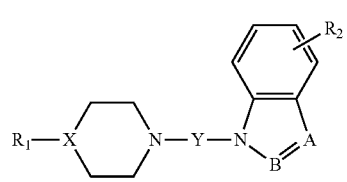

Wherein: when A, B and X all indicate CH,

R₁ does not indicate benzoisoxazolyl substituted by 6-fluorine.

$R_2$ does not indicate H, F, CN, $COOCH_3$ or Cl. And

Y dose not indicate ethylidene, propylidene, butylidene, pentylidene, ethylideneoxyl or propylideneoxyl.

In another embodiment, this invention offers the use of a compound in formula (I) or its salts acceptable pharmaceutically:

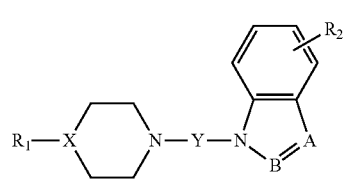

Wherein: when only A or B indicates CH, the other indicates N, and X indicates CH, R₁ does not indicate benzoisoxazolyl substituted by 6-fluorine.

$R_2$ does not indicate H, F or CN. And

Y does not indicate propylidene or butylidene.

In another embodiment, this invention offers the compound in formula (I) or its salts acceptable pharmaceutically

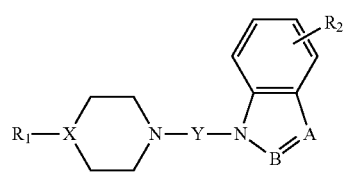

Wherein,

R₁ indicates phenyl or benzothiazol group monosubstituted by R₃, wherein,

R₃ indicates H or Cl. If R₃ indicates polysubstituted group, R₃ is independently chosen from the above said groups.

A and B independently indicate CH.

X indicates N,

R₂ indicates H or CN.

Y indicates butylidene.

In another embodiment, this invention offers the use of a compound in formula (I) or its salts acceptable pharmaceutically in preparation of vasodilative drugs:

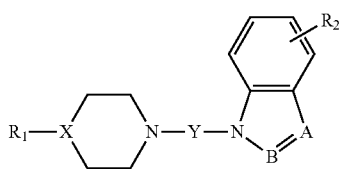

(I)

Wherein,

R₁ indicates benzisoxazolyl mono substituted by R₃, wherein R₃ indicates H, F, Cl, Br, OCH₃ or CF₃. Preferably, R₃ indicates H, F or CF₃. More preferably, R₃ indicates F.

A, B and X respectively indicate CH or N. Preferably, A and B all indicate N. X indicates CH.

R₂ indicates H, OCH₃. Preferably, R2 indicates H.

Y indicates saturated straight or branched hydrocarbon chain composed of 2-8 carbon atoms, in which anyone or more carbon atoms are substituted by hetero atoms of oxygen, sulfur or nitrogen, e.g., —C₁₋₇ alkylidene-O—. Preferably ethylidene, propylidene or butylidene. More preferably, Y indicates propylidene or butylidene. Most preferably propylidene.

In another embodiment, this invention offers the use of a compound in formula (I) or its salts acceptable pharmaceutically in preparation of vasodilative drugs:

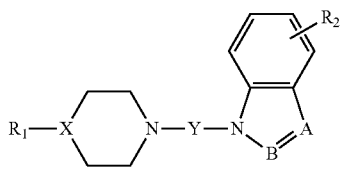

(I)

Wherein,

R₁ indicates benzisoxazolyl mono substituted by R₃, wherein R₃ indicates H, F, Cl, Br or OCH₃. Preferably, R₃ indicates H or F.

A and X indicate CH, B indicates CH or N.

R₂ indicates H, F, Cl, Br, CN or OCH₃.

Y indicates saturated straight or branched hydrocarbon chain composed of 2-8 carbon atoms, in which anyone or more carbon atoms are substituted by hetero atoms of oxygen, sulfur or nitrogen, e.g., —C₁₋₇ alkylidene-O—. Preferably ethylidene, propylidene, butylidene, pentylidene, ethylideneoxyl, propylideneoxyl or butylideneoxyl. Particularly preferably propylidene or butylidene. Most preferably propylidene.

The said benzo five-membered nitrogen heterocyclic piperazine or piperidine compounds include:

I-1 1-(4-(4-(3-chlorophenyl)piperazine-1-yl)butyl)-1H-benzimidazole,
I-2 1-(4-(4-(3-trifluoromethylphenyl)piperazine-1-yl)butyl)-1H-benzimidazole,
I-3 1-(4-(4-(2,3-dichlorophenyl)piperazine-1-yl)butyl)-1H-benzimidazole,
I-4 1-(4-(4-(2-methoxyphenyl)piperazine-1-yl)butyl)-1H-benzimidazole,
I-5 2-methyl-1-(4-(4-(3-trifluoromethylphenyl)piperazine-1-yl)butyl)-1H-benzimidazole,
I-6 6-fluoro-1-(4-(4-(3-trifluoromethylphenyl)piperazine-1-yl)butyl)-1H-benzimidazole,
I-7 1-(3-(4-phenylpiperazine-1-yl)propyl)-1H-benzimidazole,
I-8 1-(3-(4-(3-fluorophenyl)piperazine-1-yl)propyl)-1H-benzimidazole,
I-9 2-methyl-1-(3-(4-(3-fluorophenyl)piperazine-1-yl)propyl)-1H-benzimidazole,
I-10 1-(4-(4-(3-cyanophenyl)piperazine-1-yl)butyl)-1H-benzimidazole,
I-11 1-(4-(4-(4-methylphenyl)piperazine-1-yl)butyl)-1H-benzimidazole,
I-12 1-(4-(4-(2-furyl)piperazine-1-yl)butyl)-1H-benzimidazole,
I-13 1-(4-(4-(4-pyridyl)piperazine-1-yl)butyl)-1H-benzimidazole,
I-14 1-(4-(4-(2-pyrimidinyl)piperazine-1-yl)butyl)-1H-benzimidazole,
I-15 1-(4-(4-(1-cyclohexyl)piperazine-1-yl)butyl)-1H-benzimidazole,
I-16 1-(4-(4-(1-naphthyl)piperazine-1-yl)butyl)-1H-benzimidazole,
I-17 1-(4-(4-(2-quinoxalinyl)piperazine-1-yl)butyl)-1H-benzimidazole,
I-18 1-(4-(4-(3-(6-fluoro benzisoxazolyl))piperazine-1-yl)butyl)-1H-benzimidazole,
I-19 1-(4-(4-(3-(6-fluoro benzisothiazolyl))piperazine-1-yl)butyl)-1H-benzimidazole,
I-20 1-(4-(4-(3-benzimidazoyl)piperazine-1-yl)butyl)-1H-benzimidazole,
I-21 1-(4-(4-(3-(6-fluoro benzofuranyl))piperazine-1-yl)butyl)-1H-benzimidazole,
I-22 1-(3-(4-(3-(6-fluoro benzisoxazolyl))piperazine-1-yl)propoxyl)-1H-benzimidazole,
I-23 1-(4-(4-(3-trifluoromethylphenyl)piperazine-1-yl)propoxyl)-1H-benzimidazole,
I-24 1-(4-(4-(3-chlorphenyl)piperazine-1-yl)propoxyl)-1H-benzimidazole,
I-25 6-chloro-1-(4-(4-(3-trifluoromethylphenyl)piperazine-1-yl)butyl)-1H-benzimidazole,
I-26 6-cyano-1-(4-(4-(3-trifluoromethylphenyl)piperazine-1-yl)butyl)-1H-benzimidazole,
I-27 6-methoxycarbonyl-1-(4-(4-(3-trifluoromethylphenyl)piperazine-1-yl)butyl)-1H-benzimidazole,
I-28 2-chloro-1-(5-(4-(3-trifluoromethylphenyl)piperazine-1-yl)pentyl)-1H-benzimidazole,
I-29 1-(4-(4-(3-chlorophenyl)piperazine-1-yl)butyl)-1H-benzotriazole,
I-30 1-(4-(4-(3-fluorophenyl)piperazine-1-yl)butyl)-1H-benzotriazole,
I-31 1-(4-(4-(3-trifluoromethylphenyl)piperazine-1-yl)butyl)-1H-benzotriazole,
I-32 6-fluoro-1-(4-(4-(3-trifluoromethylphenyl)piperazine-1-yl)butyl)-1H-benzotriazole,
I-33 5,6-dimethyl-1-(4-(4-(3-trifluoromethylphenyl)piperazine-1-yl)butyl)-1H-benzotriazole, I-34 3-(4-(4-(1H-benzotriazole-1-yl)butyl)piperazine-1-yl)benzisothiazole,
I-35 3-(4-(4-(1H-benzotriazole-1-yl)butyl)piperazine-1-yl)benzisoxazole,
I-36 6-fluoro-3-(4-(4-(1H-benzotriazole-1-yl)butyl)piperazine-1-yl)benzisoxazole,
I-37 6-fluoro-3-(4-(3-(1H-benzotriazole-1-yl)propyl)piperazine-1-yl)benzisoxazole,
I-38 1-(3-(4-(2,3-dichlorophenyl)piperazine-1-yl)butyl)-1H-benzotriazole,
I-39 1-(3-(4-(3-methylphenyl)piperazine-1-yl)butyl)-1H-benzotriazole,
I-40 1-(4-(4-(3-methoxyphenyl)piperazine-1-yl)butyl)-1H-benzotriazole,
I-41 1-(4-(4-(3-cyanophenyl)piperazine-1-yl)butyl)-1H-benzotriazole,
I-42 1-(5-(4-(3-trifluoromethylphenyl)piperazine-1-yl)pentyl)-1H-benzotriazole,
I-43 1-(4-(4-(2-furyl)piperazine-1-yl)butyl)-1H-benzotriazole,
I-44 1-(4-(4-(4-pyridyl)piperazine-1-yl)butyl)-1H-benzotriazole,
I-45 1-(4-(4-(2-pyrimidinyl)piperazine-1-yl)butyl)-1H-benzotriazole,
I-46 1-(4-(4-cyclohexyl piperazine-1-yl)butyl)-1H-benzotriazole,
I-47 1-(4-(4-(1-naphthyl)piperazine-1-yl)butyl)-1H-benzotriazole,
I-48 1-(4-(4-(2-quinoxalinyl)piperazine-1-yl)butyl)-1H-benzotriazole,
I-49 1-(4-(4-(3-(6-fluoro benzisothiazolyl))piperazine-1-yl)butyl)-1H-benzotriazole,
I-50 1-(4-(4-(3-benzimidazoyl)piperazine-1-yl)butyl)-1H-benzotriazole,
I-51 1-(3-(4-(3-(6-fluoro benzofuranyl))piperazine-1-yl)propyl)-1H-benzotriazole,
I-52 1-(4-(4-(3-(6-fluoro benzisoxazolyl))piperazine-1-yl)propoxyl)-1H-benzotriazole,
I-53 6-fluoro-1-(4-(4-(3-(6-fluoro-benzisothiazolyl))piperazine-1-yl)propoxyl)-1H-benzotriazole,
I-54 6-chloro-1-(4-(4-(3-trifluoromethylphenyl)piperazine-1-yl)butyl)-1H-benzotriazole,
I-55 6-cyano-1-(4-(4-(3-trifluoromethylphenyl)piperazine-1-yl)butyl)-1H-benzotriazole,
I-56 6-methoxycarbonyl-1-(4-(4-(3-trifluoromethylphenyl)piperazine-1-yl)butyl)-1H-benzotriazole,
I-57 1-(4-(4-(3-trifluoromethylphenyl)piperazine-1-yl)butyl)-1H-indole,
I-58 6-cyano-1-(4-(4-(3-chlorophenyl)piperazine-1-yl)butyl)-1H-indole,
I-59 1-(3-(4-(3-trifluoromethylphenyl)piperazine-1-yl)propyl)-1H-benzopyrazole,
I-60 6-cyano-1-(3-(4-(2,3-fluorophenyl)piperazine-1-yl)propyl)-1H-benzopyrazole,
I-61 1-[4-(4-(4-fluoro)phenyl)piperazine]butyl-1H-indole,
I-62 1-[4-cyclohexyl piperazine]butyl-1H-indole,
I-63 1-[4-(4-(4-fluoro)phenyl)piperazine]butyl-5-acetyl-1H-indole,
I-64 1-[4-cyclohexyl piperazine]butyl-5-ecetyl-1H-indole,
I-65 1-[3-(4-(2,4-difluoro)phenyl)piperazine]butyl-5-acetyl-1H-indole,
I-66 1-[3-(4-(4-methyl)phenyl)piperazine]propyl-1H-indole,
I-67 1-[4-(4-(4-chloro)phenyl)piperazine]butyl-1H-indole,
I-68 1-[4-(4-(2-methyl)phenyl)piperazine]butyl-1H-indole,
I-69 1-[4-(4-(3-trifluoromethyl)phenyl)piperazine]butyl-1H-indole,
I-70 1-[3-(4-(4-methyl)phenyl)piperazine]propyl-5-methoxyl-1H-indole,
I-71 1-[4-(4-(4-trifluoromethoxyl)phenyl)piperazine]butyl-5-methoxyl-1H-indole,
I-72 1-[4-(4-(3-trifluoromethyl)phenyl)piperazine]butyl-5-methoxyl-1H-indole,
I-73 1-[3-(4-(2-methyl)phenyl)piperazine]butyl-5-methoxyl-1H-indole,
I-74 1-[3-(4-(2,4-difluoro)phenyl)piperazine]propyl-5-nitryl-1H-indole,
I-75 1-[4-(4-(4-chloro)phenyl)piperazine]butyl-5-nitryl-1H-indole,
I-76 1-[4-(4-(3-trifluoromethyl)phenyl)piperazine]butyl-5-nitryl-1H-indole,
I-77 1-[4-(4-(2-methoxyl)phenyl)piperazine]butyl-5-nitryl-1H-indole,
I-78 1-[4-(4-(2-methoxyl)phenyl)piperazine]butyl-5-chloro-1H-indole,
I-79 1-[4-(4-(3-trifluoromethyl)phenyl)piperazine]butyl-5-chloro-1H-indole,
I-80 1-[4-(4-(2,4-difluoro)phenyl)piperazine]butyl-5-chloro-1H-indole,
I-81 1-[2-(4-(2,4-di-trifluoromethyl)phenyl)piperazine]ethyl-5-chloro-1H-indole,
I-82 1-[2-(4-(2,4-dimethoxyl)phenyl)piperazine]ethyl-6-nitryl-1H-indole,
I-83 1-[2-(4-(2,4-dichloro)phenyl)piperazine]ethyl-6-methoxyl-1H-indole,
I-84 N-(3-(1H-benzotriazole-1-yl)propyl)-4-(3-benzisoxazolyl)piperidine,
I-85 N-(3-(1H-benzotriazole-1-yl)propyl)4-(3-(6-fluoro benzisoxazolyl))piperidine,
I-86 N-(3-(1H-benzotriazole-1-yl)propyl)-4-(3-(6-methyl benzisoxazolyl))piperidine,
I-87 N-(3-(1H-benzotriazole-1-yl)propyl)-4-(3-(6-methoxyl benzisoxazolyl))piperidine,
I-88 N-(3-(6-fluoro-1H-benzotriazole-1-yl)propyl)-4-(3-(6-fluoro benzisoxazolyl))piperidine,
I-89 N-(3-(6-chloro-1H-benzotriazole-1-yl)propyl)-4-(3-(6-fluoro benzisoxazolyl))piperidine,
I-90 N-(3-(6-methyl-1H-benzotriazole-1-yl)propyl)-4-(3-(6-fluoro benzisoxazolyl))piperidine,
I-91 N-(3-(6-methoxyl-1H-benzotriazole-1-yl)propyl)-4-(3-(6-fluoro benzisoxazolyl))piperidine,
I-92 N-(3-(6-formoxyl-1H-benzotriazole-1-yl)propyl)-4-(3-(6-fluoro benzisoxazolyl))piperidine,
I-93 N-(3-(6-methoxyl benzotriazolyl)propyl)-4-(3-benzisoxazolyl)piperidine,
I-94 N-(2-(1-benzotriazolyl)ethyl)-4-(3-(6-fluoro benzisoxazolyl))piperidine,
I-95 N-(4-(1-benzotriazolyl)butyl)-4-(3-(6-fluoro benzisoxazolyl))piperidine,
I-96 N-(4-(6-cyano benzotriazolyl)butyl)-4-(3-(6-fluoro benzisoxazolyl))piperidine,
I-97 N-(4-(6-cyano benzotriazolyl)butyl)-4-(3-(6-methoxyl benzisoxazolyl))piperidine,
I-98 N-(2-(6-methoxyl benzotriazolyl)ethoxyl)-4-(3-(6-fluoro benzisoxazolyl))piperidine,
I-99 N-(2-(1-benzotriazolyl)ethoxyl)-4-(3-(6-fluoro benzisoxazolyl))piperidine,
I-100 N-(3-(6-methoxyl benzotriazolyl)propyl)-4-(3-benzisothiazolyl)piperidine,
I-101 N-(3-(6-methoxyl benzotriazolyl)propyl)-4-(3-benzopyrazol)piperidine,
I-102 N-(3-(6-methoxyl benzotriazolyl)propyl)-4-(3-benzofuranyl)piperidine, I-103 N-(3-(1-benzopyrazol)propyl)-4-(3-(6-fluoro benzisoxazolyl))piperidine,
I-104 N-(4-(6-cyano benzopyrazol)butyl)-4-(3-(6-fluoro benzisoxazolyl))piperidine,
I-105 N-(2-(6-fluoro benzotriazolyl)ethoxyl)-4-(3-(6-fluoro benzisoxazolyl))piperidine,
I-106 N-(3-(6-fluoro benzotriazolyl)propoxyl)-4-(3-(6-fluoro benzisoxazolyl))piperidine,
I-107 N-(4-(1H-benzimidazoyl-1-yl)butyl)-4-(3-chlorophenyl)piperidine,
I-108 N-(4-(1H-benzotriazole-1-yl)butyl)-4-(3-chlorophenyl)piperidine,
I-109 N-(4-(1H-benzimidazoyl-1-yl)butyl)-4-(3-trifluoromethylphenyl)piperidine,
I-110 N-(4-(1H-benzotriazole-1-yl)butyl)-4-(3-trifluoromethylphenyl)piperidine,
I-111 N-(4-(1H-benzimidazoyl-1-yl)butyl)-4-(3-fluorophenyl)piperidine,
I-112 N-(4-(1H-benzimidazoyl-1-yl)butyl)-4-(2-methoxylphenyl)piperidine,
I-113 N-(4-(6-fluoro-1H-benzotriazole-1-yl)butyl)-4-(3-trifluoromethylphenyl)piperidine,
I-114 N-(4-(6-methoxyl-1H-benzotriazole-1-yl)butyl)-4-(3-trifluoromethylphenyl)piperidine,
I-115 N-(4-(6-cyano-1H-benzotriazole-1-yl)butyl)-4-(3-trifluoromethylphenyl)piperidine,
I-116 N-(4-(1H-benzotriazole-1-yl)propoxyl)-4-(3-trifluoromethylphenyl)piperidine,
I-117 N-(4-(1H-benzimidazole-1-yl)propoxyl)-4-(3-trifluoromethylphenyl)piperidine,
I-118 N-(4-(1H-benzimidazoyl-1-yl)butyl)-4-(2-furyl)piperidine,
I-119 N-(4-(1H-benzimidazoyl-1-yl)butyl)-4-(4-pyridyl)piperidine,
I-120 N-(4-(1H-benzimidazoyl-1-yl)butyl)-4-(2-pyrimidinyl)piperidine,
I-121 N-(4-(1H-benzotriazole-1-yl)butyl)-4-(4-cyclohexyl)piperidine,
I-122 N-(4-(1H-benzotriazole-1-yl)butyl)-4-(1-naphthyl)piperidine,
I-123 N-(4-(1H-benzotriazole-1-yl)butyl)-4-(2-quinoxalinyl)piperidine,
I-124 N-(4-(1H-benzimidazoyl-1-yl)butyl)-4-(3-chlorophenyl)piperidine,
I-125 N-(4-(1H-benzotriazole-1-yl)butyl)-4-(3-chlorophenyl)piperidine,
I-126 N-(4-(1H-benzimidazoyl-1-yl)butyl)-4-(3-trifluoromethylphenyl)piperidine,
I-127 N-(4-(1H-benzotriazole-1-yl)butyl)-4-(3-trifluoromethylphenyl)piperidine,
I-128 N-(4-(1H-benzimidazoyl-1-yl)butyl)-4-(3-fluorophenyl)piperidine,
I-129 N-(4-(1H-benzimidazoyl-1-yl)butyl)-4-(2-methoxylphenyl)piperidine,
I-130 N-(4-(6-fluoro-1H-benzotriazole-1-yl)butyl)-4-(3-trifluoromethylphenyl)piperidine,
I-131 N-(4-(6-methoxyl-1H-benzotriazole-1-yl)butyl)-4-(3-trifluoromethylphenyl)piperidine,
I-132 N-(4-(6-cyano-1H-benzotriazole-1-yl)butyl)-4-(3-trifluoromethylphenyl)piperidine,
I-133 N-(4-(1H-benzotriazole-1-yl)propoxyl)-4-(3-trifluoromethylphenyl)piperidine,
I-134 N-(4-(1H-benzimidazole-1-yl)propoxyl)-4-(3-trifluoromethylphenyl)piperidine,
I-135 N-(3-(1H-benzotriazole-1-yl)propyl)-4-(3-(6-methyl benzisoxazolyl))piperidine,
I-136 N-(3-(1H-benzotriazole-1-yl)propyl)-4-(3-(6-methoxyl benzisoxazolyl))piperidine,
I-137 N-(3-(6-fluoro-1H-benzotriazole-1-yl)propyl)-4-(3-(6-fluoro benzisoxazolyl))piperidine,
I-138 N-(3-(6-chloro-1H-benzotriazole-1-yl)propyl)-4-(3-(6-fluoro benzisoxazolyl))piperidine,
I-139 N-(3-(6-methyl-1H-benzotriazole-1-yl)propyl)-4-(3-(6-fluoro benzisoxazolyl))piperidine,
I-140 N-(3-(6-methoxyl-1H-benzotriazole-1-yl)propyl)-4-(3-(6-fluoro benzisoxazolyl))piperidine,
I-141 N-(3-(6-formoxyl-1H-benzotriazole-1-yl)propyl)-4-(3-(6-fluoro benzisoxazolyl))piperidine,
I-142 N-(3-(6-methoxyl benzotriazolyl)propyl)-4-(3-benzisoxazolyl)piperidine,
I-143 N-(2-(1-benzotriazolyl)ethyl)-4-(3-(6-fluoro benzisoxazolyl))piperidine,
I-144 N-(4-(1-benzotriazolyl)butyl)-4-(3-(6-fluoro benzisoxazolyl))piperidine,
I-145 N-(4-(6-cyano benzotriazolyl)butyl)-4-(3-(6-fluoro benzisoxazolyl))piperidine,
I-146 N-(4-(6-cyano benzotriazolyl)butyl)-4-(3-(6-methoxyl benzisoxazolyl))piperidine,
I-147 N-(2-(6-methoxyl benzotriazolyl)ethoxyl)-4-(3-benzisoxazolyl)piperidine,
I-148 N-(2-(1-benzotriazolyl)ethoxyl)-4-(3-fluoro benzisoxazolyl)piperidine,
I-149 N-(3-(6-methoxyl benzotriazolyl)propyl)-4-(3-(6-fluoro benzisothiazolyl))piperidine,
I-150 N-(3-(6-methoxyl benzotriazolyl)propyl)-4-(3-(6-fluoro benzopyrazol))piperidine,
I-151 N-(3-(6-methoxyl benzotriazolyl)propyl)-4-(3-(6-fluoro benzofuranyl))piperidine,
I-152 N-(4-(1H-benzimidazoyl-1-yl)butyl)-4-(2-furyl)piperidine,
I-153 N-(4-(1H-benzimidazoyl-1-yl)butyl)-4-(4-pyridyl)piperidine,
I-154 N-(4-(1H-benzimidazoyl-1-yl)butyl)-4-(2-pyrimidinyl)piperidine,
I-155 N-(4-(1H-benzotriazole-1-yl)butyl)-4-cyclohexyl piperidine,
I-156 N-(4-(1H-benzotriazole-1-yl)butyl)-4-(1-naphthyl)piperidine,
I-157 N-(4-(1H-benzotriazole-1-yl)butyl)-4-(2-quinoxalinyl)piperidine.

Specific chemical structures are illustrated in the following table:

| Code | Chemical structure |
|---|---|
| I-1 | 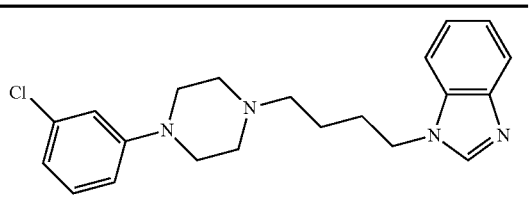 |
| I-2 | 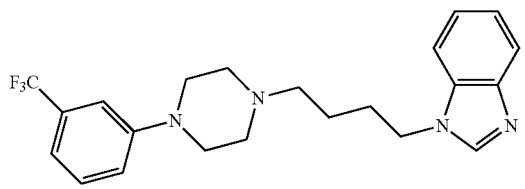 [SMILES: FC(F)(F)c1cccc(N2CCN(CCCCn3cnc4ccccc43)CC2)c1] |

| Code | Chemical structure |
|---|---|
| I-3 | 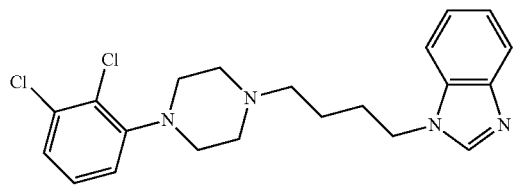 [SMILES: Clc1cccc(N2CCN(CCCCn3cnc4ccccc43)CC2)c1Cl] |
| I-4 | 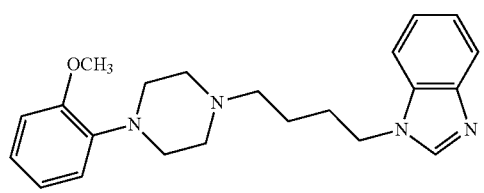 |
| I-5 | 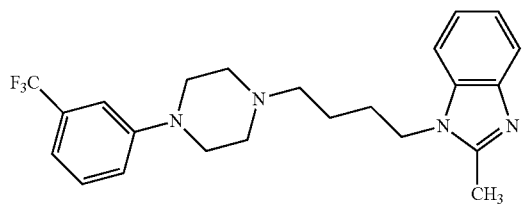 [SMILES: Cc1nc2ccccc2n1CCCCN1CCN(c2cccc(C(F)(F)F)c2)CC1] |
| I-6 | 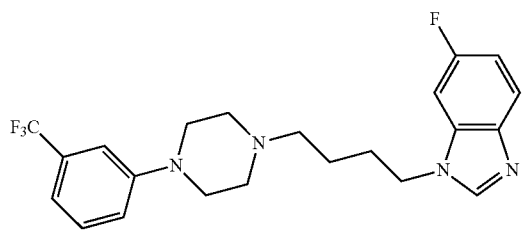 [SMILES: Fc1ccc2ncn(CCCCN3CCN(c4cccc(C(F)(F)F)c4)CC3)c2c1] |
| I-7 | 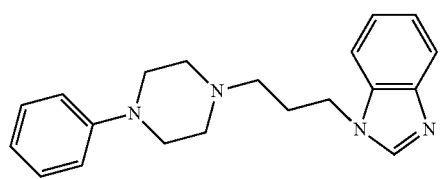 [SMILES: c1ccc(N2CCN(CCCn3cnc4ccccc43)CC2)cc1] |
| I-8 | 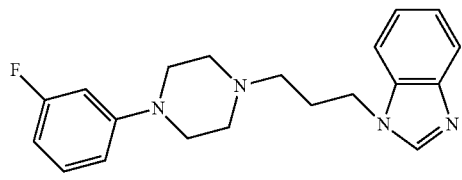 [SMILES: Fc1cccc(N2CCN(CCCn3cnc4ccccc43)CC2)c1] |
| I-9 | 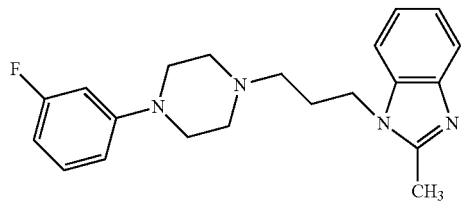 [SMILES: Cc1nc2ccccc2n1CCCN1CCN(c2cccc(F)c2)CC1] |
| I-10 | 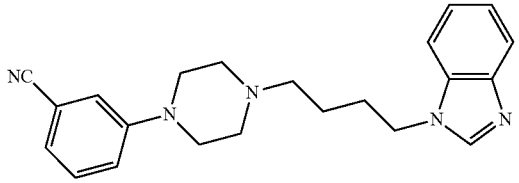 [SMILES: N#Cc1cccc(N2CCN(CCCCn3cnc4ccccc43)CC2)c1] |
| I-11 | 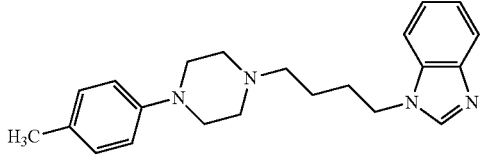 [SMILES: Cc1ccc(N2CCN(CCCCn3cnc4ccccc43)CC2)cc1] |
| I-12 | 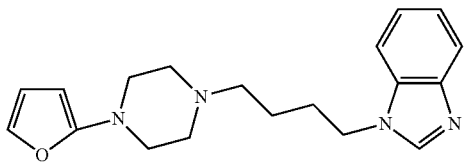 |
| I-13 | 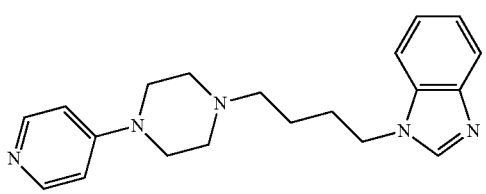 [SMILES: c1ccc2c(c1)ncn2CCCCN1CCN(c2ccncc2)CC1] |
| I-14 | 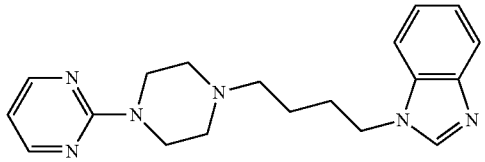 |
| I-15 | 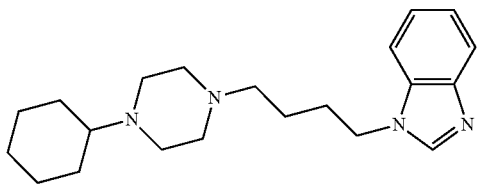 [SMILES: c1ccc2c(c1)ncn2CCCCN1CCN(C2CCCCC2)CC1] |
| I-16 | 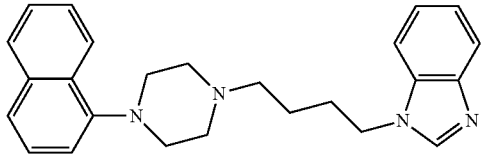 [SMILES: c1ccc2c(N3CCN(CCCCn4cnc5ccccc54)CC3)cccc2c1] |
| I-17 | 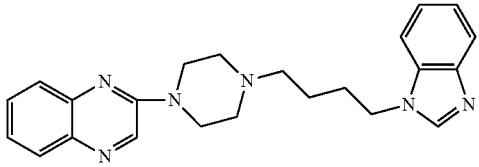 |

| Code | Chemical structure |
|---|---|
| I-18 | 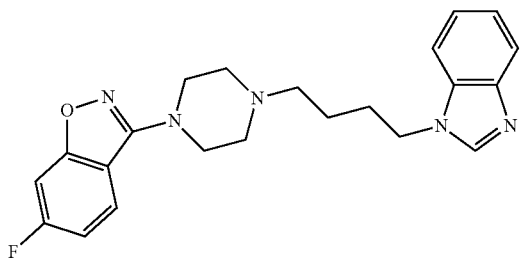 [SMILES: Fc1ccc2c(N3CCN(CCCCn4cnc5ccccc54)CC3)noc2c1] |
| I-19 | 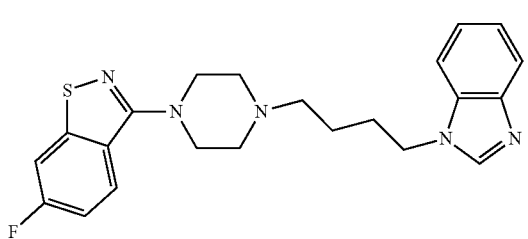 [SMILES: Fc1ccc2c(N3CCN(CCCCn4cnc5ccccc54)CC3)nsc2c1] |
| I-20 | 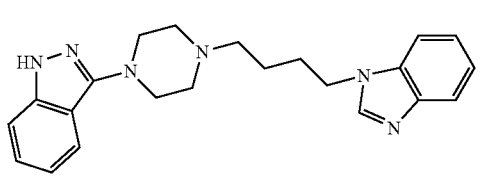 [SMILES: c1ccc2c(c1)ncn2CCCCN1CCN(c2n[nH]c3ccccc23)CC1] |
| I-21 | 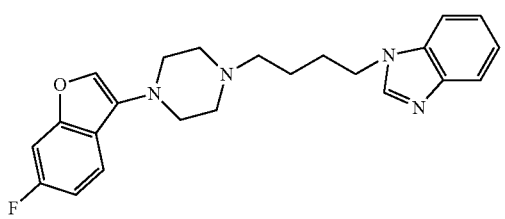 [SMILES: Fc1ccc2c(N3CCN(CCCCn4cnc5ccccc54)CC3)coc2c1] |
| I-22 | 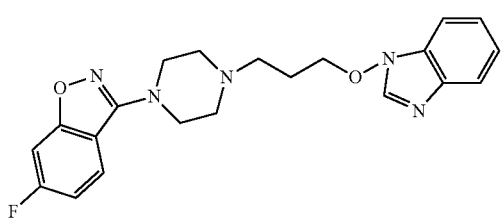 [SMILES: Fc1ccc2c(N3CCN(CCCOn4cnc5ccccc54)CC3)noc2c1] |
| I-23 | 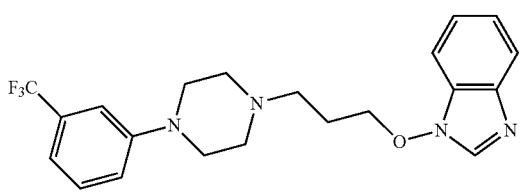 |
| I-24 | 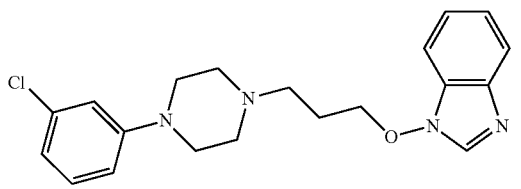 [SMILES: Clc1cccc(N2CCN(CCCOn3cnc4ccccc43)CC2)c1] |
| Code | Chemical structure |
|---|---|
| I-25 | 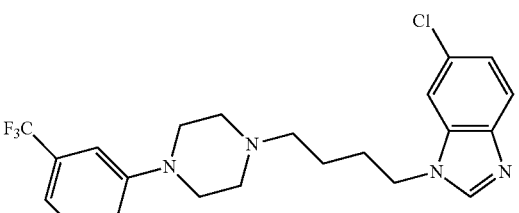 |
| I-26 | 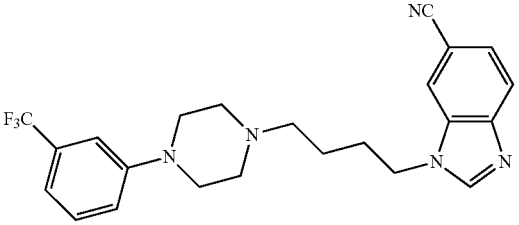 [SMILES: N#Cc1ccc2ncn(CCCCN3CCN(c4cccc(C(F)(F)F)c4)CC3)c2c1] |
| I-27 | 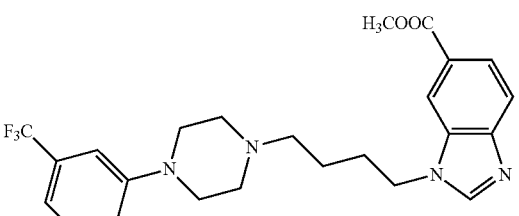 |
| I-28 | 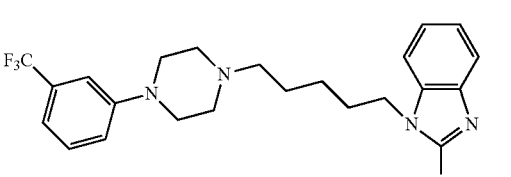 |
| I-29 | 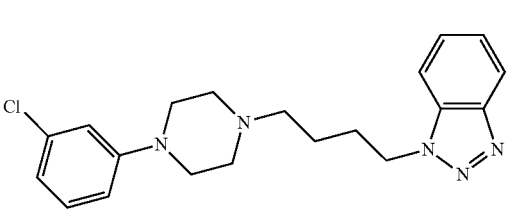 |
| I-30 | 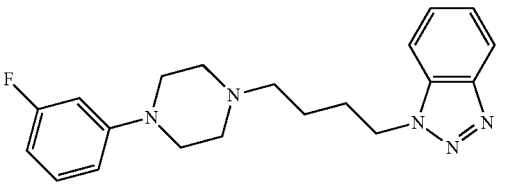 |
| I-31 | 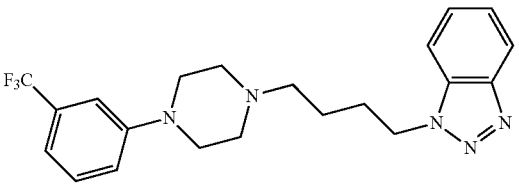 [SMILES: FC(F)(F)c1cccc(N2CCN(CCCCn3nnc4ccccc43)CC2)c1] |

-continued
| Code | Chemical structure |
|---|---|
| I-32 | 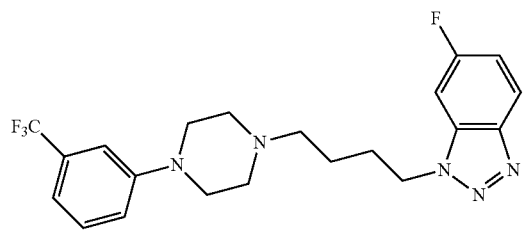 [SMILES: Fc1ccc2nnn(CCCCN3CCN(c4cccc(C(F)(F)F)c4)CC3)c2c1] |
| I-33 | 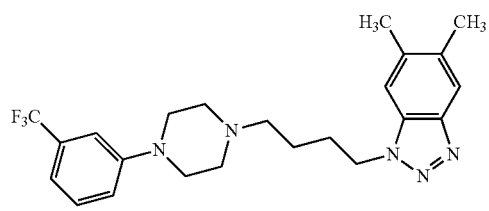 [SMILES: Cc1cc2nnn(CCCCN3CCN(c4cccc(C(F)(F)F)c4)CC3)c2cc1C] |
| I-34 | 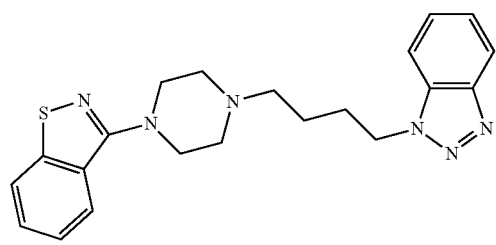 [SMILES: c1ccc2c(c1)nnn2CCCCN1CCN(c2noc3ccccc23)CC1] |
| I-35 | 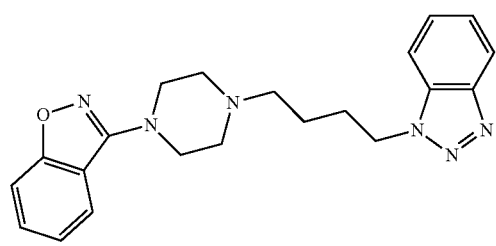 |
| I-36 | 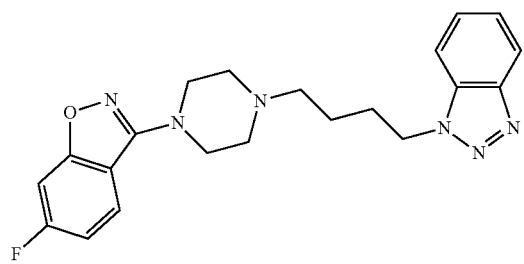 [SMILES: Fc1ccc2c(N3CCN(CCCCn4nnc5ccccc54)CC3)noc2c1] |
| I-37 | 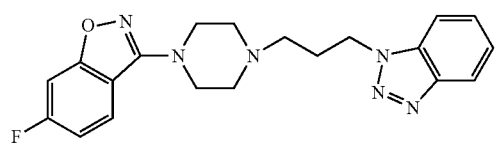 [SMILES: Fc1ccc2c(N3CCN(CCCn4nnc5ccccc54)CC3)noc2c1] |
| I-38 | 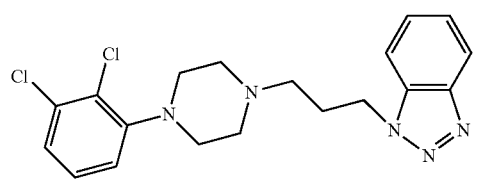 [SMILES: Clc1cccc(N2CCN(CCCn3nnc4ccccc43)CC2)c1Cl] |
-continued
| Code | Chemical structure |
|---|---|
| I-39 | 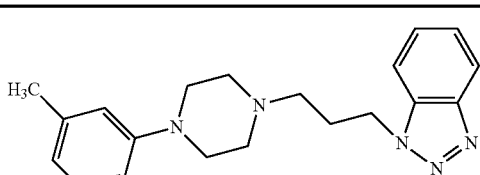 |
| I-40 | 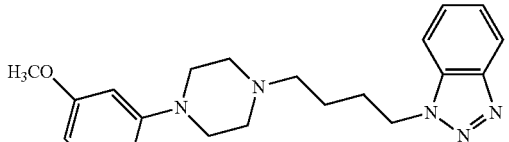 |
| I-41 | 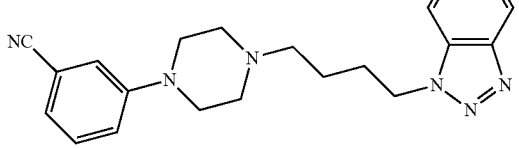 |
| I-42 | 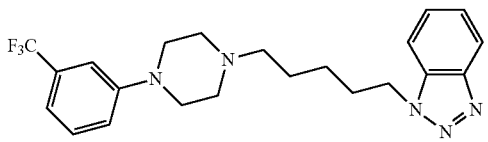 [SMILES: FC(F)(F)c1cccc(N2CCN(CCCCCn3nnc4ccccc43)CC2)c1] |
| I-43 | 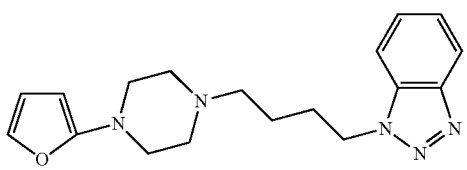 [SMILES: c1coc(N2CCN(CCCCn3nnc4ccccc43)CC2)c1] |
| I-44 | 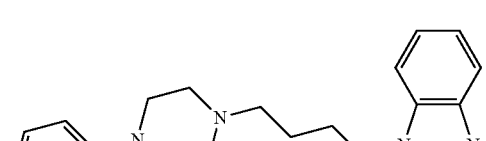 |
| I-45 | 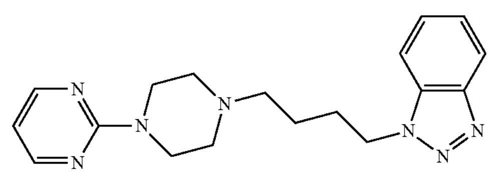 [SMILES: c1cnc(N2CCN(CCCCn3nnc4ccccc43)CC2)nc1] |
| I-46 | 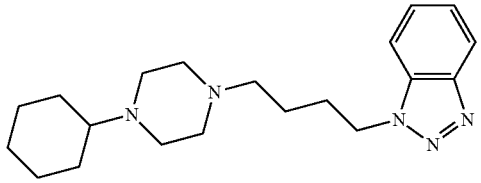 [SMILES: c1ccc2c(c1)nnn2CCCCN1CCN(C2CCCCC2)CC1] |

| Code | Chemical structure |
|---|---|
| I-47 | 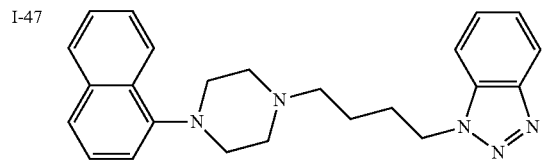 |
| I-48 | 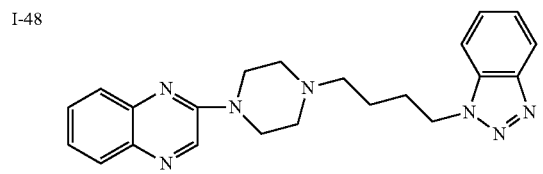 |
| I-49 | 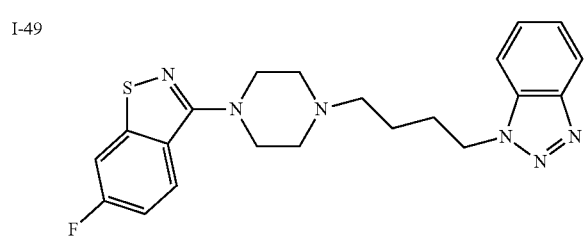 |
| I-50 | 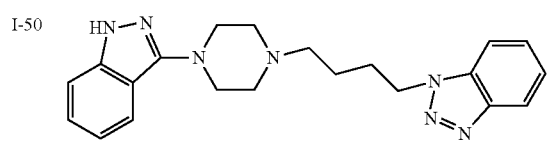 |
| I-51 | 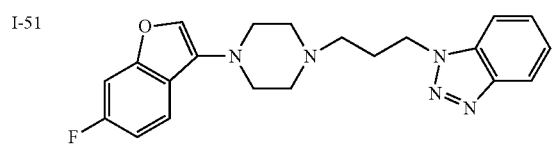 |
| I-52 | 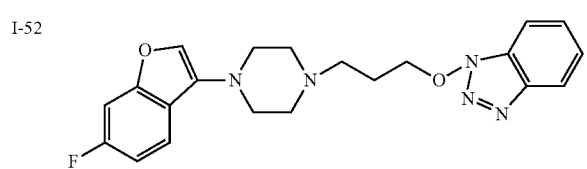 |
| I-53 | 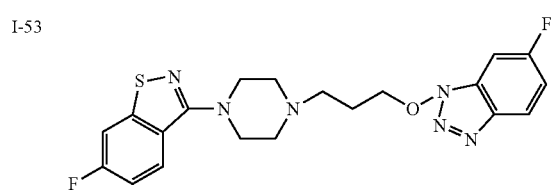 |
| I-54 | 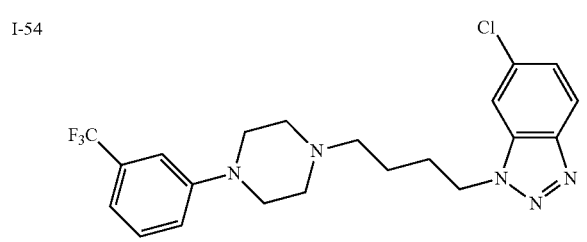 |
| Code | Chemical structure |
|---|---|
| I-55 | 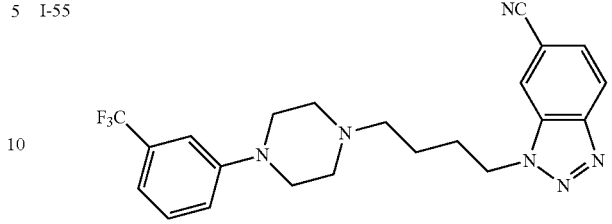 |
| I-56 | 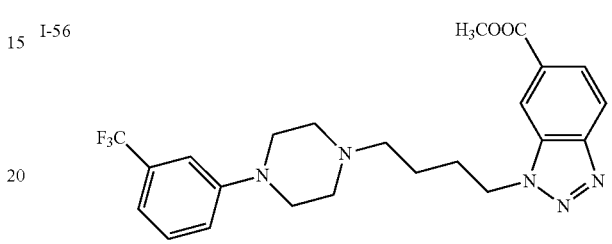 |
| I-57 | 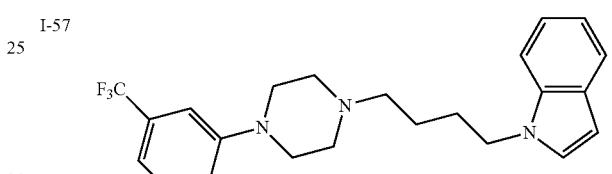 |
| I-58 | 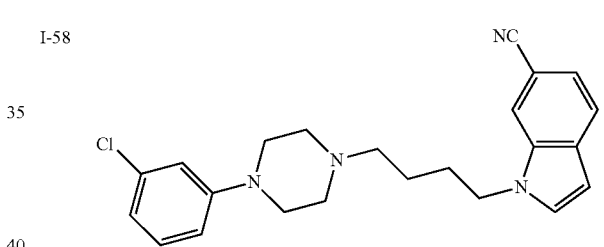 |
| I-59 | 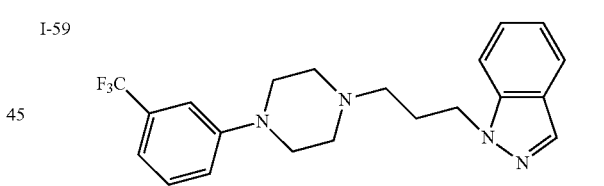 |
| I-60 | 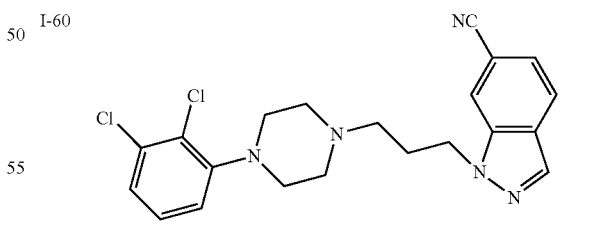 |
| I-61 | 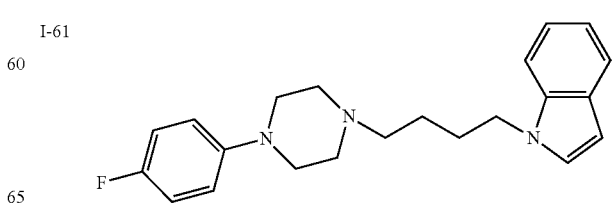 |

| Code | Chemical structure |
|---|---|
| I-62 | 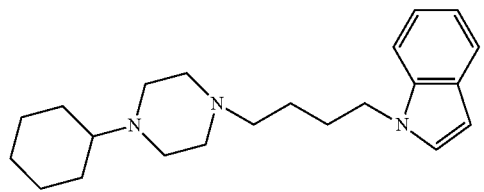 [SMILES: c1ccc2c(c1)ccn2CCCCN1CCN(C2CCCCC2)CC1] |
| I-63 | 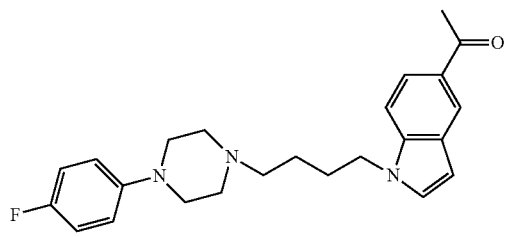 [SMILES: CC(=O)c1ccc2c(ccn2CCCCN2CCN(c3ccc(F)cc3)CC2)c1] |
| I-64 | 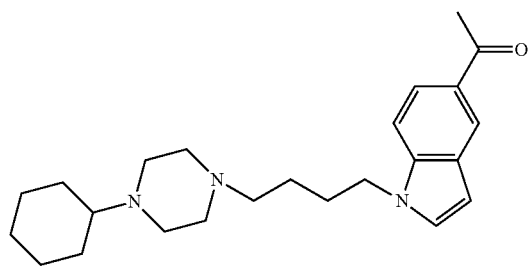 [SMILES: CC(=O)c1ccc2c(ccn2CCCCN2CCN(C3CCCCC3)CC2)c1] |
| I-65 | 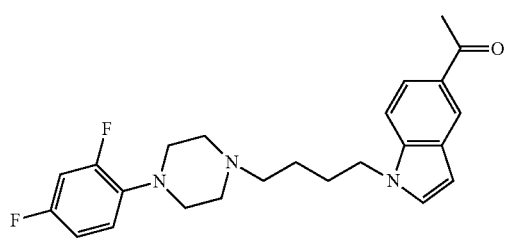 [SMILES: CC(=O)c1ccc2c(ccn2CCCCN2CCN(c3ccc(F)cc3F)CC2)c1] |
| I-66 | 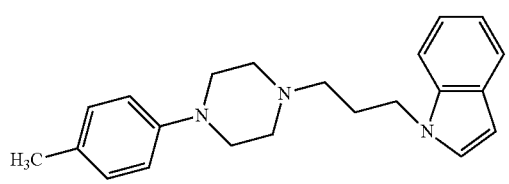 [SMILES: Cc1ccc(N2CCN(CCCn3ccc4ccccc43)CC2)cc1] |
| I-67 | 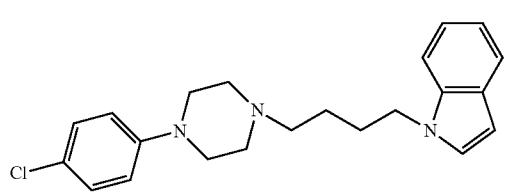 [SMILES: Clc1ccc(N2CCN(CCCCn3ccc4ccccc43)CC2)cc1] |
| I-68 | 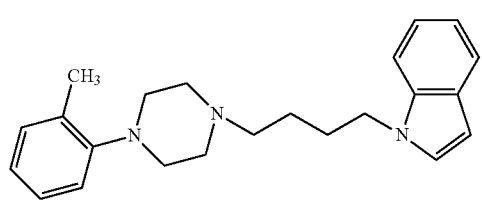 [SMILES: Cc1ccccc1N1CCN(CCCCn2ccc3ccccc32)CC1] |
| Code | Chemical structure |
|---|---|
| I-69 | 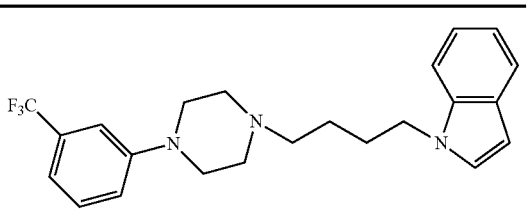 |
| I-70 | 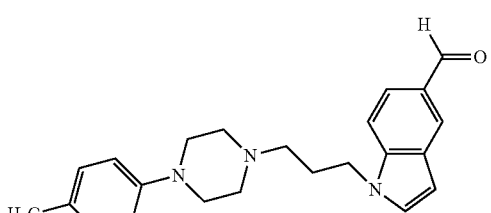 |
| I-71 | 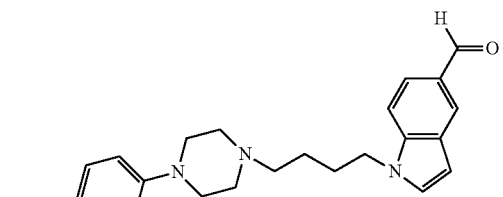 |
| I-72 | 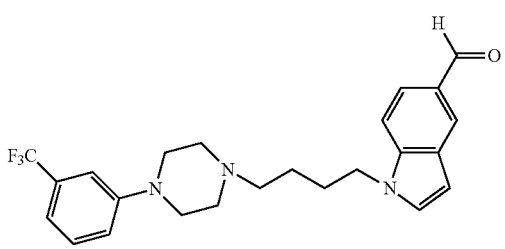 [SMILES: O=Cc1ccc2c(ccn2CCCCN2CCN(c3cccc(C(F)(F)F)c3)CC2)c1] |
| I-73 | 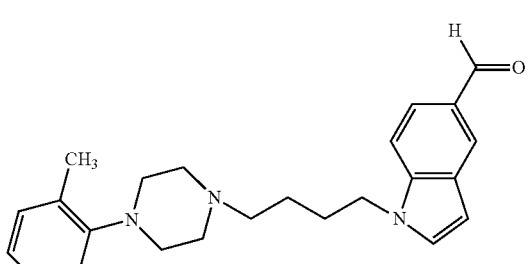 |
| I-74 | 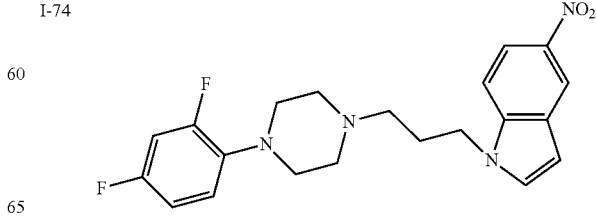 |

| Code | Chemical structure |
|---|---|
| I-75 | 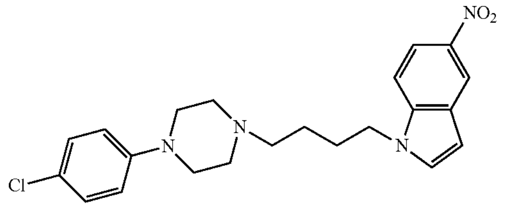 [SMILES: O=[N+]([O-])c1ccc2c(ccn2CCCCN2CCN(c3ccc(Cl)cc3)CC2)c1] |
| I-76 | 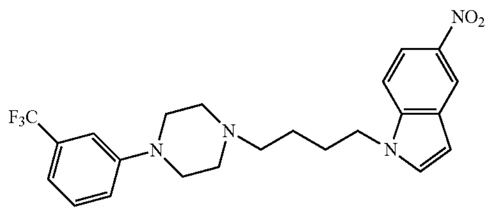 [SMILES: O=[N+]([O-])c1ccc2c(ccn2CCCCN2CCN(c3cccc(C(F)(F)F)c3)CC2)c1] |
| I-77 | 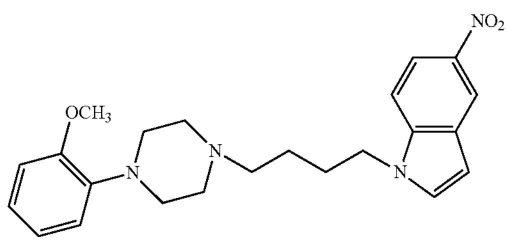 [SMILES: COc1ccccc1N1CCN(CCCCn2ccc3cc([N+](=O)[O-])ccc32)CC1] |
| I-78 | 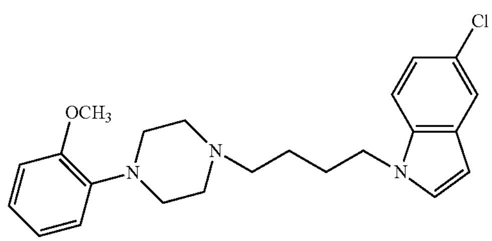 [SMILES: COc1ccccc1N1CCN(CCCCn2ccc3cc(Cl)ccc32)CC1] |
| I-79 | 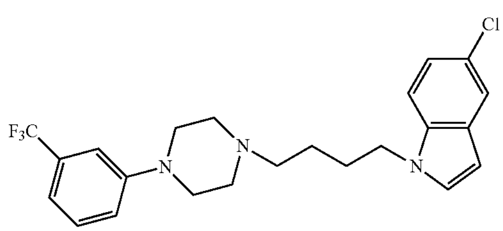 [SMILES: FC(F)(F)c1cccc(N2CCN(CCCCn3ccc4cc(Cl)ccc43)CC2)c1] |
| I-80 | 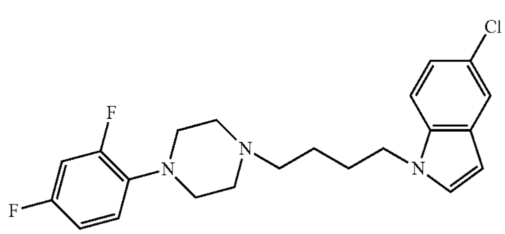 [SMILES: Fc1ccc(N2CCN(CCCCn3ccc4cc(Cl)ccc43)CC2)c(F)c1] |
| I-81 | 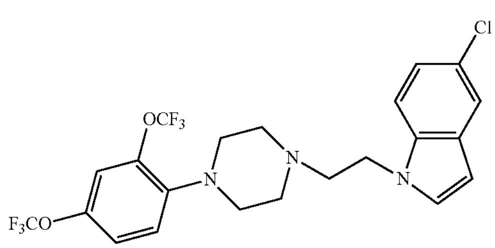 [SMILES: FC(F)(F)Oc1ccc(N2CCN(CCn3ccc4cc(Cl)ccc43)CC2)c(OC(F)(F)F)c1] |
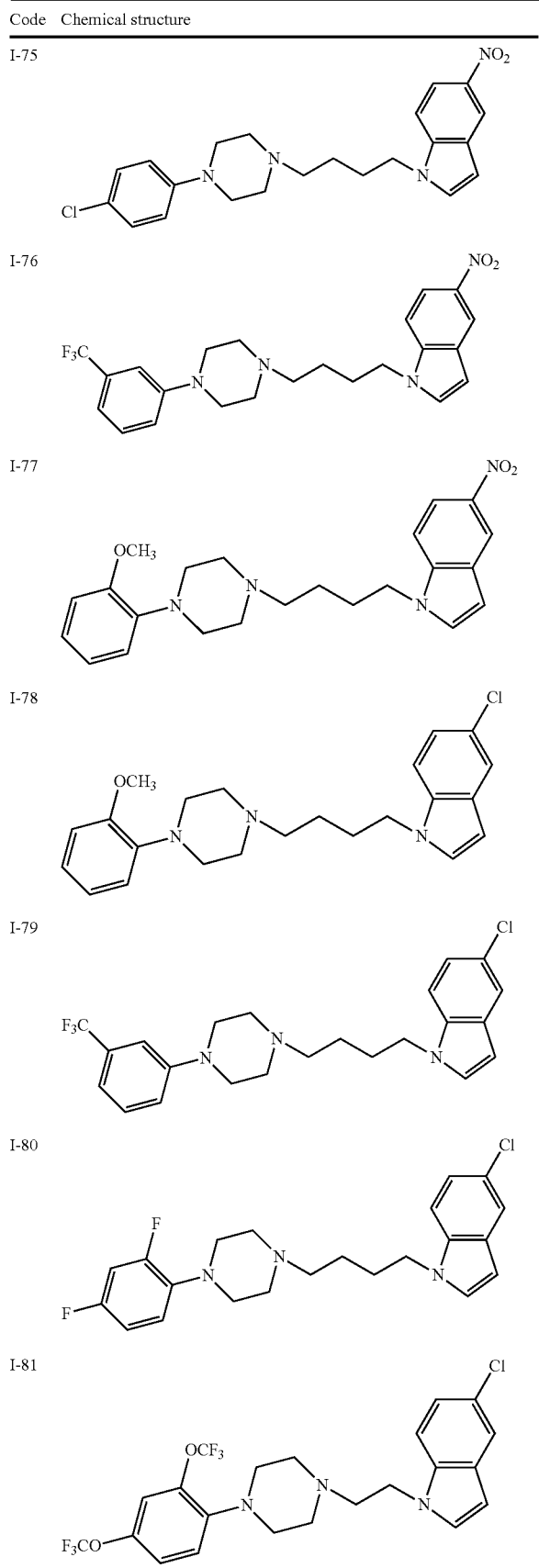
| Code | Chemical structure |
|---|---|
| I-82 | 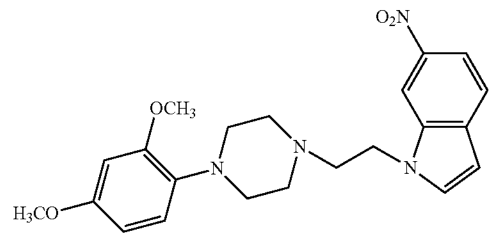 [SMILES: COc1ccc(N2CCN(CCn3ccc4ccc([N+](=O)[O-])cc43)CC2)c(OC)c1] |
| I-83 | 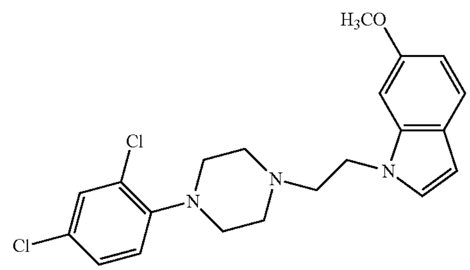 [SMILES: COc1ccc2ccn(CCN3CCN(c4ccc(Cl)cc4Cl)CC3)c2c1] |
| I-84 | 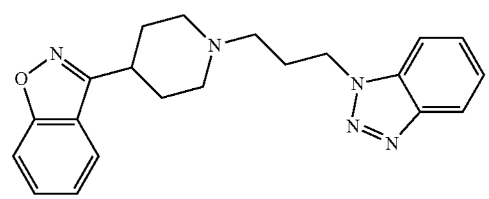 [SMILES: c1ccc2c(c1)nnn2CCCN1CCC(c2noc3ccccc23)CC1] |
| I-85 | 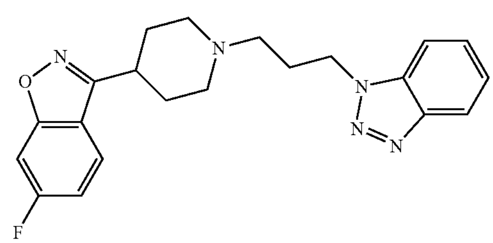 [SMILES: Fc1ccc2c(C3CCN(CCCn4nnc5ccccc54)CC3)noc2c1] |
| I-86 | 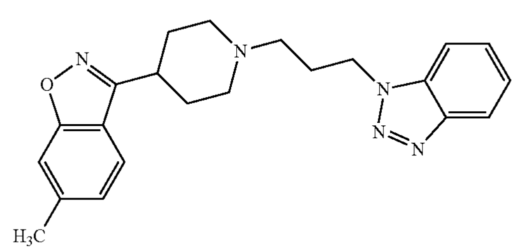 [SMILES: Cc1ccc2c(C3CCN(CCCn4nnc5ccccc54)CC3)noc2c1] |
| I-87 | 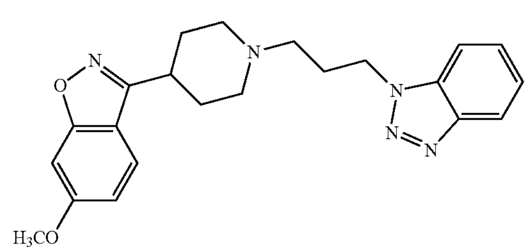 [SMILES: COc1ccc2c(C3CCN(CCCn4nnc5ccccc54)CC3)noc2c1] |
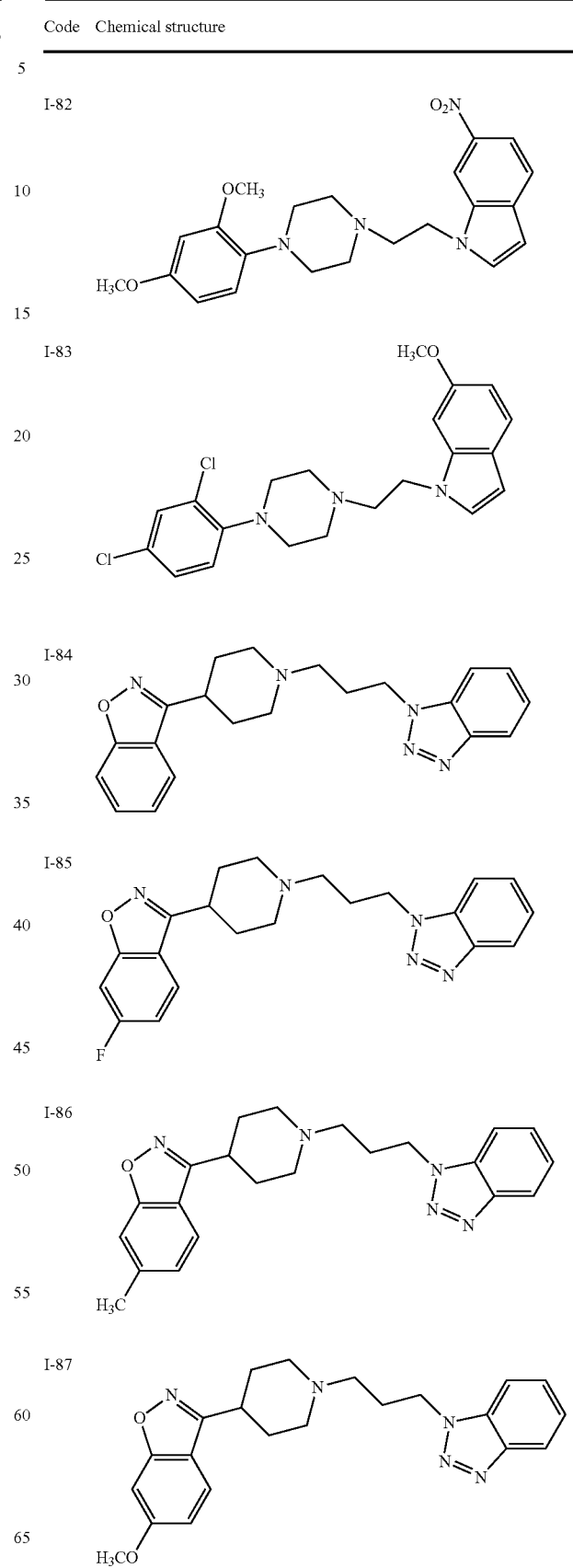

| Code | Chemical structure |
|---|---|
| I-88 | 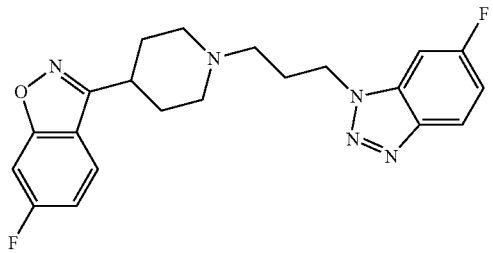 [SMILES: Fc1ccc2c(C3CCN(CCCn4nnc5ccc(F)cc54)CC3)noc2c1] |
| I-89 | 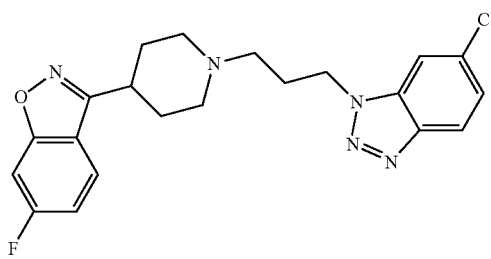 |
| I-90 | 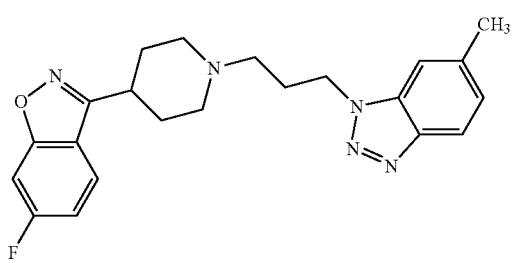 [SMILES: Cc1ccc2nnn(CCCN3CCC(c4noc5cc(F)ccc45)CC3)c2c1] |
| I-91 | 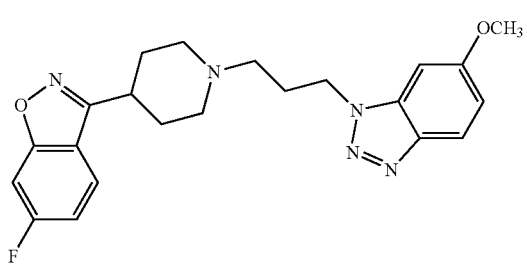 [SMILES: COc1ccc2nnn(CCCN3CCC(c4noc5cc(F)ccc45)CC3)c2c1] |
| I-92 | 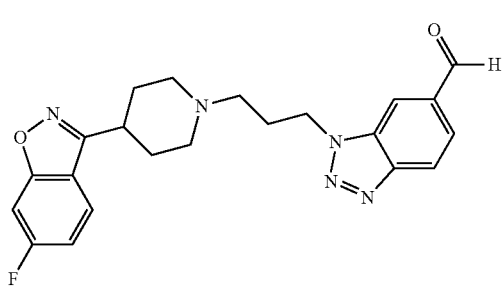 [SMILES: O=Cc1ccc2nnn(CCCN3CCC(c4noc5cc(F)ccc45)CC3)c2c1] |
| I-93 | 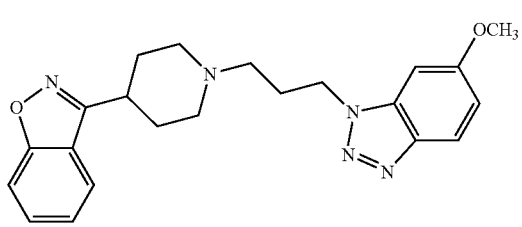 [SMILES: COc1ccc2nnn(CCCN3CCC(c4noc5ccccc45)CC3)c2c1] |
| I-94 | 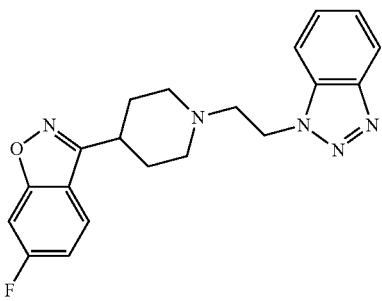 [SMILES: Fc1ccc2c(C3CCN(CCn4nnc5ccccc54)CC3)noc2c1] |
| I-95 | 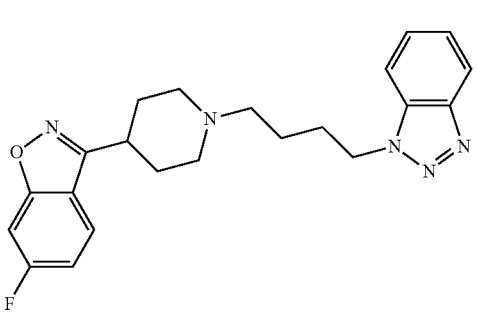 [SMILES: Fc1ccc2c(C3CCN(CCCCn4nnc5ccccc54)CC3)noc2c1] |
| I-96 | 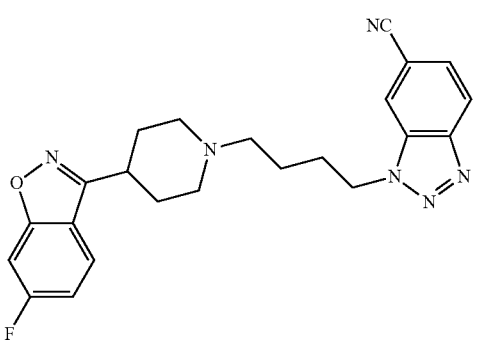 [SMILES: N#Cc1ccc2nnn(CCCCN3CCC(c4noc5cc(F)ccc45)CC3)c2c1] |
| I-97 | 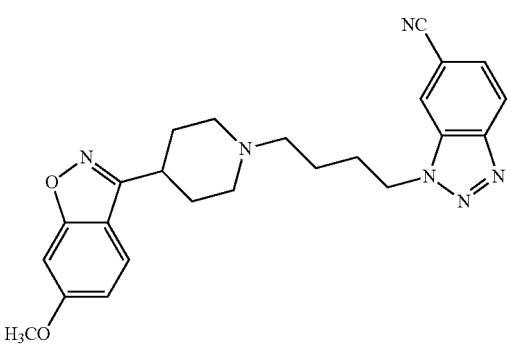 [SMILES: COc1ccc2c(C3CCN(CCCCn4nnc5ccc(C#N)cc54)CC3)noc2c1] |
| I-98 | 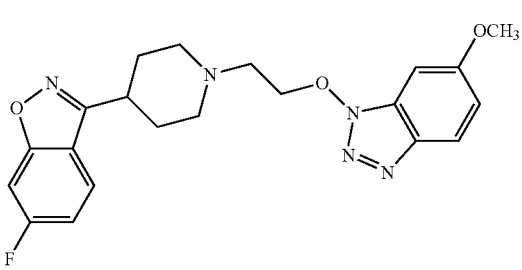 [SMILES: COc1ccc2nnn(OCCN3CCC(c4noc5cc(F)ccc45)CC3)c2c1] |

| Code | Chemical structure |
|---|---|
| I-99 | 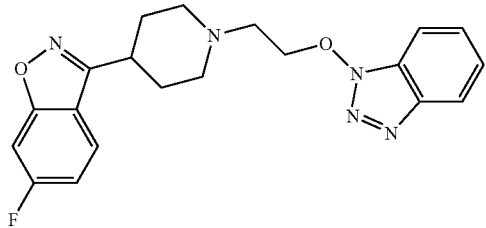 |
| I-100 | 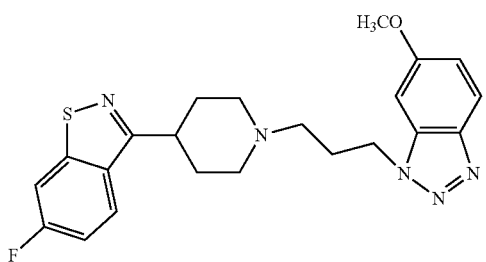 [SMILES: COc1ccc2nnn(CCCN3CCC(c4nsc5cc(F)ccc45)CC3)c2c1] |
| I-101 | 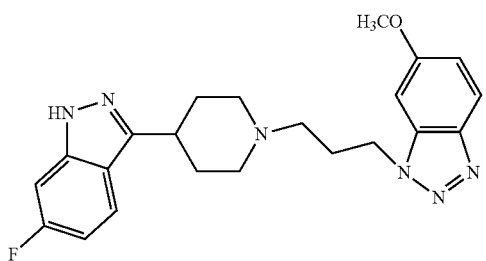 [SMILES: COc1ccc2nnn(CCCN3CCC(c4n[nH]c5cc(F)ccc45)CC3)c2c1] |
| I-102 | 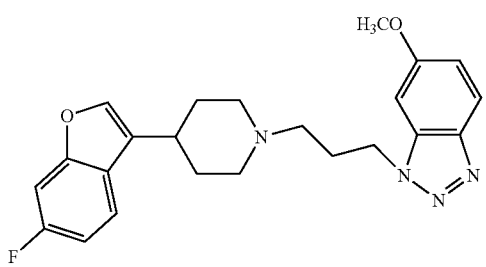 [SMILES: COc1ccc2nnn(CCCN3CCC(c4coc5cc(F)ccc45)CC3)c2c1] |
| I-103 | 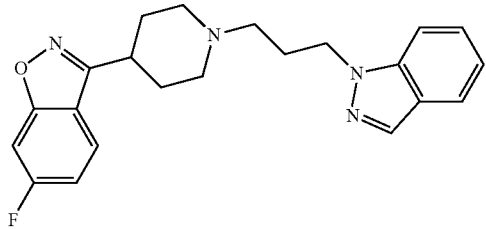 [SMILES: Fc1ccc2c(C3CCN(CCCn4ncc5ccccc54)CC3)noc2c1] |
| I-104 | 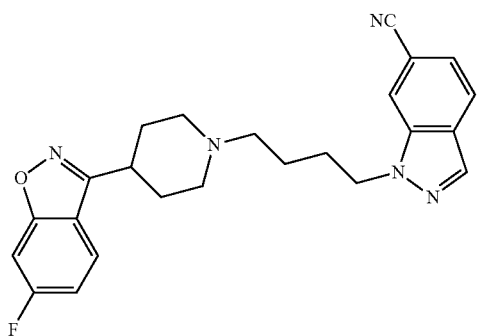 [SMILES: N#Cc1ccc2cnn(CCCCN3CCC(c4noc5cc(F)ccc45)CC3)c2c1] |
| I-105 | 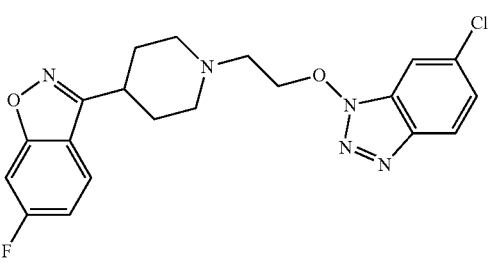 [SMILES: Fc1ccc2c(C3CCN(CCOn4nnc5ccc(Cl)cc54)CC3)noc2c1] |
| I-106 | 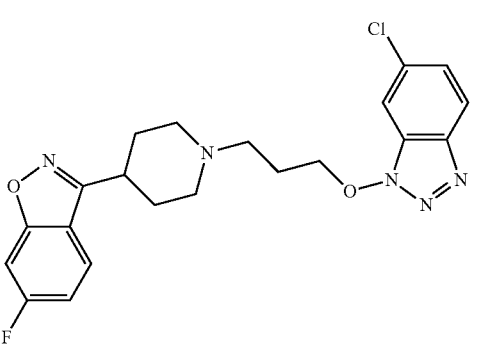 |
| I-107 | 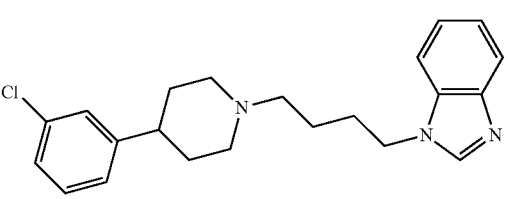 |
| I-108 | 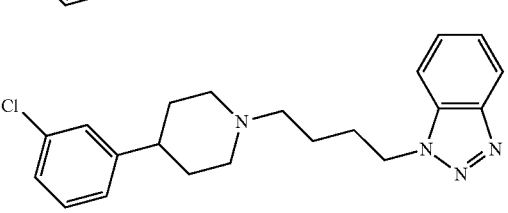 |
| I-109 | 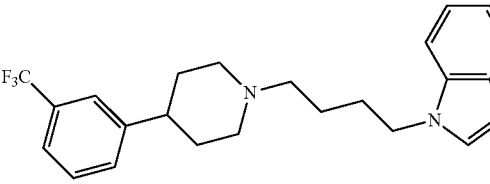 |
| I-110 | 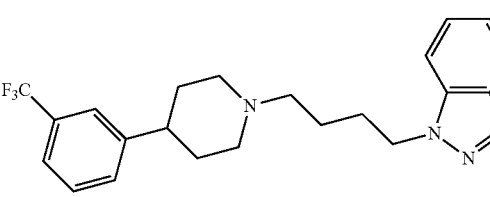 |
| I-111 | 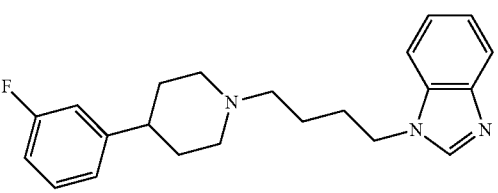 [SMILES: Fc1cccc(C2CCN(CCCCn3cnc4ccccc43)CC2)c1] |

| Code | Chemical structure |
|---|---|
| I-112 | 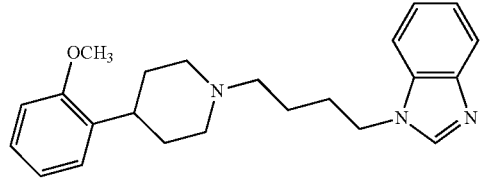 [SMILES: COc1ccccc1C1CCN(CCCCn2cnc3ccccc32)CC1] |
| I-113 | 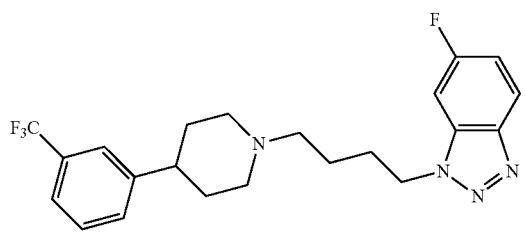 |
| I-114 | 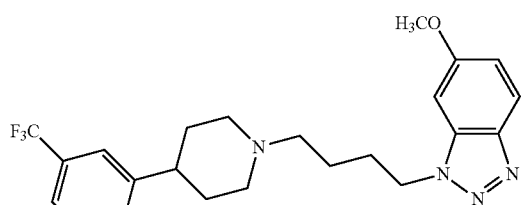 |
| I-115 | 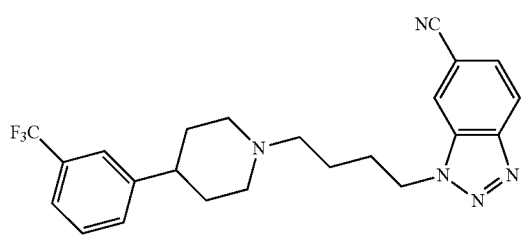 |
| I-116 | 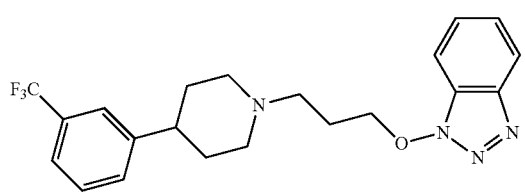 |
| I-117 | 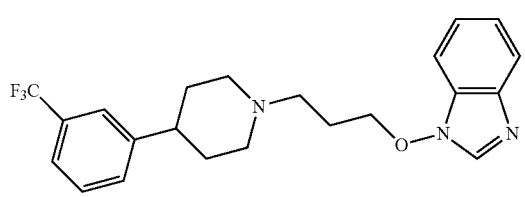 |
| I-118 | 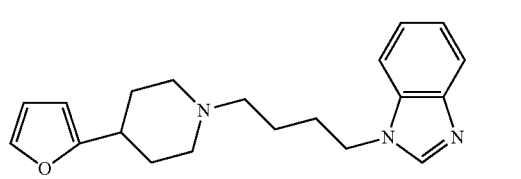 [SMILES: c1coc(C2CCN(CCCCn3cnc4ccccc43)CC2)c1] |
| I-119 | 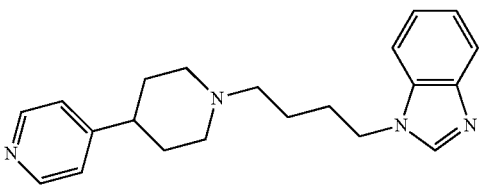 |
| I-120 | 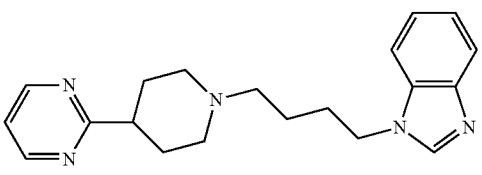 |
| I-121 | 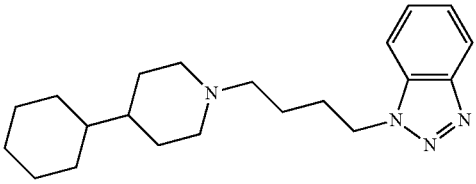 [SMILES: c1ccc2c(c1)nnn2CCCCN1CCC(C2CCCCC2)CC1] |
| I-122 | 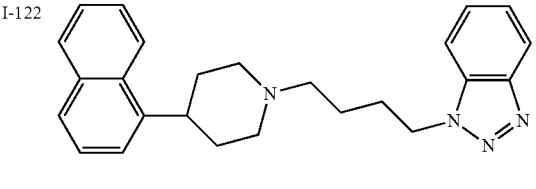 |
| I-123 | 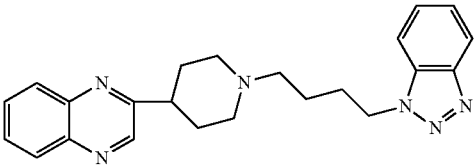 [SMILES: c1ccc2nc(C3CCN(CCCCn4nnc5ccccc54)CC3)cnc2c1] |
| I-124 | 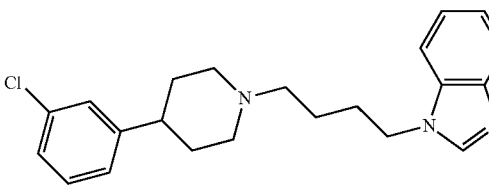 |
| I-125 | 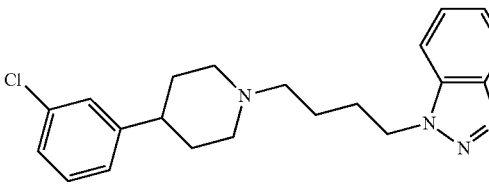 |
| I-126 | 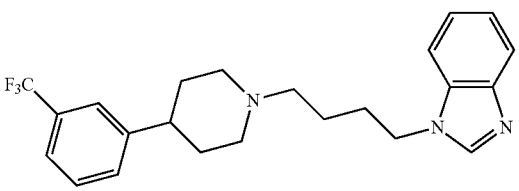 |

| Code | Chemical structure |
|---|---|
| I-127 | 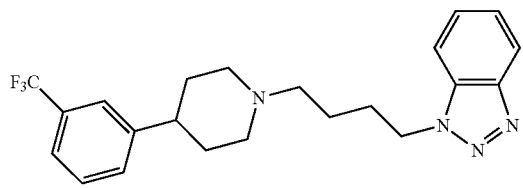 [SMILES: FC(F)(F)c1cccc(C2CCN(CCCCn3nnc4ccccc43)CC2)c1] |
| I-128 | 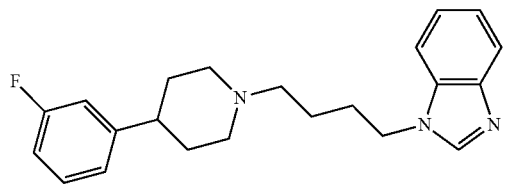 [SMILES: Fc1cccc(C2CCN(CCCCn3cnc4ccccc43)CC2)c1] |
| I-129 | 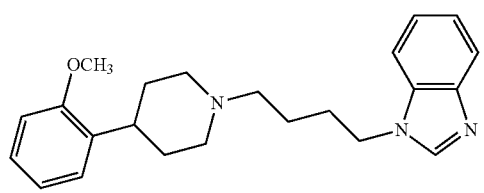 [SMILES: COc1ccccc1C1CCN(CCCCn2cnc3ccccc32)CC1] |
| I-130 | 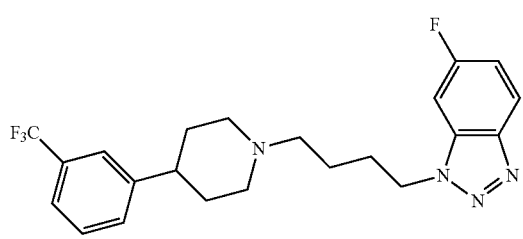 |
| I-131 | 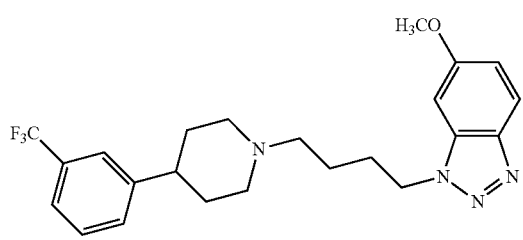 [SMILES: COc1ccc2nnn(CCCCN3CCC(c4cccc(C(F)(F)F)c4)CC3)c2c1] |
| I-132 | 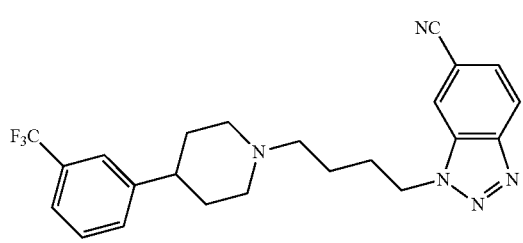 |
| I-133 | 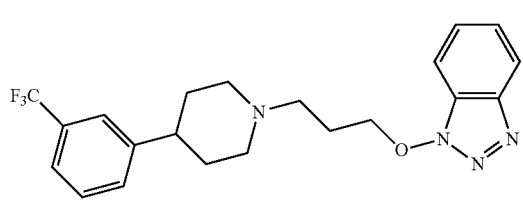 [SMILES: FC(F)(F)c1cccc(C2CCN(CCCOn3nnc4ccccc43)CC2)c1] |
| Code | Chemical structure |
|---|---|
| I-134 | 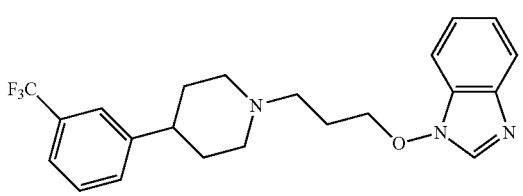 |
| I-135 | 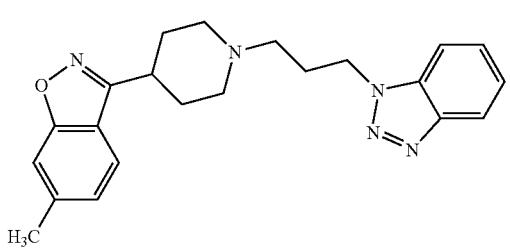 [SMILES: Cc1ccc2c(C3CCN(CCCn4nnc5ccccc54)CC3)noc2c1] |
| I-136 | 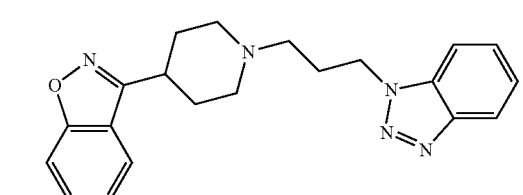 |
| I-137 | 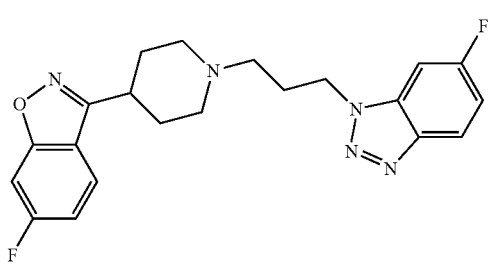 [SMILES: Fc1ccc2c(C3CCN(CCCn4nnc5ccc(F)cc54)CC3)noc2c1] |
| I-138 | 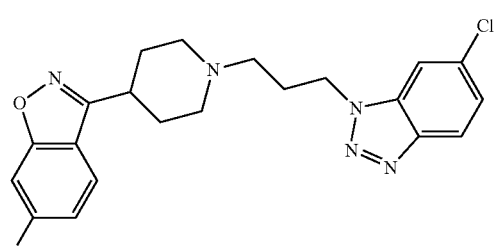 |
| I-139 | 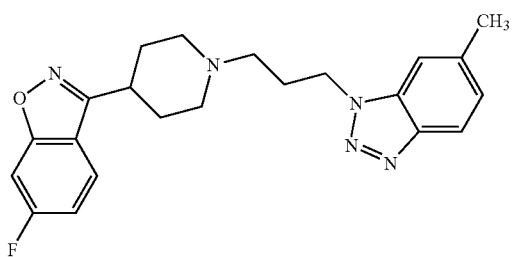 [SMILES: Cc1ccc2nnn(CCCN3CCC(c4noc5cc(F)ccc45)CC3)c2c1] |

| Code | Chemical structure |
|---|---|
| I-140 | 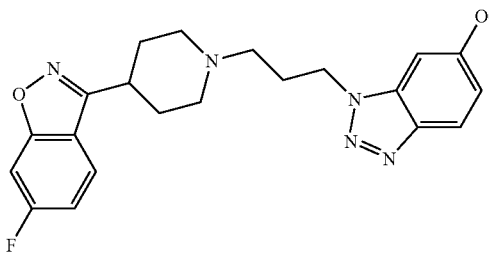 |
| I-141 | 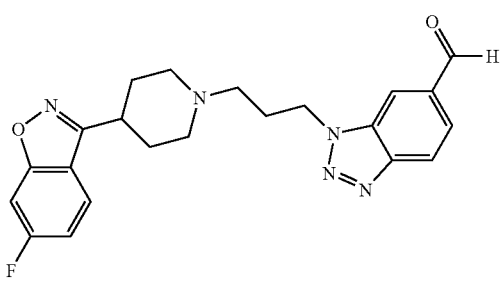 [SMILES: O=Cc1ccc2nnn(CCCN3CCC(c4noc5cc(F)ccc45)CC3)c2c1] |
| I-142 | 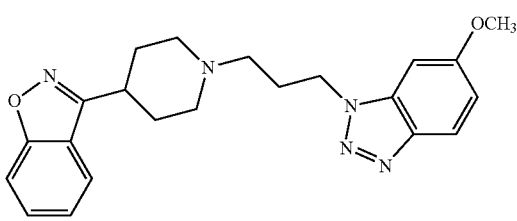 [SMILES: COc1ccc2nnn(CCCN3CCC(c4noc5ccccc45)CC3)c2c1] |
| I-143 | 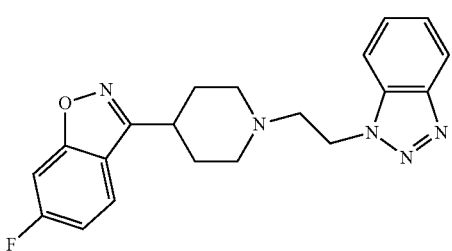 [SMILES: Fc1ccc2c(C3CCN(CCn4nnc5ccccc54)CC3)noc2c1] |
| I-144 | 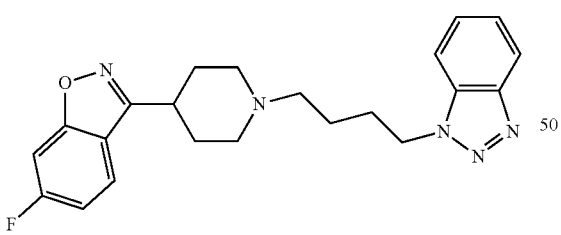 |
| I-145 | 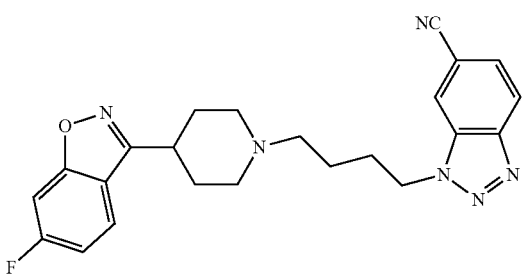 [SMILES: N#Cc1ccc2nnn(CCCCN3CCC(c4noc5cc(F)ccc45)CC3)c2c1] |
| Code | Chemical structure |
|---|---|
| I-146 | 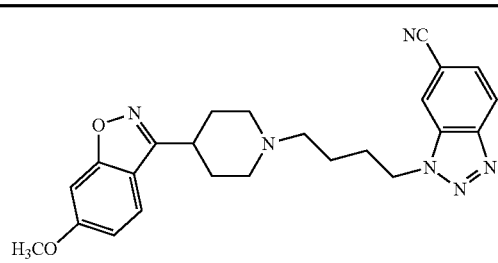 |
| I-147 | 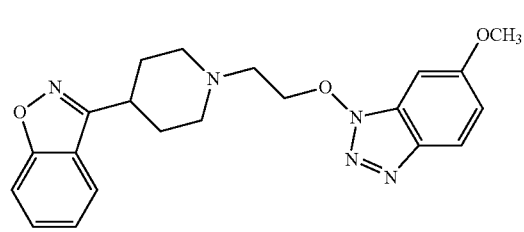 [SMILES: COc1ccc2nnn(OCCN3CCC(c4noc5ccccc45)CC3)c2c1] |
| I-148 | 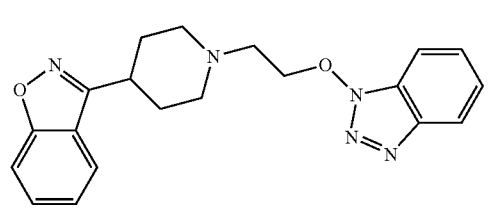 [SMILES: c1ccc2c(c1)nnn2OCCN1CCC(c2noc3ccccc23)CC1] |
| I-149 | 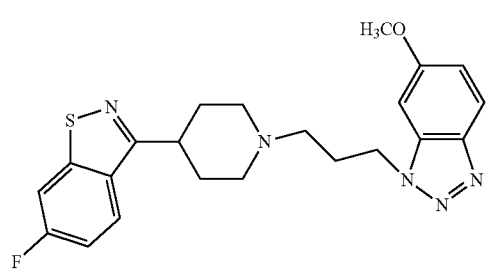 |
| I-150 | 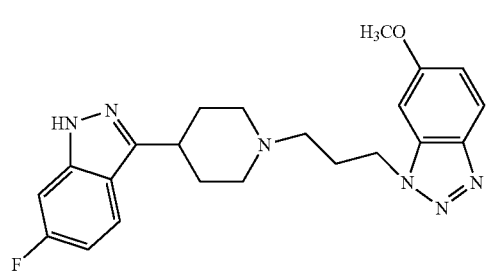 |
| I-151 | 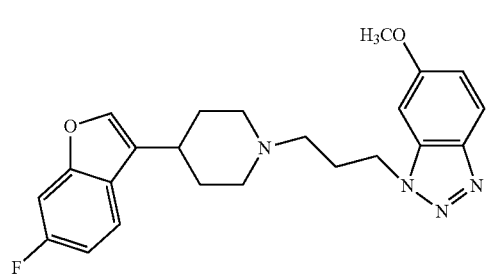 [SMILES: COc1ccc2nnn(CCCN3CCC(c4coc5cc(F)ccc45)CC3)c2c1] |

-continued

| Code | Chemical structure |
|---|---|
| I-152 | 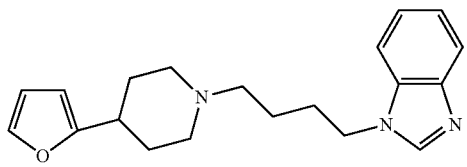 [SMILES: c1coc(C2CCN(CCCCn3cnc4ccccc43)CC2)c1] |
| I-153 | 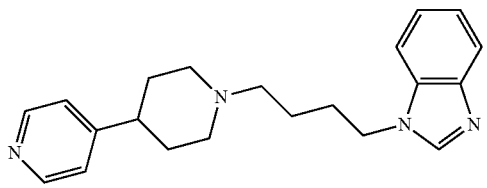 |
| I-154 | 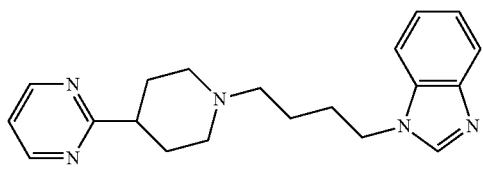 |
| I-155 | 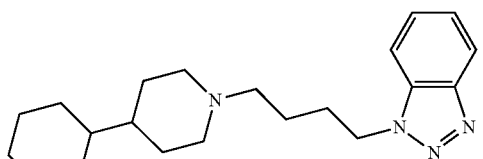 |
| I-156 | 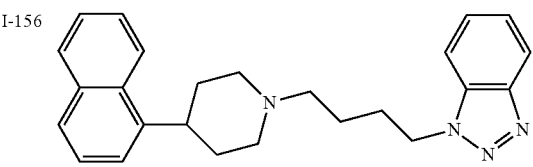 |
| I-157 | 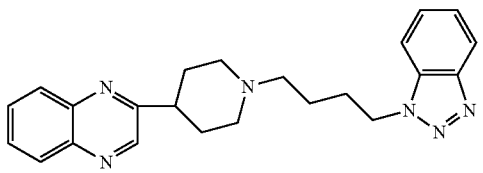 [SMILES: c1ccc2nc(C3CCN(CCCCn4nnc5ccccc54)CC3)cnc2c1] |

The embodiment of this invention prefers the following compounds or their salts acceptable pharmaceutically:

I-1 1-(4-(4-(3-chlorophenyl)piperazine-1-yl)butyl)-1H-benzimidazole,
I-2 1-(4-(4-(3-trifluoromethylphenyl)piperazine-1-yl)butyl)-1H-benzimidazole,
I-3 1-(4-(4-(2,3-dichlorophenyl)piperazine-1-yl)butyl)-1H-benzimidazole,
I-4 1-(4-(4-(2-methoxyphenyl)piperazine-1-yl)butyl)-1H-benzimidazole,
I-5 2-methyl-1-(4-(4-(3-trifluoromethylphenyl)piperazine-1-yl)butyl)-1H-benzimidazole,
I-6 6-fluoro-1-(4-(4-(3-trifluoromethylphenyl)piperazine-1-yl)butyl)-1H-benzimidazole,
I-7 1-(3-(4-phenylpiperazine-1-yl)propyl)-1H-benzimidazole,
I-8 1-(3-(4-(3-fluorophenyl)piperazine-1-yl)propyl)-1H-benzimidazole,
I-9 2-methyl-1-(3-(4-(3-fluorophenyl)piperazine-1-yl)propyl)-1H-benzimidazole,
I-10 1-(4-(4-(3-cyanophenyl)piperazine-1-yl)butyl)-1H-benzimidazole,
I-11 1-(4-(4-(4-methylphenyl)piperazine-1-yl)butyl)-1H-benzimidazole,
I-12 1-(4-(4-(2-furyl)piperazine-1-yl)butyl)-1H-benzimidazole,
I-13 1-(4-(4-(4-pyridyl)piperazine-1-yl)butyl)-1H-benzimidazole,
I-14 1-(4-(4-(2-pyrimidinyl)piperazine-1-yl)butyl)-1H-benzimidazole,
I-15 1-(4-(4-(1-cyclohexyl)piperazine-1-yl)butyl)-1H-benzimidazole,
I-16 1-(4-(4-(1-naphthyl)piperazine-1-yl)butyl)-1H-benzimidazole,
I-17 1-(4-(4-(2-quinoxalinyl)piperazine-1-yl)butyl)-1H-benzimidazole,
I-18 1-(4-(4-(3-(6-fluoro benzisoxazolyl))piperazine-1-yl)butyl)-1H-benzimidazole,
I-19 1-(4-(4-(3-(6-fluoro benzisothiazolyl))piperazine-1-yl)butyl)-1H-benzimidazole,
I-20 1-(4-(4-(3-benzimidazoyl)piperazine-1-yl)butyl)-1H-benzimidazole,
I-21 1-(4-(4-(3-(6-fluoro benzofuranyl))piperazine-1-yl)butyl)-1H-benzimidazole,
I-22 1-(4-(4-(3-(6-fluoro benzisoxazolyl))piperazine-1-yl)butyl)-1H-benzimidazole,
I-23 1-(4-(4-(3-trifluoromethylphenyl)piperazine-1-yl)propoxyl)-1H-benzimidazole,
I-24 1-(4-(4-(3-chlorphenyl)piperazine-1-yl)propoxyl)-1H-benzimidazole,
I-25 6-chloro-1-(4-(4-(3-trifluoromethylphenyl)piperazine-1-yl)butyl)-1H-benzimidazole,
I-26 6-cyano-1-(4-(4-(3-trifluoromethylphenyl)piperazine-1-yl)butyl)-1H-benzimidazole,
I-27 6-methoxycarbonyl-1-(4-(4-(3-trifluoromethylphenyl)piperazine-1-yl)butyl)-1H-benzimidazole,
I-28 2-chloro-1-(5-(4-(3-trifluoromethylphenyl)piperazine-1-yl)pentyl)-1H-benzimidazole,
I-29 1-(4-(4-(3-chlorophenyl)piperazine-1-yl)butyl)-1H-benzotriazole,
I-30 1-(4-(4-(3-fluorophenyl)piperazine-1-yl)butyl)-1H-benzotriazole,
I-31 1-(4-(4-(3-trifluoromethylphenyl)piperazine-1-yl)butyl)-1H-benzotriazole,
I-32 6-fluoro-1-(4-(4-(3-trifluoromethylphenyl)piperazine-1-yl)butyl)-1H-benzotriazole,
I-33 5,6-dimethyl-1-(4-(4-(3-trifluoromethylphenyl)piperazine-1-yl)butyl)-1H-benzotriazole,
I-34 3-(4-(4-(1H-benzotriazole-1-yl)butyl)piperazine-1-yl)benzisothiazolyl,
I-35 3-(4-(4-(1H-benzotriazole-1-yl)butyl)piperazine-1-yl)benzisoxazolyl,
I-36 6-fluoro-3-(4-(4-(1H-benzotriazole-1-yl)butyl)piperazine-1-yl)benzisoxazolyl,
I-37 6-fluoro-3-(4-(3-(1H-benzotriazole-1-yl)propyl)piperazine-1-yl)benzisoxazolyl,
I-38 1-(3-(4-(2,3-dichlorophenyl)piperazine-1-yl)butyl)-1H-benzotriazole,
I-39 1-(3-(4-(3-methylphenyl)piperazine-1-yl)butyl)-1H-benzotriazole,
I-40 1-(4-(4-(3-methoxyphenyl)piperazine-1-yl)butyl)-1H-benzotriazole,
I-41 1-(4-(4-(3-cyanophenyl)piperazine-1-yl)butyl)-1H-benzotriazole,
I-42 1-(5-(4-(3-trifluoromethylphenyl)piperazine-1-yl)pentyl)-1H-benzotriazole, I-43 1-(4-(4-(2-furyl)piperazine-1-yl)butyl)-1H-benzotriazole, I-44 1-(4-(4-(4-pyridyl)piperazine-1-yl)butyl)-1H-benzotriazole, I-45 1-(4-(4-(2-pyrimidinyl)piperazine-1-yl)butyl)-1H-benzotriazole, I-46 1-(4-(4-cyclohexyl piperazine-1-yl)butyl)-1H-benzotriazole, I-47 1-(4-(4-(1-naphthyl)piperazine-1-yl)butyl)-1H-benzotriazole, I-48 1-(4-(4-(2-quinoxalinyl)piperazine-1-yl)butyl)-1H-benzotriazole, I-49 1-(4-(4-(3-(6-fluoro benzisothiazolyl))piperazine-1-yl)butyl)-1H-benzotriazole, I-50 1-(4-(4-(3-benzimidazoyl)piperazine-1-yl)butyl)-1H-benzimidazole, I-51 1-(3-(4-(3-(6-fluoro benzofuranyl))piperazine-1-yl)propyl)-1H-benzotriazole, I-52 1-(4-(4-(3-(6-fluoro benzisoxazolyl)piperazine-1-yl)propoxyl)-1H-benzotriazole, I-53 6-fluoro-1-(4-(4-(3-(6-fluoro-benzisothiazolyl)piperazine-1-yl)propoxyl)-1H-benzotriazole, I-54 6-chloro-1-(4-(4-(3-trifluoromethylphenyl)piperazine-1-yl)butyl)-1H-benzotriazole, I-55 6-cyano-1-(4-(4-(3-trifluoromethylphenyl)piperazine-1-yl)butyl)-1H-benzotriazole, I-56 6-methoxycarbonyl-1-(4-(4-(3-trifluoromethylphenyl)piperazine-1-yl)butyl)-1H-benzotriazole, I-57 1-(4-(4-(3-trifluoromethylphenyl)piperazine-1-yl)butyl)-1H-indole, I-58 6-cyano-1-(4-(4-(3-chlorophenyl)piperazine-1-yl)butyl)-1H-indole, I-59 1-(3-(4-(3-trifluoromethylphenyl)piperazine-1-yl)propyl)-1H-benzopyrazole, I-60 6-cyano-1-(3-(4-(2,3-fluorophenyl)piperazine-1-yl)propyl)-1H-benzopyrazole, I-84 N-(3-(1H-benzotriazole-1-yl)propyl)-4-(3-benzisoxazolyl)piperidine, I-85 N-(3-(1H-benzotriazole-1-yl)propyl)4-(3-(6-fluoro benzisoxazolyl))piperidine, I-86 N-(3-(1H-benzotriazole-1-yl)propyl)4-(3-(6-methyl benzisoxazolyl))piperidine, I-87 N-(3-(1H-benzotriazole-1-yl)propyl)4-(3-(6-methoxyl benzisoxazolyl))piperidine, I-88 N-(3-(6-fluoro-1H-benzotriazole-1-yl)propyl)-4-(3-(6-fluoro benzisoxazolyl))piperidine, I-89 N-(3-(6-chloro-1H-benzotriazole-1-yl)propyl)-4-(3-(6-fluoro benzisoxazolyl))piperidine, I-90 N-(3-(6-methyl-1H-benzotriazole-1-yl)propyl)-4-(3-(6-fluoro benzisoxazolyl))piperidine, I-91 N-(3-(6-methoxyl-1H-benzotriazole-1-yl)propyl)-4-(3-(6-fluoro benzisoxazolyl))piperidine, I-92 N-(3-(6-formoxyl-1H-benzotriazole-1-yl)propyl)4-(3-(6-fluoro benzisoxazolyl))piperidine, I-93 N-(3-(6-methoxyl benzotriazolyl)propyl)-4-(3-benzisoxazolyl)piperidine, I-94 N-(2-(1-benzotriazolyl)ethyl)-4-(3-(6-fluoro benzisoxazolyl))piperidine, I-95 N-(4-(1-benzotriazolyl)butyl)-4-(3-(6-fluoro benzisoxazolyl))piperidine, I-96 N-(4-(6-cyano benzotriazolyl)butyl)-4-(3-(6-fluoro benzisoxazolyl))piperidine, I-97 N-(4-(6-cyano benzotriazolyl)butyl)-4-(3-(6-methoxyl benzisoxazolyl))piperidine, I-103 N-(3-(1-benzopyrazol)propyl)-4-(3-(6-fluoro benzisoxazolyl))piperidine, I-104 N-(4-(6-cyano benzopyrazol)butyl)-4-(3-(6-fluoro benzisoxazolyl))piperidine, I-105 N-(2-(6-fluoro benzotriazolyl)ethoxyl)-4-(3-(6-fluoro benzisoxazolyl))piperidine, I-106 N-(3-(6-fluoro benzotriazolyl)propoxyl)-4-(3-(6-fluoro benzisoxazolyl))piperidine, I-107 N-(4-(1H-benzimidazoyl-1-yl)butyl)-4-(3-chlorophenyl)piperidine, I-108 N-(4-(1H-benzotriazole-1-yl)butyl)-4-(3-chlorophenyl)piperidine, I-109 N-(4-(1H-benzimidazoyl-1-yl)butyl)-4-(3-trifluoromethylphenyl)piperidine, I-110 N-(4-(1H-benzotriazole-1-yl)butyl)-4-(3-trifluoromethylphenyl)piperidine, I-113 N-(4-(6-fluoro-1H-benzotriazole-1-yl)butyl)-4-(3-trifluoromethylphenyl)piperidine, I-116 N-(4-(1H-benzotriazole-1-yl)propoxyl)-4-(3-trifluoromethylphenyl)piperidine, I-117 N-(4-(1H-benzimidazole-1-yl)propoxyl)-4-(3-trifluoromethylphenyl)piperidine, I-124 N-(4-(1H-benzimidazoyl-1-yl)butyl)-4-(3-chlorophenyl)piperidine, I-125 N-(4-(1H-benzotriazole-1-yl)butyl)-4-(3-chlorophenyl)piperidine, I-126 N-(4-(1H-benzimidazoyl-1-yl)butyl)-4-(3-trifluoromethylphenyl)piperidine, I-127 N-(4-(1H-benzotriazole-1-yl)butyl)-4-(3-trifluoromethylphenyl)piperidine, I-130 N-(4-(6-fluoro-1H-benzotriazole-1-yl)butyl)-4-(3-trifluoromethylphenyl)piperidine, I-133 N-(4-(1H-benzotriazole-1-yl)propoxyl)-4-(3-trifluoromethylphenyl)piperidine, I-134 N-(4-(1H-benzimidazole-1-yl)propoxyl)-4-(3-trifluoromethylphenyl)piperidine, I-135 N-(3-(1H-benzotriazole-1-yl)propyl)-4-(3-(6-methyl benzisoxazolyl))piperidine, I-136 N-(3-(1H-benzotriazole-1-yl)propyl)-4-(3-(6-methoxyl benzisoxazolyl))piperidine, I-137 N-(3-(6-fluoro-1H-benzotriazole-1-yl)propyl)-4-(3-(6-fluoro benzisoxazolyl))piperidine, I-138 N-(3-(6-chloro-1H-benzotriazole-1-yl)propyl)-4-(3-(6-fluoro benzisoxazolyl))piperidine, I-139 N-(3-(6-methyl-1H-benzotriazole-1-yl)propyl)-4-(3-(6-fluoro benzisoxazolyl))piperidine, I-140 N-(3-(6-methoxyl-1H-benzotriazole-1-yl)propyl)-4-(3-(6-fluoro benzisoxazolyl))piperidine, I-141 N-(3-(6-formoxyl-1H-benzotriazole-1-yl)propyl)-4-(3-(6-fluoro benzisoxazolyl))piperidine, I-142 N-(3-(6-methoxyl benzotriazolyl)propyl)-4-(3-benzisoxazolyl)piperidine, I-143 N-(2-(1-benzotriazolyl)ethyl)-4-(3-(6-fluoro benzisoxazolyl))piperidine, I-144 N-(4-(1-benzotriazolyl)butyl)-4-(3-(6-fluoro benzisoxazolyl))piperidine, I-145 N-(4-(6-cyano benzotriazolyl)butyl)-4-(3-(6-fluoro benzisoxazolyl))piperidine, I-146 N-(4-(6-cyano benzotriazolyl)butyl)-4-(3-(6-methoxyl benzisoxazolyl))piperidine.

The embodiment of this invention further prefers the following benzo five-membered nitrogen heterocyclic compounds or their salts acceptable pharmaceutically:

I-1 1-(4-(4-(3-chlorophenyl)piperazine-1-yl)butyl)-1H-benzimidazole,

I-2 1-(4-(4-(3-trifluoromethylphenyl)piperazine-1-yl)butyl)-1H-benzimidazole,

I-3 1-(4-(4-(2,3-dichlorophenyl)piperazine-1-yl)butyl)-1H-benzimidazole,

I-4 1-(4-(4-(2-methoxyphenyl)piperazine-1-yl)butyl)-1H-benzimidazole,
I-5 2-methyl-1-(4-(4-(3-trifluoromethylphenyl)piperazine-1-yl)butyl)-1H-benzimidazole,
I-6 6-fluoro-1-(4-(4-(3-trifluoromethylphenyl)piperazine-1-yl)butyl)-1H-benzimidazole,
I-8 1-(3-(4-(3-fluorophenyl)piperazine-1-yl)propyl)-1H-benzimidazole,
I-13 1-(4-(4-(4-pyridyl)piperazine-1-yl)butyl)-1H-benzimidazole,
I-15 1-(4-(4-(1-cyclohexyl)piperazine-1-yl)butyl)-1H-benzimidazole,
I-17 1-(4-(4-(2-quinoxalinyl)piperazine-1-yl)butyl)-1H-benzimidazole,
I-18 1-(4-(4-(3-(6-fluoro benzisoxazolyl))piperazine-1-yl)butyl)-1H-benzimidazole,
I-22 1-(4-(4-(3-(6-fluoro benzisoxazolyl))piperazine-1-yl)butyl)-1H-benzimidazole,
I-23 1-(4-(4-(3-trifluoromethylphenyl)piperazine-1-yl)propoxyl)-1H-benzimidazole,
I-24 1-(4-(4-(3-chlorphenyl)piperazine-1-yl)propoxyl)-1H-benzimidazole,
I-25 6-chloro-1-(4-(4-(3-trifluoromethylphenyl)piperazine-1-yl)butyl)-1H-benzimidazole,
I-29 1-(4-(4-(3-chlorophenyl)piperazine-1-yl)butyl)-1H-benzotriazole,
I-30 1-(4-(4-(3-fluorophenyl)piperazine-1-yl)butyl)-1H-benzotriazole,
I-31 1-(4-(4-(3-trifluoromethylphenyl)piperazine-1-yl)butyl)-1H-benzotriazole,
I-32 6-fluoro-1-(4-(4-(3-trifluoromethylphenyl)piperazine-1-yl)butyl)-1H-benzotriazole,
I-34 3-(4-(4-(1H-benzotriazole-1-yl)butyl)piperazine-1-yl)benzisothiazolyl,
I-35 3-(4-(4-(1H-benzotriazole-1-yl)butyl)piperazine-1-yl)benzisoxazolyl,
I-36 6-fluoro-3-(4-(4-(1H-benzotriazole-1-yl)butyl)piperazine-1-yl)benzisoxazolyl,
I-37 6-fluoro-3-(4-(3-(1H-benzotriazole-1-yl)propyl)piperazine-1-yl)benzisoxazolyl,
I-38 1-(3-(4-(2,3-dichlorophenyl)piperazine-1-yl)butyl)-1H-benzotriazole,
I-39 1-(3-(4-(3-methylphenyl)piperazine-1-yl)butyl)-1H-benzotriazole,
I-40 1-(4-(4-(3-methoxyphenyl)piperazine-1-yl)butyl)-1H-benzotriazole,
I-41 1-(4-(4-(3-cyanophenyl)piperazine-1-yl)butyl)-1H-benzotriazole,
I-51 1-(3-(4-(3-(6-fluoro benzofuranyl))piperazine-1-yl)propyl)-1H-benzotriazole,
I-52 1-(4-(4-(3-(6-fluoro benzisoxazolyl)piperazine-1-yl)propoxyl)-1H-benzotriazole,
I-54 6-chloro-1-(4-(4-(3-trifluoromethylphenyl)piperazine-1-yl)butyl)-1H-benzotriazole,
I-59 1-(3-(4-(3-trifluoromethylphenyl)piperazine-1-yl)propyl)-1H-benzopyrazole.

The embodiment of this invention particularly prefers the following benzo five-membered nitrogen heterocyclic compounds or their salts acceptable pharmaceutically:

I-1 1-(4-(4-(3-chlorophenyl)piperazine-1-yl)butyl)-1H-benzimidazole,
I-2 1-(4-(4-(3-trifluoromethylphenyl)piperazine-1-yl)butyl)-1H-benzimidazole,
I-3 1-(4-(4-(2,3-dichlorophenyl)piperazine-1-yl)butyl)-1H-benzimidazole,
I-29 1-(4-(4-(3-chlorophenyl)piperazine-1-yl)butyl)-1H-benzotriazole,
I-30 1-(4-(4-(3-fluorophenyl)piperazine-1-yl)butyl)-1H-benzotriazole,
I-31 1-(4-(4-(3-trifluoromethylphenyl)piperazine-1-yl)butyl)-1H-benzotriazole,
I-34 3-(4-(4-(1H-benzotriazole-1-yl)butyl)piperazine-1-yl)benzisothiazolyl,
I-36 6-fluoro-3-(4-(4-(1H-benzotriazole-1-yl)butyl)piperazine-1-yl)benzisoxazolyl,
I-37 6-fluoro-3-(4-(3-(1H-benzotriazole-1-yl)propyl)piperazine-1-yl)benzisoxazolyl,
I-38 1-(3-(4-(2,3-dichlorophenyl)piperazine-1-yl)butyl)-1H-benzotriazole,
I-39 1-(3-(4-(3-methylphenyl)piperazine-1-yl)butyl)-1H-benzotriazole,
I-40 1-(4-(4-(3-methoxyphenyl)piperazine-1-yl)butyl)-1H-benzotriazole.

The embodiment of this invention particularly prefers the following compounds or their salts acceptable pharmaceutically:

I-3 1-(4-(4-(2,3-dichlorophenyl)piperazine-1-yl)butyl)-1H-benzimidazole,
I-29 1-(4-(4-(3-chlorophenyl)piperazine-1-yl)butyl)-1H-benzotriazole,
I-31 1-(4-(4-(3-trifluoromethylphenyl)piperazine-1-yl)butyl)-1H-benzotriazole,
I-34 3-(4-(4-(1H-benzotriazole-1-yl)butyl)piperazine-1-yl)benzisothiazolyl,
I-84 N-(3-(1H-benzotriazole-1-yl)propyl)-4-(3-benzisoxazolyl)piperidine,
I-85 N-(3-(1H-benzotriazole-1-yl)propyl)4-(3-(6-fluoro benzisoxazolyl))piperidine,
I-93 N-(3-(6-methoxyl benzotriazolyl)propyl)-4-(3-benzisoxazolyl)piperidine,
I-109 N-(4-(1H-benzimidazoyl-1-yl)butyl)-4-(3-trifluoromethylphenyl)piperidine,
I-110 N-(4-(1H-benzotriazole-1-yl)butyl)-4-(3-trifluoromethylphenyl)piperidine,
I-126 N-(4-(1H-benzimidazoyl-1-yl)butyl)-4-(3-trifluoromethylphenyl)piperidine,
I-127 N-(4-(1H-benzotriazole-1-yl)butyl)-4-(3-trifluoromethylphenyl)piperidine,
I-142 N-(3-(6-methoxyl benzotriazolyl)propyl)-4-(3-benzisoxazolyl)piperidine.

As used herein, for compound in formula (I) of this invention, the pharmaceutically acceptable salt preferably indicates hydrochlorate, hydrobromide, sulphate, triflutate, mesylate, tartrate, malate, succinate, maleate, citrate, phosphate, lactate, pyruvate, acetate, fumarate, oxaloacetate, esylate, oxalate, benzene sulfonate or isethionate. As used herein, pharmaceutically acceptable salts preferably indicate salts with crystal water, more preferably salts with 0.5-3 molecules of crystal water.

In an embodiment of this invention, especially the preferable compound I-2 and its pharmaceutically acceptable salts, e.g., hydrochlorate, i.e., compound II-2. The corresponding chemical structure is illustrated as II-2.

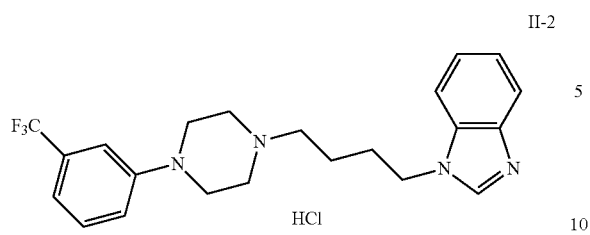

II-2

Hydrochlorate is preferred for salt of compound I-3, i.e., compound II-3. The corresponding chemical structure is illustrated as II-3.

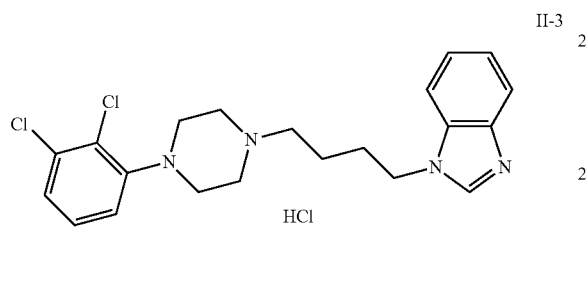

II-3

Of which compound I-29 is a preferable hydrochlorate, i.e., compound II-29. The corresponding chemical structure is illustrated as II-3.

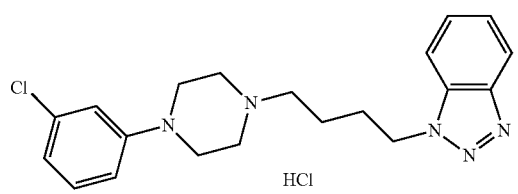

II-29

Hydrochlorate is preferred for salt of compound I-31, i.e., compound II-31. The corresponding chemical structure is illustrated as II-31.

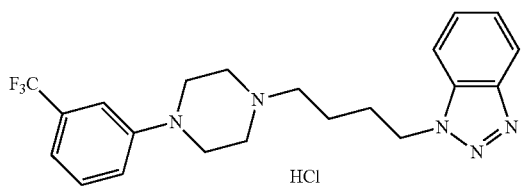

II-31

Hydrochlorate is preferred for salt of compound I-34, i.e., compound II-34. The corresponding chemical structure is illustrated as II-34.

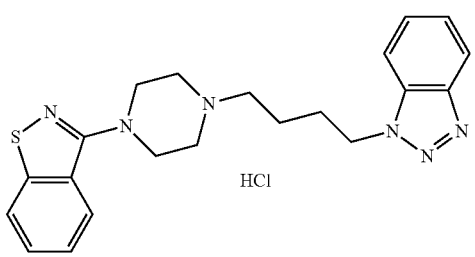

II-34

In an embodiment of this invention, especially the preferable compound I-85 and its pharmaceutically acceptable salts, e.g., hydrochlorate, i.e., compound II-85. The corresponding chemical structure is illustrated as follows.

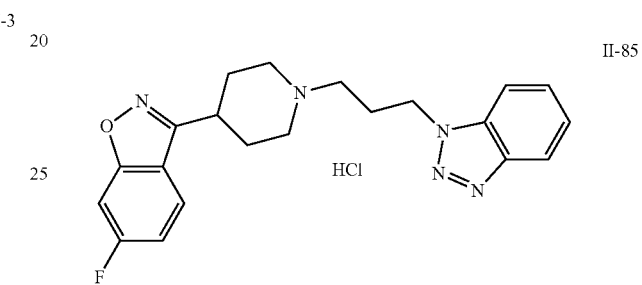

II-85

Figure 2:
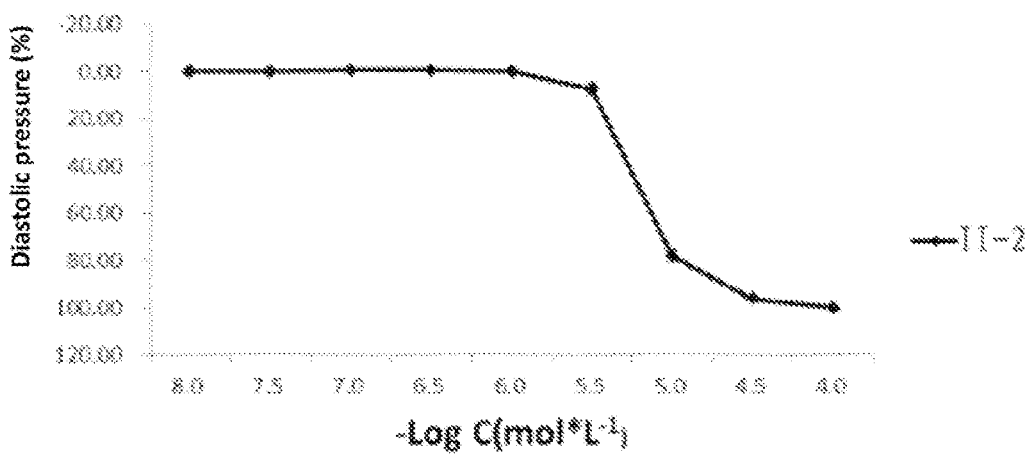
FIG. 2 illustrates the accumulated concentration effect curve of vasodilative effects of compound II-2 ($10^{-8}$-$10^{-4}$ mol·$L^{-1}$) versus vasoconstrictive effects of high potassium concentration (60 mmol·$L^{-1}$) on excised blood vessels from rabbits.
Figure 3:
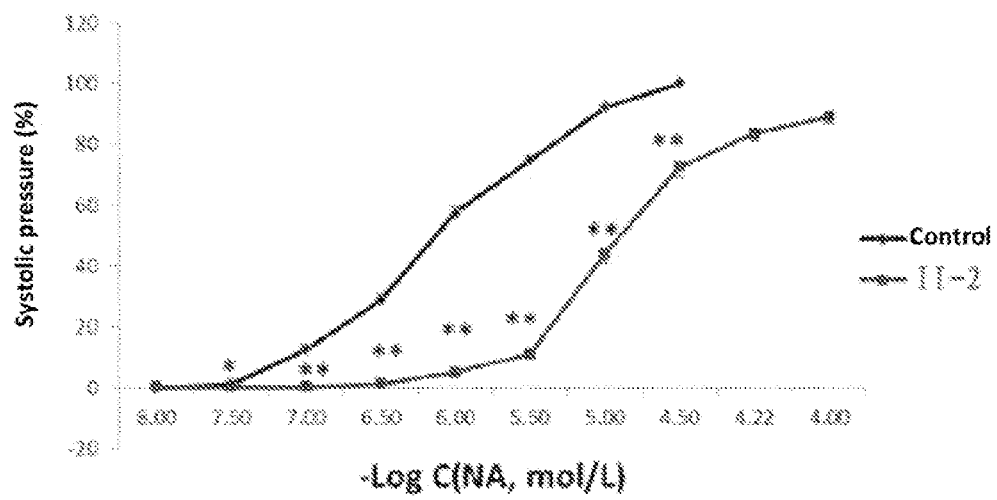
FIG. 3 illustrates the accumulated concentration effect curve of resistance of compound II-2 ($3 \times 10^{-7}$ mol/L) to vasoconstrictive effects of noradrenaline NA ($10^{-8}$-$10^{-4}$ mol/L) on excised blood vessels from rabbits.
Figure 4:
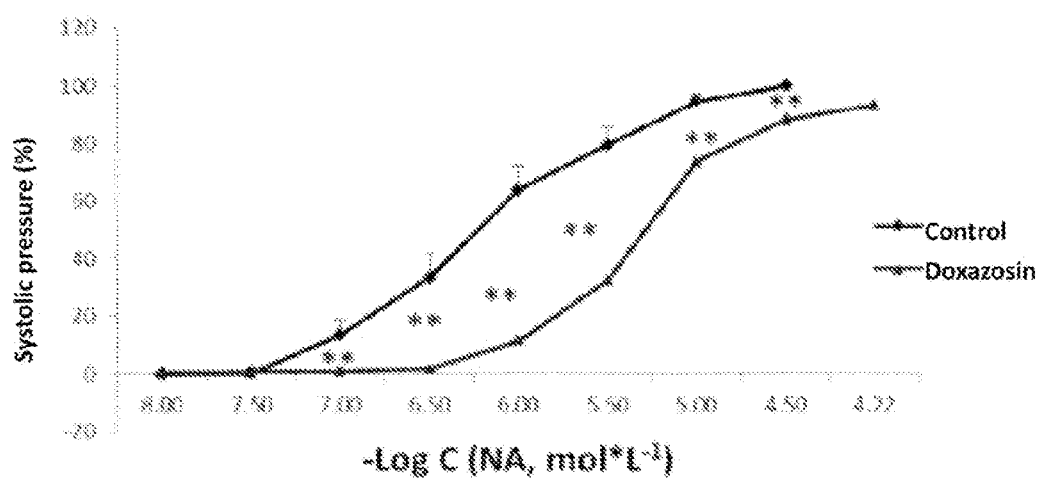
FIG. 4 illustrates the accumulated concentration effect curve of resistance of positive reference drug doxazosin ($10^{-7}$ mol/L) to vasoconstrictive effects of noradrenaline NA ($10^{-8}$-$6 \times 10^{-5}$ mol/L) on excised blood vessels from rabbits.
Figure 5:
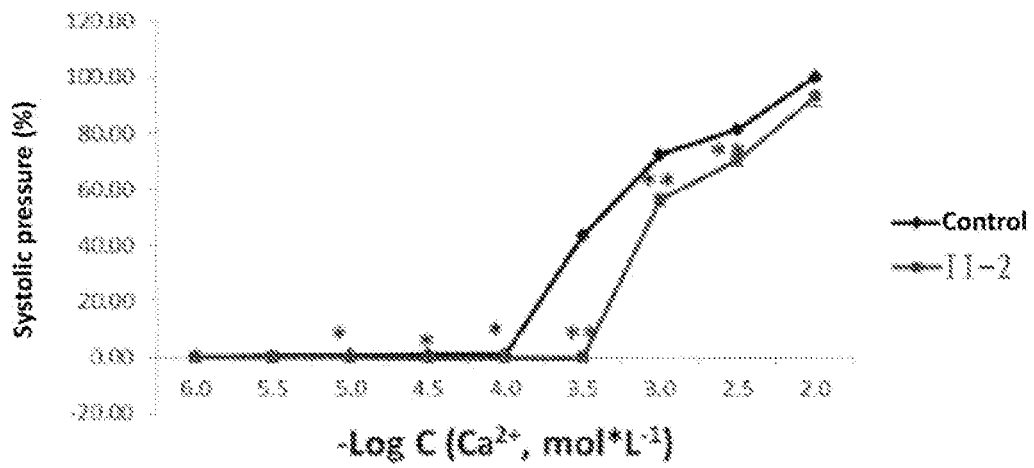
FIG. 5 illustrates the accumulated concentration effect curve of resistance of compound II-2 ($10^{-6}$ mol/L) to vasoconstrictive effects of $CaCl_2$ ($10^{-6}$-$10^{-2}$ mol/L) on excised blood vessels from rabbits.
Figure 6:
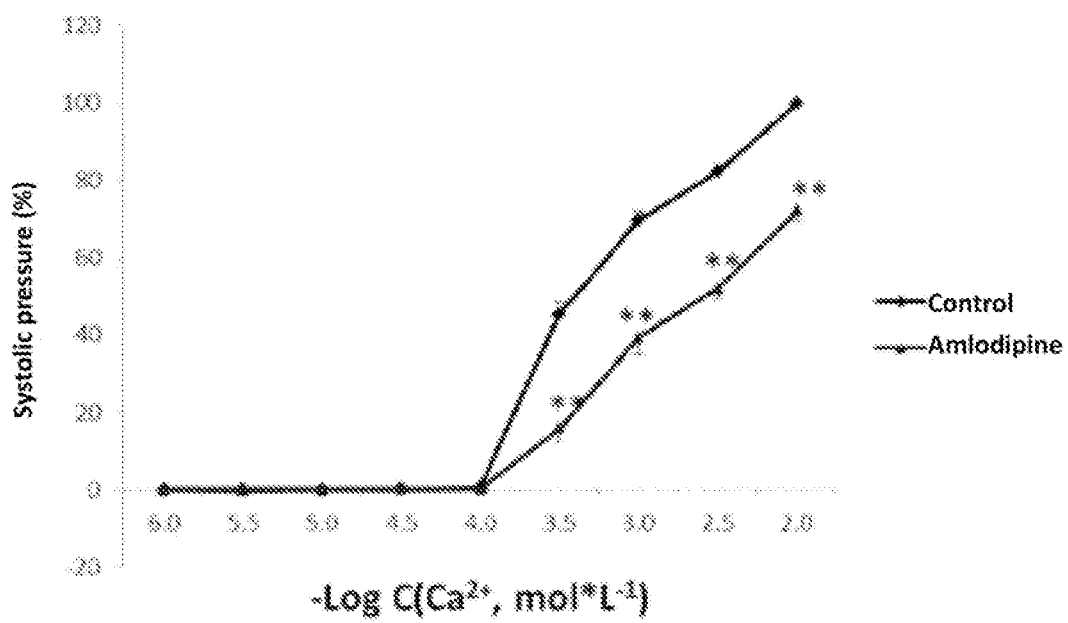
FIG. 6 illustrates the accumulated concentration effect curve of resistance of amlodipine ($10^{-7}$ mol/L) to vasoconstrictive effects of $CaCl_2$ ($10^{-6}$-$10^{-2}$ mol/L) on excised blood vessels from rabbits.
Figure 7:
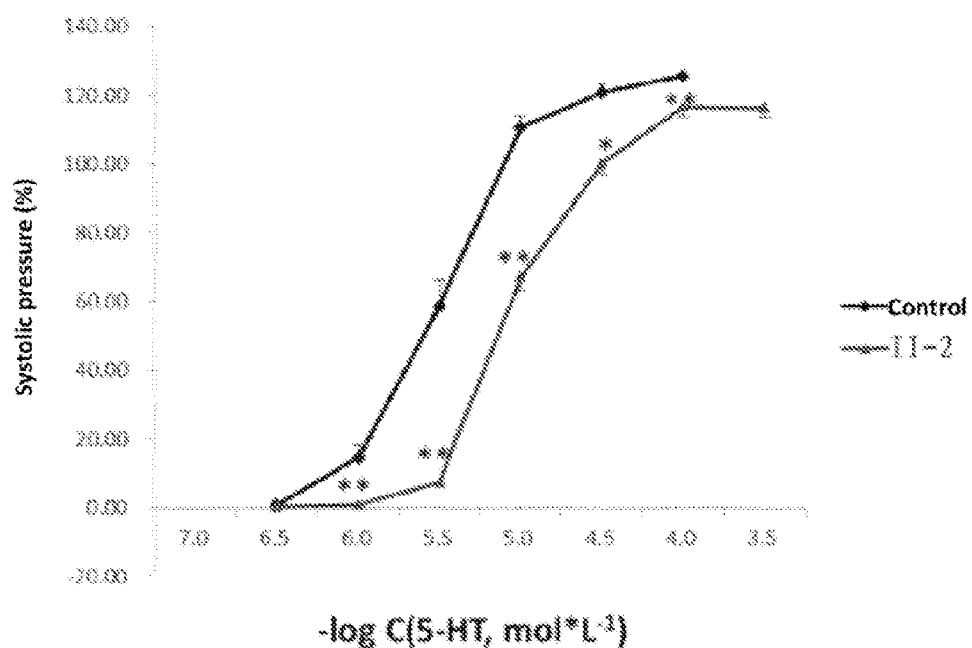
FIG. 7 illustrates the accumulated concentration effect curve of resistance of compound II-2 ($3 \times 10^{-6}$ mol/L) to vasoconstrictive effects of 5-hydroxytryptamine ($10^{-7}$-$3 \times 10^{-4}$ mol/L) on excised blood vessels from rabbits.
Figure 8:
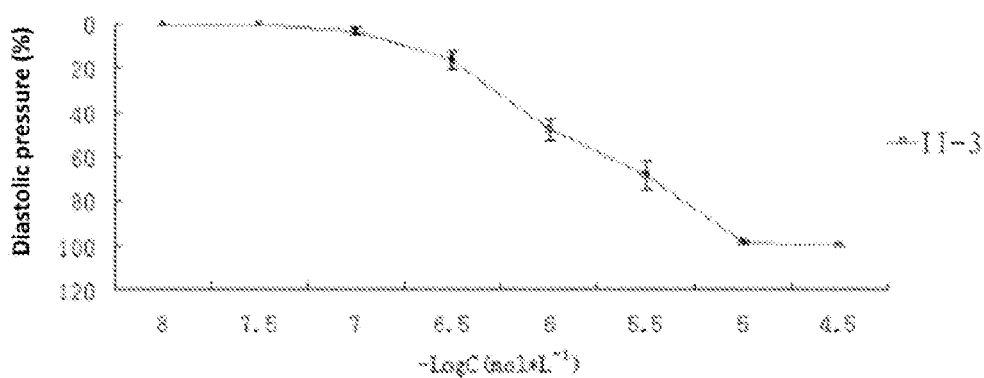
FIG. 8 illustrates the accumulated concentration effect curve of vasodilative effects of compound II-3 ($10^{-8}$-$3 \times 10^{-5}$ mol·$L^{-1}$) versus vasoconstrictive effects of adrenaline ($10^{-5}$ mol·$L^{-1}$) on excised blood vessels from rabbits.
Figure 9:
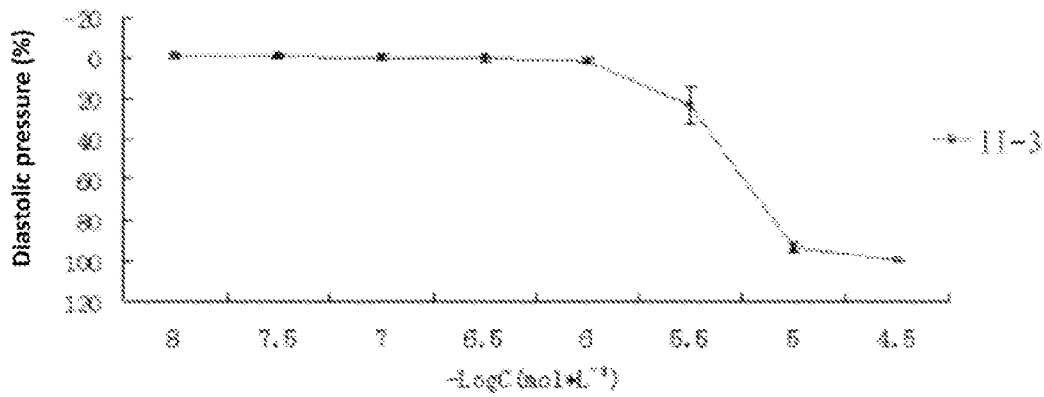
FIG. 9 illustrates the accumulated concentration effect curve of vasodilative effects of compound II-3 ($10^{-8}$-$3 \times 10^{-5}$ mol·$L^{-1}$) versus vasoconstrictive effects of high potassium concentration (60 mmol·$L^{-1}$) on excised blood vessels from rabbits.

In vitro animal experiment suggested that, compound II-2 could relax vascular smooth muscles constricted by adrenaline and high potassium concentration, with $-\log EC_{50}$ values of relaxation of 5.73±0.03 and 5.34±0.02, respectively (FIG. 1 and FIG. 2). Compound II-3 could relax vascular smooth muscles constricted by adrenaline and high potassium concentration, with $-\log EC_{50}$ values of relaxation of 6.01±0.05 and 5.49±0.05, respectively (FIG. 8 and FIG. 9).

It was indicated in a study on dilating mechanism of compound II-2 on vascular smooth muscle that, the compound could competitively resist the vasoconstrictive effects of noradrenaline, calcium ions and hydroxytryptamine, move the dose effect curve of above said agonist transversally to right, while maximal response was not reduced, suggesting that $PA_2$ values for the compound to resist vasoconstrictive effects of noradrenaline (NA), calcium ions and hydroxytryptamine (5-HT) were 7.37±0.08 (7.52±0.04 for doxazosin), 5.61±0.04 (6.99±0.05 for amlodipine) and 5.71±0.08 (FIGS. 3, 4, 5, 6 and 7). The results indicated that, compound II-2 produced vasodilative effects by blocking $\alpha_1$ receptor, $Ca^{2+}$ ion channel and vascular $5-HT_{2A}$ receptor.

Figure 10:
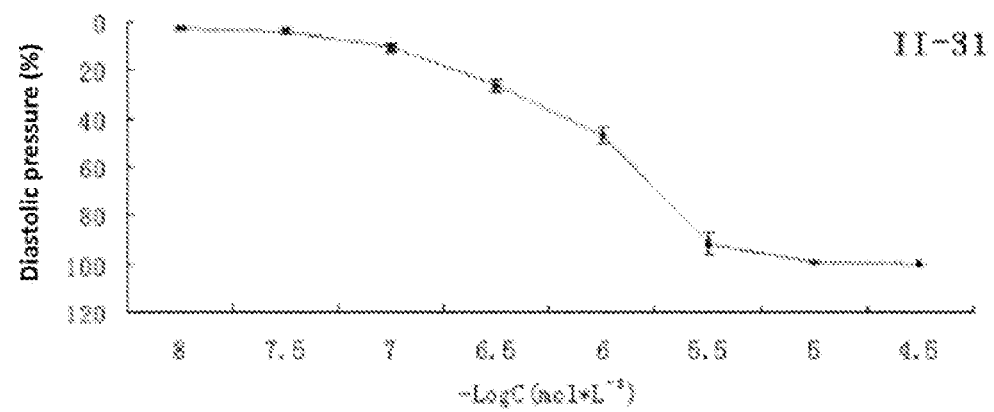
FIG. 10 illustrates the accumulated concentration effect curve of vasodilative effects of compound II-31 ($10^{-8}$-$10^{-5}$ mol·$L^{-1}$) versus vasoconstrictive effects of adrenaline AD ($10^{-5}$ mol·$L^{-1}$) on excised blood vessels from rabbits.
Figure 11:
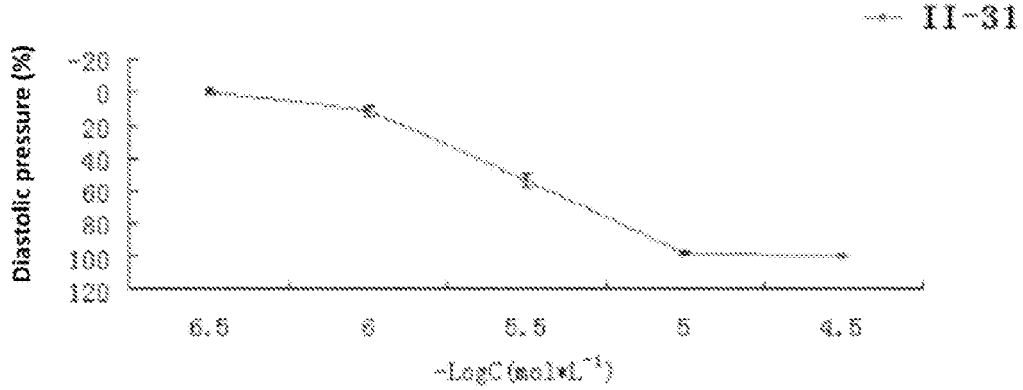
FIG. 11 illustrates the accumulated concentration effect curve of vasodilative effects of compound II-31 ($3 \times 10^{-7}$-$3 \times 10^{-5}$ mol·L$^{-1}$) versus vasoconstrictive effects of high potassium concentration (60 mmol·L$^{-1}$) on excised blood vessels from rabbits.
Figure 15:
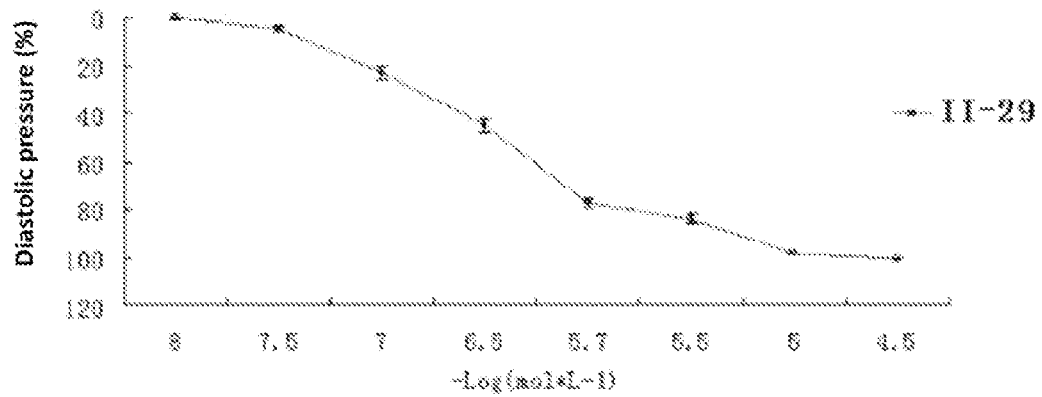
FIG. 15 illustrates the accumulated concentration effect curve of vasodilative effects of compound II-29 ($10^{-8}$-$3 \times 10^{-5}$ mol·L$^{-1}$) versus vasoconstrictive effects of adrenaline AD ($10^{-5}$ mol·L$^{-1}$) on excised blood vessels from rabbits.
Figure 16:
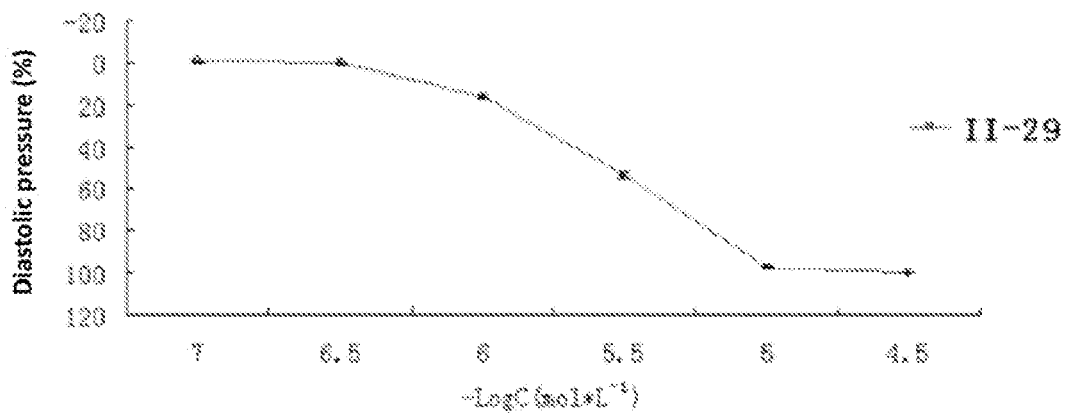
FIG. 16 illustrates the accumulated concentration effect curve of vasodilative effects of compound II-29 ($10^{-7}$-$3 \times 10^{-5}$ mol·L$^{-1}$) versus vasoconstrictive effects of high potassium concentration (60 mmol·L$^{-1}$) on excised blood vessels from rabbits.

In vitro animal experiment suggested that, compound II-29 could relax vascular smooth muscles constricted by adrenaline and high potassium concentration, with $-\log EC_{50}$ values of relaxation of 6.01±0.02 and 5.64±0.01, respectively (FIG. 15 and FIG. 16). Compound II-31 could relax vascular smooth muscles constricted by adrenaline and high potassium concentration, with $-\log EC_{50}$ values of relaxation of 6.19±0.03 and 5.55±0.03, respectively (FIG. 10 and FIG. 11).

Figure 12:
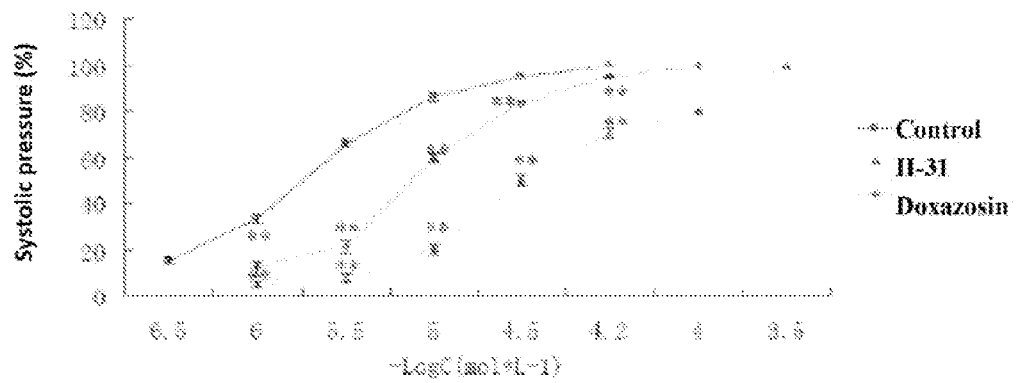
FIG. 12 illustrates the accumulated concentration effect curve of resistance of compound II-31 ($3 \times 10^{-6}$ mol/L) and positive reference drug doxazosin ($10^{-7}$ mol/L) to vasoconstrictive effects of noradrenaline NA ($3 \times 10^{-7}$-$10^{-4}$ mol/L) on excised blood vessels from rabbits.
Figure 13:
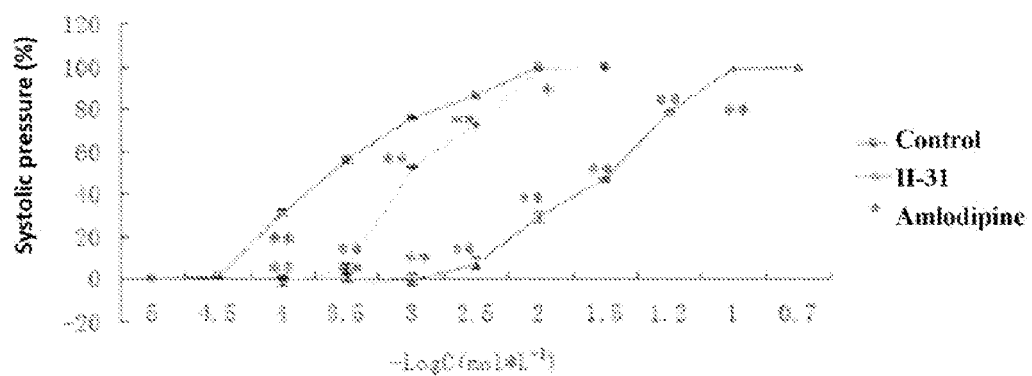
FIG. 13 illustrates the accumulated concentration effect curve of resistance of compound II-31 ($10^{-5}$ mol/L) and amlodipine ($10^{-7}$ mol/L) to vasoconstrictive effects of CaCl$_2$ ($10^{-5}$-$3 \times 10^{-1}$ mol/L) on excised blood vessels from rabbits.
Figure 14:
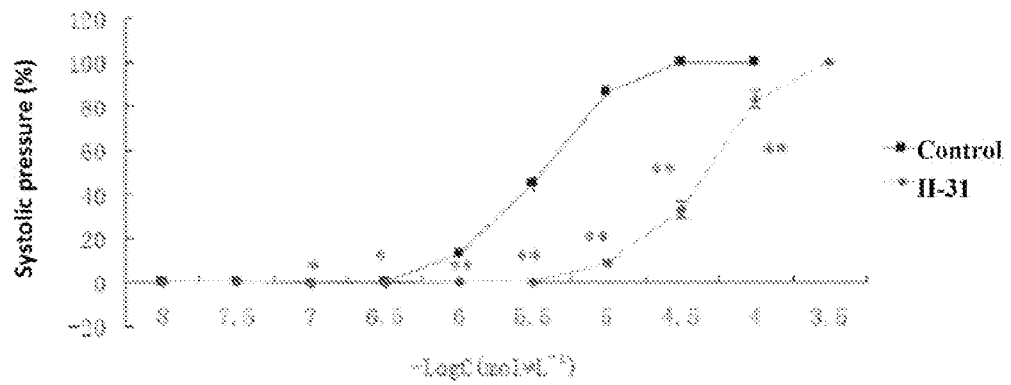
FIG. 14 illustrates the accumulated concentration effect curve of resistance of compound II-31 ($3 \times 10^{-6}$ mol/L) to vasoconstrictive effects of 5-hydroxytryptamine ($10^{-8}$-$3 \times 10^{-4}$ mol/L) on excised blood vessels from rabbits.

It was indicated in a study on dilating mechanism of compound II-31 on vascular smooth muscle that, the compound could competitively resist the vasoconstrictive effects of noradrenaline, calcium ions and hydroxytryptamine, move the dose effect curve of above said agonist transversally to right, while maximal response was not reduced, suggesting that $PA_2$ values for the compound to resist vasoconstrictive effects of noradrenaline, calcium ions and hydroxytryptamine were 6.02±0.13 (7.76±0.24 for doxazosin), 6.56±0.032 (7.51±0.288 for amlodipine) and 6.726±0.089 (FIGS. 12, 13 and 14). These results indicated that, compound II-31 produced vasodilative effects by blocking $\alpha_1$ receptor, $Ca^{2+}$ ion channel and vascular $5\text{-HT}_{2A}$ receptor.

In in vivo bulk testing on rats, compound II-2 showed good hypotensive effects, good oral absorption, mild toxicity, great therapeutic index, negative marrow micronucleus test, with protential value in development of multiple target vasodilative drugs.

The vivo bulk testing on hypotensive effects in rats indicated that, compound II-85 had obvious hypotensive effects, good oral absorption, relatively mild acute toxicity, greater therapeutic index, negative marrow micronucleus test, with protential values in development of vasodilative drugs, especially new hypotensive drugs.

The inventor found that, the said compound in formula (I) and its salts acceptably pharmaceutically in this invention have obvious relaxing effects on vascular smooth muscles of subjects. The said compound in formula (I) and its salts acceptable pharmaceutically in this invention may produce relaxing effects on vascular smooth muscles by antagonism against a receptors (especially $\alpha_1$ receptors). In addition, compound in formula (I) and its salts acceptably pharmaceutically in this invention may achieve relaxing effects on vascular smooth muscles by acting on other targets or approaches, e.g., $Ca^{2+}$ channel blockade or antagonism against $5\text{-HT}_{2A}$ receptors. Compounds with multiple targets in this invention are particularly preferable, e.g., compound I-2 or II-2, compound I-85 or II-85. With multiple targets, compounds in this invention are particularly effective against diseases related with persistent and pathological vascular constriction or spasm of vascular smooth muscle. When the compounds are used in combination with one or more single target drugs against the said diseases, higher efficacy may be achieved, or drug resistance or undesireble side effects may be effectively reduced, thus improving safety. Specifically, because of multiple target effects, when $\alpha_1$ receptor of vascular smooth muscle is incompletely blocked, good hypotensive efficacy may be produced by synergistically blocking $Ca^{2+}$ channel and/or $5\text{-HT}_{2A}$ receptor, then the remaining $\alpha_1$ receptors could still participate in pressor reflex, which may prevent and reduce the occurrence of orthostatic hypotension. And/or by blocking $Ca^{2+}$ channel, in addition to synergistic hypotensive effects, effects may be produced to resist myocardial hypertrophy, protect vascular endothelia, resist atherosclerosis, inhibit hyperplasia of vascular smooth muscle, and improve cerebral blood circulation, and prevent occurrence of first dose effect by reducing heart rate, effectively preventing tachycardia and palpitation. And/or by blocking $5\text{-HT}_{2A}$ receptors, in addition to synergistic hypotensive effects, the drug combination may effectively improve blood supply to patients with occlusion vascular diseases, then the compound may be used to hypertension patients with atherosclerosis and endothelial injuries.

Therefore, compound in formula (I) and the salts acceptable pharmaceutically in this invention may be used to prevent, alleviate or treat subjects with diseases or symptoms related with persistent and pathological constriction or vascular spasm. The said compound in formula (I) and the salts acceptable pharmaceutically may be specially used to prevent, alleviate or treat hypertension, heart failure, angina pectoris and coronary heart diseases, etc. The compound and its salts may be used to treat cerebral ischemic diseases, myocardial ischemic diseases, shock, etc. induced by vascular spasm. The compound and its salts may be used to treat renal hypofunction resulted by renal vasospasm and diseases related with peripheral vascular spasm.

Subjects described in this invention should be mammals preferably, especially human.

This invention offers compound in formula (I) or its salts acceptable pharmaceutically preferably for prevention, alleviation or treatment against hypertension, angina pectoris, heart failure, coronary heart disease, cerebral ischemia and peripheral vascular spasmodic diseases, such as thromboangitis obliterans and raynauds disease, etc.

Compound in formula (I) and its salts acceptable pharmacological in this invention can be prepared into appropriate complexes for oral, parenteral, nasal spraying, rectal, intranasal, sublingual, intrabuccal, percutaneous or implantable administrations, and the said parenteral administration includes subcutaneous, intradermal, intravneous, intramuscular, intraarticular, intrasynovial, intrasternal, intrathecal, focal, intracranial or instillation techniques. Compound and its salts acceptable pharmaceutically in this invention (I) are preferred to be administered by oral, sublingual, intravenous, intramuscular and subcutaneous approaches. The said drug complexes may contain one or more routine medicinal carrier, adjuvant or media, e.g., diluent, excipient like water, etc.; adhesives like fibrin derivatives, gelatin, polyvidone, etc.; bulking agent like starch, etc.; disintegrant like calcium carbonate, sodium bicarbonate, etc.; lubricant like calcium stearate or magnesium stearate, etc.; and other adjuvants like flavor and sweetener.

The said drug complexes containing compound in formula (I) and its salts acceptable pharmaceutically in this invention may be in the form of sterile injection solution, e.g., sterile aqueous or oily suspension. This suspension may be prepared by using appropriate dispersing agent or lubricant (e.g., Tween 80) and suspending agent based on known techniques in this field. Sterile injection solution may also be sterile injection solution or suspension applicable to nontoxic diluent or solvent for parenteral medications, e.g., solution in 1,3-butylene glycol. Applicable media and solvents may be mannitol, water, Ringer's solution and isotonic sodium chloride solution. In addition, sterile nonvolatile oil may be routinely used as solvent or suspension media. Therefore, any mild nonvolatile oil may be used, including synthetic monoglyceride and diacylglycerol. Fatty acids, e.g., oleinic acid and its glyceride derivatives, may be used in injection preparation, or natural medicinal oil may also be used, e.g., olive oil or castor oil, especially its polyoxyethylene compound. The said oily solution or suspension also includes long chain alcohol or dispersing agent (including those described in Ph. Helv) or similar alcohol.

The said drug complexes containing compound in formula (I) and its salts acceptable pharmaceutically in this invention may be orally administered in any oral dosage form, and the said dosage forms include, but not limit to, capsules, tablets, powders, granules, aqueous suspension and solution. The said dosage form is prepared by using mature techniques in the field of pharmaceutical preparation. For oral tablets, carriers usually used include lactose and corn starch. Lubricant is usually added (e.g., magnesium stearate). For oral administration in the form of capsules, the applicable diluents include lactose and dry corn starch. When aqueous suspension is orally administered, active components can bind to emulsifying and suspending agents. If necessary, some sweeteners and/or flavors and/or colorants can be added.

The said drug complexes containing compound in formula (I) and its salts acceptable pharmaceutically in this invention may be used in the form of nasal aerosol or inhaled. These complexes can be prepared by using mature techniques in the field of pharmaceutical preparation into saline solutions by using benzoic alcohol or other appropriate antiseptics, absorbefacient to improve bioavailability, fluorocarbon and/or other known solubilizing agents or dispersants in this field.

The said drug complexes containing compound in formula (I) and its salts acceptable pharmaceutically in this invention may be used in the form of rectal suppository. The said complexes are prepared by mixing compound in this invention and appropriate non-irritant excipient, and the said excipient is solid at ambient temperature but liquid at rectal temperature, and the complex will release active components after dissolution in rectum. These substance include but not limit to, cacao butter, bees wax and polyethylene glycol.

As deduced based on results of rat experiment, the daily dose of compound in formula (I) in this invention should be less than the daily dose of amlodipine. In this field, the daily dose is known for amlodipine to relax blood vessels or treat hypotension, e.g., 10 mg/day. The specific dose of this compound in formula (I) in this invention may be determined based on results of clinical trial, patient's conditions and age, etc.

The said drug complexes containing compound in formula (I) and its salts acceptable pharmaceutically in this invention may be prepared by using routine method in medical field, with 0.1%-99.5% w/w of active ingredients, which may be determined by diseases to be treated or prevented, and conditions of subjects to whom the said compound may be administered. Dosage regimen of the administered compound can be easily determined by technicians in the field based on contents publicized in this document.

In another embodiment, the compound in formula (I) or its salts acceptable pharmaceutically in this invention may be combined with one or more other active pharmaceutical ingredients. This drug combination may be a single complex containing compound or its salts acceptable pharmaceutically in this invention and one or more other active ingredients, or combination of two or more complexes, where compound in this invention is contained in one complex, while one or more other active ingredients are contained in one or more separate complexes. Compound in formula (I) or the salts acceptable pharmaceutically in this invention may be combined with other active ingredients, such as antispasmodic against smooth muscle spasm, preferably sertraline, captopril, benazepril, valsartan, inderal and diuretics, to prevent, alleviate or treat subjects with diseases or symptoms related with persistent and pathological constriction or vascular spasm.

Except otherwise specified, the embodiments described in this application, or regimens with different preferabilities, may be freely combined.

Compound in this invention can be synthesized by adopting the following methods:

Synthetic Approach 1:

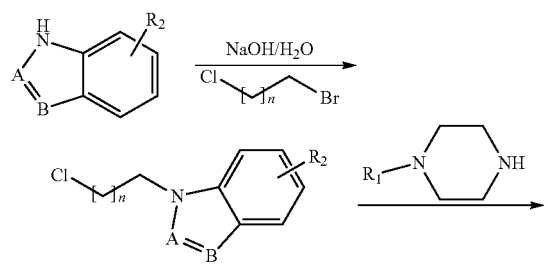

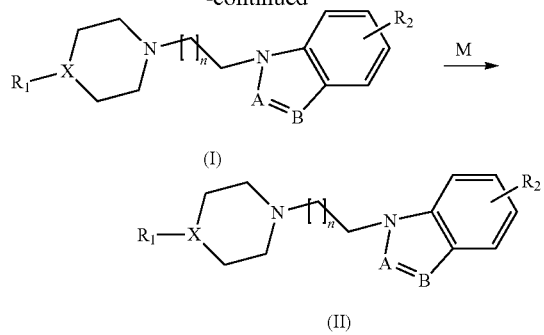

Wherein, $R_1$, $R_2$, A, B and X are described in the above text. n=0-7. M indicates medical drugs, e.g., HCl, 2HCl, HBr, 2HBr, $H_2SO_4$, $CH_3SO_3H$, etc.

In sodium hydroxide solution, substituted 1H-benzo five-membered nitrogen heterocyclic ring is used as raw material to condense with chloro-alkyl bromide to prepare N-chloro-alkyl substituted benzo five-membered nitrogen heterocyclic compound, and condense with substituted piperazine and piperidine to prepare the indicated compound in formula (I), finally corresponding salt will be prepared by acidification to produce compound in formula (II). The above method may be used to prepare compound I-1 to I-21, I-25 to I-51, I-54 to I-60, I-84 to I-87, I-100 to I-102, I-124 to I-132, I-135 to I-146, I-149 to I-157, and their salts.

Synthetic Approach 2:

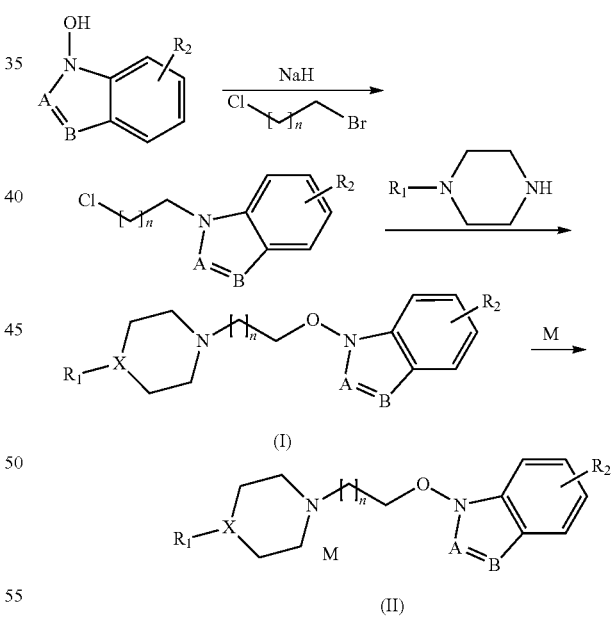

Wherein, $R_1$, $R_2$, A, B and X are described in the above text. n=0-7. M indicates medical drugs, e.g., HCl, 2HCl, HBr, 2HBr, $H_2SO_4$, $CH_3SO_3H$, etc.

Substituted benzo five-membered nitrogen heterocyclic-1-ol is used as raw material to exchange active hydrogen with sodium hydride to produce corresponding salt, and react with chloro-alkyl bromide to produce corresponding chloride, and condense with piperazine and piperidine to prepare the indicated compound in formula (I), finally corresponding salt will be prepared by acidification to produce compound in formula (II). The above method may be used to prepare compound I-22 to I-24, I-52 to I-53, I-98 to I-99, I-133 to I-134, I-147 to I-148, and their salts.

Common method one for synthesis: preparation of N-(4-chlorobutyl)-substituted benzo five-membered nitrogen heterocyclic compound 1H-substituted benzo five-membered nitrogen heterocyclic compound (0.10 mol) is dissolved into 100 ml of 30% wt. sodium hydroxide, 4-chlorobromobutane (34.0 g, 0.10 mol), tetrabutyl ammonium bromide (0.8 g) are added, and mixed for 5 min. The reaction solution is gradually heated to 60° C., stirred for reaction for 2 hours. Then the reaction solution is cooled down to ambient temperature, 100 ml of dichloromethane is added for extraction and liquid separation. To the aqueous phase, 100 of dichloromethane is added for extraction. Organic phases are mixed, washed with 100 ml of saturated saline. Liquid is separated, and organic phase is evaporated to dryness to produce oily product. Oily products are analyzed by chromatography with neutral $Al_2O_3$, or separated and purified by using HPLC to prepare N-(4-chlorobutyl)-substituted benzo five-membered nitrogen heterocyclic compound, with a yield range of 30.0%-85.0%.

Common method two for synthesis: preparation of N-(3-chloropropyl)-substituted benzo five-membered nitrogen heterocyclic compound 1H-substituted benzo five-membered nitrogen heterocyclic compound (0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Then the reaction solution is cooled down to ambient temperature, 100 ml of dichloromethane is added for extraction and liquid separation. To the aqueous phase, 100 of dichloromethane is added for extraction. Organic phases are mixed, washed with 100 ml of saturated saline. Liquid is separated, and organic phase is evaporated to dryness to produce oily product. Oily products are analyzed by chromatography with neutral $Al_2O_3$, or separated and purified by using HPLC to prepare N-(3-chloropropyl)-substituted benzo five-membered nitrogen heterocyclic compound, with a yield range of 30.0%-85.0%.

Common method three for synthesis: preparation of N-(3-substituted benzo five-membered nitrogen heterocyclic) proply-4-substituted piperidine N-(3-chloropropyl)-substituted benzo five-membered nitrogen heterocyclic compound (0.06 mol) into 150 ml of acetonitrile, 4-substituted piperidine (0.05 mol), diisopropylethylamine (0.2 mol) and potassium iodide (0.05 mol) are respectively added. The mixture is mixed at ambient temperature for 10 min, then heated and refluxed for reaction for 10-20 hours. The mixture is cooled down to ambient temperature and filtered. The filtrate is concentrated to produce oily products, and treated by chromatography with neutral $Al_2O_3$, eluted with dichloromethane/methanol mixture to produce compound in formula (I) with a yield range of 65.0%-72.0%.

Common method four for synthesis: preparation of N-(2-chloroethoxyl)-substituted benzo five-membered nitrogen heterocyclic compound Substituted N-hydroxyl benzo five-membered nitrogen heterocyclic compound (0.01 mol) is dissolved in 10 ml of NMP, solid paraffin mixture containing 50% (w/w) hydrogen and oxygen is added in different times, stirred to react for 0.5 h. Meanwhile, 3-bromochloropropane (0.015 mol) is dissolved in 5 ml of NMP and added into the above said solution, and stirred to react for 12 h. Reaction solution is poured into 50 ml of water, extracted with ethyl acetate (3×50 mL). Organic phases are mixed and washed with 30 ml of water. Anhydrous magnesium sulfate is added to dry organic phase, filtered, with solvent evaporated. Oily products are analyzed by chromatography with neutral $Al_2O_3$, or separated and purified by using HPLC to prepare 1-(2-chloroethoxyl)-substituted benzo five-membered nitrogen heterocyclic compound, with a yield range of 75.0%-85.0%.

The following examples are combined to illustrate this invention.

Example 1

Preparation of 1-(4-(4-(3-chlorophenyl)piperazine-1-yl)butyl)-1H-benzimidazole (I-1)

1H-benzimidazole (11.8 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 12.5 g of 1-(4-chlorobutyl)-1H-benzimidazole, with a yield of 60.0%.

1-(4-chlorobutyl)-1H-benzimidazole (7.51 g, 0.036 mol) was dissolved into 100 ml of acetonitrile, 3-trichloro phenylpiperazine (5.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 6.8 g compound (I-1) with a yield of 61.4%. ESI-MS [M+H]$^+$: m/z 369.2.

Example 2

Preparation of 1-(4-(4-(3-trifluoromethylphenyl)piperazine-1-yl)butyl)-1H-benzimidazole (I-2) and 1-(4-(4-(3-trifluoromethylphenyl)piperazine-1-yl)butyl)-1H-benzimidazole hydrochlorate (II-2)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for −20 hours. The mixture was cooled down to ambient temperature and filtered. The filtrate was concentrated to produce oily products, and treated by chromatography with neutral $Al_2O_3$, eluted with dichloromethane/methanol mixture to produce 7.6 g compound (I-2) with a yield of 62.8%.

Compound (I-2) (6.04 g, 0.015 mol) was dissolved in 80 ml of ethyl acetate and 8 ml of ethanol. Under cooling conditions of icy water bath, 3 mol/L hydrogen chloride/ethyl acetate solution is dripped, and the pH value is adjusted to 3. The mixture is heated to 50° C. and stirred for 20 min, cooled

Example 3

Preparation of 1-(4-(4-(2,3-dichlorophenyl)piperazine-1-yl)butyl)-1H-benzimidazole (I-3) and 1-(4-(4-(2,3-dichlorophenyl)piperazine-1-yl)butyl)-1H-benzimidazole hydrochlorate (II-3)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 2,3-dichloro phenylpiperazine (6.93 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-20 hours. The mixture was cooled down to ambient temperature and filtered. The filtrate was concentrated to produce oily products, and treated by chromatography with neutral $Al_2O_3$, eluted with dichloromethane/methanol mixture to produce 7.5 g compound (I-3) with a yield of 62.0%.

Compound (I-3) (6.05 g, 0.015 mol) was dissolved in 80 ml of ethyl acetate and 8 ml of ethanol. Under cooling conditions of icy water bath, 3 mol/L hydrogen chloride/ethyl acetate solution is dripped, and the pH value is adjusted to 3. The mixture is heated to 50° C. and stirred for 20 min, cooled down for recrystallization, filtered and dried to produce 6.0 g solid compound (II-3) with a yield of 90.9%. ESI-MS [M+H]$^+$: m/z 403.1.

Example 4

Preparation of 1-(4-(4-(2-methoxyphenyl)piperazine-1-yl)butyl)-1H-benzimidazole (I-4)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 2-methoxyphenyl piperazine (5.77 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral $Al_2O_3$, eluted with dichloromethane/methanol mixture to produce 7.7 g compound (I-4) with a yield of 70.6%. ESI-MS [M+H]$^+$: m/z 365.2.

Example 5

Preparation of 2-methyl-1-(4-(4-(3-trifluoromethylphenyl)piperazine-1-yl)butyl)-1H-benzimidazole (I-5)

2-methyl-1H-benzimidazole (13.2 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 13.7 g of 1-(4-chlorobutyl)-2-methyl-1H-benzimidazole, with a yield of 61.5%.

1-(4-chlorobutyl)-2-methyl-1H-benzimidazole (8.02 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.1 g compound (I-5) with a yield of 64.9%. ESI-MS [M+H]$^+$: m/z 417.2.

Example 6

Preparation of 6-fluoro-1-(4-(4-(3-trifluoromethylphenyl)piperazine-1-yl)butyl)-1H-benzimidazole (I-6)

6-fluoro-1H-benzimidazole (13.2 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Post treatment was performed based on common method one for synthesis. Oily products were separated and purified by chromatography with neutral $Al_2O_3$ to produce 14.2 g of 1-(4-chlorobutyl)-6-fluoro-1H-benzimidazole, with a yield of 62.6%.

1-(4-chlorobutyl)-6-fluoro-1H-benzimidazole (8.16 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.5 g compound (I-6) with a yield of 67.4%. ESI-MS [M+H]$^+$: m/z 421.2.

Example 7

Preparation of 1-(3-(4-phenylpiperazine-1-yl)propyl)-1H-benzimidazole (I-7)

1H-benzimidazole (11.8 g, 0.10 mol) was dissolved into 200 ml of 20% wt. sodium hydroxide, 3-chlorobromopropane (31.4 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral Al₂O₃ to produce 12.0 g of 1-(3-chloropropyl)-1H-benzimidazole, with a yield of 62.0%.

1-(3-chloropropyl)-1H-benzimidazole (6.98 g, 0.036 mol) was dissolved into 100 ml of acetonitrile, phenyl piperazine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral Al₂O₃, eluted with dichloromethane/methanol mixture to produce 6.1 g compound (I-7) with a yield of 63.2%. ESI-MS [M+H]⁺: m/z 321.2.

Example 8

Preparation of 1-(3-(4-(3-fluorophenyl)piperazine-1-yl)propyl)-1H-benzimidazole (I-8)

The method described in Example 7 was adopted to prepare 1-(3-chloropropyl)-1H-benzimidazole.

1-(3-chloropropyl)-1H-benzimidazole (6.98 g, 0.036 mol) was dissolved into 100 ml of acetonitrile, 3-fluorophenyl piperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral Al₂O₃, eluted with dichloromethane/methanol mixture to produce 6.4 g compound (I-8) with a yield of 63.1%. ESI-MS [M+H]⁺: m/z 339.2.

Example 9

Preparation of 2-methyl-1-(3-(4-(3-fluorophenyl) piperazine-1-yl)propyl)-1H-benzimidazole (I-9)

2-methyl-1H-benzimidazole (13.2 g, 0.10 mol) was dissolved into 200 ml of 20% wt. sodium hydroxide, 3-chlorobromopropane (31.4 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral Al₂O₃ to produce 12.9 g of 1-(3-chloropropyl)-2-methyl-1H-benzimidazole, with a yield of 62.1%.

1-(3-chloropropyl)-2-methyl-1H-benzimidazole (7.49 g, 0.036 mol) was dissolved into 100 ml of acetonitrile, 3-tricholo phenylpiperazine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al₂O₃, eluted with dichloromethane/methanol mixture to produce 6.67 g compound (I-9) with a yield of 63.1%. ESI-MS [M+H]⁺: m/z 353.2.

Example 10

Preparation of 1-(4-(4-(3-cyanophenyl)piperazine-1-yl)butyl)-1H-benzimidazole (I-10)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 3-cyanophenyl piperazine (5.6 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral Al₂O₃, eluted with dichloromethane/methanol mixture to produce 6.7 g compound (I-10) with a yield of 62.4%. ESI-MS [M+H]⁺: m/z 360.2.

Example 11

Preparation of 1-(4-(4-(4-methylphenyl)piperazine-1-yl)butyl)-1H-benzimidazole (I-11)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-methylphenyl piperazine (5.3 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral Al₂O₃, eluted with dichloromethane/methanol mixture to produce 6.4 g compound (I-11) with a yield of 60.7%. ESI-MS [M+H]⁺: m/z 349.2.

Example 12

Preparation of 1-(4-(4-(2-furyl)piperazine-1-yl)butyl)-1H-benzimidazole (I-12)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-furyl) piperazine (4.6 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral Al₂O₃, eluted with dichloromethane/methanol mixture to produce 6.0 g compound (I-12) with a yield of 61.5%. ESI-MS [M+H]⁺: m/z 325.2.

Example 13

Preparation of 1-(4-(4-(4-pyridyl)piperazine-1-yl) butyl)-1H-benzimidazole (I-13)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(4-pyridyl) piperazine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.3 g compound (I-13) with a yield of 62.1%. ESI-MS $[M+H]^+$: m/z 336.2.

Example 14

Preparation of 1-(4-(4-(2-pyrimidinyl)piperazine-1-yl)butyl)-1H-benzimidazole (I-14)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-pyrimidinyl) piperazine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.1 g compound (I-14) with a yield of 60.1%. ESI-MS $[M+H]^+$: m/z 337.2.

Example 15

Preparation of 1-(4-(4-(1-cyclohexyl)piperazine-1-yl)butyl)-1H-benzimidazole (I-15)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(1-cyclohexyl) piperazine (5.1 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.4 g compound (I-15) with a yield of 62.9%. ESI-MS $[M+H]^+$: m/z 341.3.

Example 16

Preparation of 1-(4-(4-(1-naphthyl)piperazine-1-yl) butyl)-1H-benzimidazole (I-16)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(1-naphthyl) piperazine (6.4 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.8 g compound (I-16) with a yield of 59.1%. ESI-MS $[M+H]^+$: m/z 385.2.

Example 17

Preparation of 1-(4-(4-(2-quinoxalinyl)piperazine-1-yl)butyl)-1H-benzimidazole (I-17)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-quinoxalinyl) piperazine (6.4 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.9 g compound (I-17) with a yield of 59.6%. ESI-MS $[M+H]^+$: m/z 387.2.

Example 18

Preparation of 1-(4-(4-(3-(6-fluoro benzisoxazolyl)) piperazine-1-yl)butyl)-1H-benzimidazole (I-18)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 6-fluoro-3-(piperazine-4-yl)benzisoxazolyl (6.6 g, 0.05 mol), diisopropylethylamine (15.5 g, 0.12 mol) and potassium iodide (5.0 g, 0.03 mol) were respectively added. The mixture was stirred and mixed, and then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.7 g compound (I-18) with a yield of 65.6%. ESI-MS $[M+H]^+$: m/z 394.2.

Example 19

Preparation of 1-(4-(4-(3-(6-fluoro benzisothiazolyl)) piperazine-1-yl)butyl)-1H-benzimidazole (I-19)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 6-fluoro-3-(piperazine-4-yl)benzisothiazolyl (7.1 g, 0.05 mol), diisopropylethylamine (15.5 g, 0.12 mol) and potassium iodide (5.0 g, 0.03 mol) were respectively added. The mixture was stirred and mixed, and then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.9 g compound (I-19) with a yield of 64.6%. ESI-MS $[M+H]^+$: m/z 410.2.

Example 20

Preparation of 1-(4-(4-(3-benzimidazoyl)piperazine-1-yl)butyl)-1H-benzimidazole (I-20)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 3-(piperazine-4-yl) benzimidazole (6.1 g, 0.05 mol), diisopropylethylamine (15.5 g, 0.12 mol) and potassium iodide (5.0 g, 0.03 mol) were respectively added. The mixture was stirred and mixed, and then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 6.9 g compound (I-20) with a yield of 61.5%. ESI-MS [M+H]$^+$: m/z 375.2.

Example 21

Preparation of 1-(4-(4-(3-(6-fluoro benzofuranyl)) piperazine-1-yl)butyl)-1H-benzimidazole (I-21)

The method described in Example 1 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 6-fluoro-3-(piperazine-4-yl)benzofuranyl (6.6 g, 0.05 mol), diisopropylethylamine (15.5 g, 0.12 mol) and potassium iodide (5.0 g, 0.03 mol) were respectively added. The mixture was stirred and mixed, and then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.5 g compound (I-21) with a yield of 63.6%. ESI-MS [M+H]$^+$: m/z 393.2.

Example 22

Preparation of 1-(3-(4-(3-(6-fluoro benzisoxazolyl)) piperazine-1-yl)propoxyl)-1H-benzimidazole (I-22)

Preparation of 1-(3-chloro propoxyl)benzimidazole

Substituted 1-hydroxyl benzimidazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral $Al_2O_3$, or separated and purified by using HPLC to prepare 1-(3-chloropropoxyl)benzimidazole, with a yield of 75.0%.

1-(3-chloropropoxyl)benzimidazole (0.06 mol) was dissolved into 150 ml of acetonitrile, 4-(3-(6-fluoro benzisoxazolyl)) piperazine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.7 g 1-(3-(4-(3-(6-fluoro benzisoxazolyl)) piperazine-1-yl)propoxyl)-1H-benzimidazole (I-22) with a yield of 69.1%. ESI-MS [M+H]$^+$: m/z 396.2.

Example 23

Preparation of 1-(4-(4-(3-trifluoromethylphenyl) piperazine-1-yl)propoxyl)-1H-benzimidazole (I-23)

The method described in Example 22 was adopted to prepare 1-(3-chloropropoxyl)benzimidazole.

1-(3-chloropropoxyl)benzimidazole (0.06 mol) was dissolved into 150 ml of acetonitrile, 4-(3-(3-trifluoromethylphenyl) piperazine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.7 g 1-(4-(4-(3-trifluoromethylphenyl)piperazine-1-yl)propoxyl)-1H-benzimidazole (I-23) with a yield of 67.9%. ESI-MS [M+H]$^+$: m/z 405.2.

Example 24

Preparation of 1-(4-(4-(3-chlorphenyl)piperazine-1-yl)propoxyl)-1H-benzimidazole (I-24)

The method described in Example 22 was adopted to prepare 1-(3-chloropropoxyl)benzimidazole.

1-(3-chloropropoxyl)benzimidazole (0.06 mol) was dissolved into 150 ml of acetonitrile, 4-(3-(3-chlorophenyl) piperazine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.2 g 1-(4-(4-(3-fluorophenyl)piperazine-1-yl)propoxyl)-1H-benzimidazole (I-24) with a yield of 66.1%. ESI-MS [M+H]$^+$: m/z 371.2.

Example 25

Preparation of 6-chloro-1-(4-(4-(3-trifluoromethylphenyl)piperazine-1-yl)butyl)-1H-benzimidazole (I-25)

6-chloro-1H-benzimidazole (15.2 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Post treatment was performed based on common method one for synthesis. Oily products were separated and purified by chromatography with neutral $Al_2O_3$ to produce 15.1 g of 1-(4-chlorobutyl)-6-chloro-1H-benzimidazole, with a yield of 62.3%.

1-(4-chlorobutyl)-6-chloro-1H-benzimidazole (8.71 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.6 g compound (I-25) with a yield of 65.8%. ESI-MS $[M+H]^+$: m/z 437.2.

Example 26

Preparation of 6-cyano-1-(4-(4-(3-trifluoromethylphenyl)piperazine-1-yl)butyl)-1H-benzimidazole (I-26)

6-cyano-1H-benzimidazole (14.3 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Post treatment was performed based on common method one for synthesis. Oily products were separated and purified by chromatography with neutral $Al_2O_3$ to produce 14.7 g of 1-(4-chlorobutyl)-6-cyano-1H-benzimidazole, with a yield of 63.1%.

1-(4-chlorobutyl)-6-cyano-1H-benzimidazole (8.39 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.6 g compound (I-26) with a yield of 66.9%. ESI-MS $[M+H]^+$: m/z 428.2.

Example 27

Preparation of 6-methoxycarbonyl-1-(4-(4-(3-trifluoromethylphenyl)piperazine-1-yl)butyl)-1H-benzimidazole (I-27)

6-methoxycarbonyl-1H-benzimidazole (17.6 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Post treatment was performed based on common method one for synthesis. Oily products were separated and purified by chromatography with neutral $Al_2O_3$ to produce 16.9 g of 1-(4-chlorobutyl)-6-methoxycarbonyl-1H-benzimidazole, with a yield of 63.4%.

1-(4-chlorobutyl)-6-methoxycarbonyl-1H-benzimidazole (9.58 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.8 g compound (I-27) with a yield of 63.7%. ESI-MS $[M+H]^+$: m/z 461.2.

Example 28

Preparation of 2-chloro-1-(5-(4-(3-trifluoromethylphenyl)piperazine-1-yl)pentyl)-1H-benzimidazole (I-28)

2-chloro-1H-benzimidazole (15.2 g, 0.10 mol) was dissolved into 200 ml of 20% wt. sodium hydroxide, 5-chlorobromopentane (36.8 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 16.0 g of 1-(5-chloropentyl)-2-chloro-1H-benzimidazole, with a yield of 62.5%.

1-(5-chloropentyl)-2-chloro-1H-benzimidazole (9.22 g, 0.036 mol) was dissolved into 100 ml of acetonitrile, 3-trichloromethyl phenylpiperazine (6.91 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 8.8 g compound (I-28) with a yield of 65.2%. ESI-MS $[M+H]^+$: m/z 451.2.

Example 29

Preparation of 1-(4-(4-(3-chlorophenyl)piperazine-1-yl)butyl)-1H-benzotriazole (I-29)

Benzotriazole (11.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.0 g of 1-(4-chlorobutyl)-1H-benzotriazole, with a yield of 81.0%.

1-(4-chlorobutyl)-1H-benzotriazole (7.55 g, 0.036 mol) was dissolved into 100 ml of acetonitrile, 3-trichloro phenylpiperazine (5.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 7.8 g compound (I-29) with a yield of 70.3%.

Compound (I-29) (5.55 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.4 g solid compound (II-29) with a yield of 88.0%. ESI-MS [M+H]$^+$: m/z 370.1.

Example 30

Preparation of 1-(4-(4-(3-fluorophenyl)piperazine-1-yl)butyl)-1H-benzotriazole (I-30)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 3-trifluoro phenylpiperazine (5.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 7.3 g compound (I-30) with a yield of 68.9%. ESI-MS [M+H]$^+$: m/z 354.2.

Example 31

Preparation of 1-(4-(4-(3-trifluoromethylphenyl)piperazine-1-yl)butyl)-1H-benzotriazole (I-31) and 1-(4-(4-(3-trifluoromethylphenyl)piperazine-1-yl)butyl)-1H-benzotriazole (II-31)

1-(4-chlorobutyl)-1H-benzotriazole (7.55 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 7.8 g compound (I-31) with a yield of 64.5%.

Compound (I-31) (6.05 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.6 g solid compound (II-31) with a yield of 84.8%. ESI-MS [M+H]$^+$: m/z 404.2.

Example 32

Preparation of 6-fluoro-1-(4-(4-(3-trifluoromethylphenyl)piperazine-1-yl)butyl)-1H-benzotriazole (I-32)

6-fluoro-1H-benzotriazole (13.7 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 8.9 g of 1-(4-chlorobutyl)-6-fluoro-1H-benzotriazole, with a yield of 39.0%.

1-(4-chlorobutyl)-6-fluoro-1H-benzotriazole (8.2 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 8.3 g compound (I-32) with a yield of 65.7%. ESI-MS [M+H]$^+$: m/z 422.2.

Example 33

Preparation of 5,6-dimethyl-1-(4-(4-(3-trifluoromethylphenyl)piperazine-1-yl)butyl)-1H-benzotriazole (I-33)

5,6-dimethyl-1H-benzotriazole (14.7 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 17.4 g of 1-(4-chlorobutyl)-5,6-dimethyl-1H-benzotriazole, with a yield of 73.2%.

1-(4-chlorobutyl)-5,6-dimethyl-1H-benzotriazole (8.56 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 9.1 g compound (I-33) with a yield of 70.3%. ESI-MS [M+H]$^+$: m/z 432.2.

Example 34

Preparation of 3-(4-(4-(1H-benzotriazole-1-yl)butyl)piperazine-1-yl)benzisothiazole (I-34)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 3-(piperazine-1-yl)benzisothiazole (6.58 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 8.2 g compound (I-34) with a yield of 69.6%.

Compound (I-34) (5.89 g, 0.015 mol) was dissolved in 50 ml of ethyl acetate and 5 ml of ethanol. Under cooling conditions of icy water bath, 3 mol/L hydrogen chloride/ethyl acetate solution is dripped, and the pH value is adjusted to 2.

Example 35

Preparation of 3-(4-(4-(1H-benzotriazole-1-yl)butyl) piperazine-1-yl)benzisoxazolyl (I-35)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 3-(piperazine-1-yl)benzisoxazole (6.1 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.0 g compound (I-35) with a yield of 70.9%. ESI-MS $[M+H]^+$: m/z 377.2.

Example 36

Preparation of 6-fluoro-3-(4-(4-(1H-benzotriazole-1-yl)butyl)piperazine-1-yl)benzisoxazole (I-36)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 6-fluoro-3-(piperazine-1-yl)benzisoxazole (6.1 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.3 g compound (I-36) with a yield of 70.0%. ESI-MS $[M+H]^+$: m/z 395.2.

Example 37

Preparation of 6-fluoro-3-(4-(3-(1H-benzotriazole-1-yl)propyl)piperazine-1-yl)benzisoxazole (I-37)

Benzotriazole (11.9 g, 0.10 mol) is dissolved into 100 ml of 30% wt. sodium hydroxide, 3-chlorobromopropane (30.2 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 15.6 g of 1-(3-chloropropyl)-1H-benzotriazole, with a yield of 80.0%.

1-(3-chloropropyl)-1H-benzotriazole (7.02 g, 0.036 mol) was dissolved into 100 ml of acetonitrile, 6-fluoro-3-(piperazine-1-yl)benzisoxazole (6.6 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.9 g compound (I-37) with a yield of 69.3%. ESI-MS $[M+H]^+$: m/z 380.2.

Example 38

Preparation of 1-(3-(4-(2,3-dichlorophenyl)piperazine-1-yl)butyl)-1H-benzotriazole (I-38)

The method described in Example 37 was adopted to prepare 1-(3-chloropropyl)-1H-benzotriazole.

1-(3-chloropropyl)-1H-benzotriazole (7.02 g, 0.036 mol) was dissolved into 100 ml of acetonitrile, 2,3-dicholoro phenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.2 g compound (I-38) with a yield of 70.2%. ESI-MS $[M+H]^+$: m/z 389.1.

Example 39

Preparation of 1-(3-(4-(3-methylphenyl)piperazine-1-yl) butyl)-1H-benzotriazole (I-39)

The method described in Example 37 was adopted to prepare 1-(3-chloropropyl)-1H-benzotriazole.

1-(3-chloropropyl)-1H-benzotriazole (7.02 g, 0.036 mol) was dissolved into 100 ml of acetonitrile, 3-methyl phenylpiperazine (5.3 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.5 g compound (I-39) with a yield of 74.6%. ESI-MS $[M+H]^+$: m/z 335.2.

Example 40

Preparation of 1-(4-(4-(3-methoxyphenyl)piperazine-1-yl)butyl)-1H-benzotriazole (I-40)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 3-methyl phenylpiperazine (5.8 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.6 g compound (I-40) with a yield of 69.4%. ESI-MS $[M+H]^+$: m/z 365.2.

Example 41

Preparation of 1-(4-(4-(3-cyanophenyl)piperazine-1-yl)butyl)-1H-benzotriazole (I-41)

The method described in Example 29 was adopted to prepare 1-(4-chlorobutyl)-1H-benzotriazole.

The mixture is stirred for 10 min, filtered and dried to produce 5.5 g solid compound (II-34) with a yield of 85.5%. ESI-MS $[M+H]^+$: m/z 393.2.

1-(4-chlorobutyl)-1H-benzotriazole (7.55 g, 0.036 mol) was dissolved into 100 ml of acetonitrile, 3-cyano phenylpiperazine (5.6 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.6 g compound (I-41) with a yield of 70.5%. ESI-MS [M+H]$^+$: m/z 360.2.

Example 42

Preparation of 1-(5-(4-(3-trifluoromethylphenyl) piperazine-1-yl)pentyl)-1H-benzotriazole (I-42)

Benzotriazole (11.9 g, 0.10 mol) is dissolved into 100 ml of 30% wt. sodium hydroxide, 5-chlorobromopentane (36.8 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 15.8 g of 1-(5-chloropentyl)-1H-benzotriazole, with a yield of 71.0%.

1-(5-chloropentyl)-1H-benzotriazole (8.0 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.7 g compound (I-42) with a yield of 61.5%. ESI-MS [M+H]$^+$: m/z 417.2.

Example 43

Preparation of 1-(4-(4-(2-furyl)piperazine-1-yl)butyl)-1H-benzotriazole (I-43)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(2-furyl)piperazine (4.6 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.0 g compound (I-43) with a yield of 71.3%. ESI-MS [M+H]$^+$: m/z 325.2.

Example 44

Preparation of 1-(4-(4-(4-pyridyl)piperazine-1-yl) butyl)-1H-benzotriazole (I-44)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(4-pyridyl)piperazine (4.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.6 g compound (I-44) with a yield of 65.3%. ESI-MS [M+H]$^+$: m/z 336.2.

Example 45

Preparation of 1-(4-(4-(2-pyrimidinyl)piperazine-1-yl)butyl)-1H-benzotriazole (I-45)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(2-pyrimidinyl) piperazine (4.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.8 g compound (I-45) with a yield of 67.1%. ESI-MS [M+H]$^+$: m/z 337.2.

Example 46

Preparation of 1-(4-(4-cyclohexyl piperazine-1-yl) butyl)-1H-benzotriazole (I-46)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-cyclohexyl) piperazine (5.1 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.5 g compound (I-46) with a yield of 63.7%. ESI-MS [M+H]$^+$: m/z 341.2.

Example 47

Preparation of 1-(4-(4-(1-naphthyl)piperazine-1-yl) butyl)-1H-benzotriazole (I-47)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-naphthyl)piperazine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.9 g compound (I-47) with a yield of 60.1%. ESI-MS [M+H]⁺: m/z 385.2.

Example 48

Preparation of 1-(4-(4-(2-quinoxalinyl)piperazine-1-yl)butyl)-1H-benzotriazole (I-48)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(2-quinoxalinyl)piperazine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.3 g compound (I-48) with a yield of 62.7%. ESI-MS [M+H]⁺: m/z 387.2.

Example 49

Preparation of 1-(4-(4-(3-(6-fluoro benzisothiazolyl))piperazine-1-yl)butyl)-1H-benzotriazole (I-49)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 6-fluoro-3-(piperazine-4-yl)benzisothiazole (6.6 g, 0.05 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 8.2 g compound (I-49) with a yield of 66.5%. ESI-MS [M+H]⁺: m/z 410.2.

Example 50

Preparation of 1-(4-(4-(3-benzimidazoyl)piperazine-1-yl)butyl)-1H-benzotriazole (I-50)

The method described in Example 29 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 3-(piperazine-4-yl)benzopyrazole (6.1 g, 0.05 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.7 g compound (I-50) with a yield of 68.2%. ESI-MS [M+H]⁺: m/z 375.2.

Example 51

Preparation of 1-(3-(4-(3-(6-fluoro benzofuranyl))piperazine-1-yl)propyl)-1H-benzotriazole (I-51)

The method described in Example 37 was adopted to prepare 1-(3-chloropropyl)-1H-benzotriazole.

1-(3-chloropropyl)-1H-benzotriazole (7.55 g, 0.036 mol) was dissolved into 100 ml of acetonitrile, 6-fluoro-3-(piperazine-4-yl)benzofuran (6.6 g, 0.05 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.9 g compound (I-51) with a yield of 69.1%. ESI-MS [M+H]⁺: m/z 379.2.

Example 52

Preparation of 1-(4-(4-(3-(6-fluoro benzisoxazolyl))piperazine-1-yl)propoxyl)-1H-benzotriazole (I-52)

Preparation of 1-(3-chloro propoxyl)benzotriazole

Substituted 1-hydroxyl benzotriazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral $Al_2O_3$, or separated and purified by using HPLC to prepare 1-(3-chloropropoxyl)benzotriazole, with a yield of 75.0%.

1-(3-chloropropoxyl)benzotriazole (0.06 mol) was dissolved into 150 ml of acetonitrile, 4-(3-(6-fluoro benzisoxazolyl)) piperazine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.4 g 1-(4-(4-(3-(6-fluoro benzisoxazolyl)) piperazine-1-yl)propoxyl)-1H-benzotriazole (I-52) with a yield of 67.6%. ESI-MS [M+H]⁺: m/z 396.2.

Example 53

Preparation of 6-fluoro-1-(4-(4-(3-(6-fluoro-benzisothiazolyl))piperazine-1-yl) propoxyl)-1H-benzotriazole (I-53)

Preparation of 6-fluoro-1-(2-chloro propoxyl)benzotriazole

Substituted 6-fluoro-1-hydroxyl benzotriazole (0.01 mol) was dissolved in 10 ml of NMP, solid paraffin mixture (0.01 mol) containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral $Al_2O_3$, or separated and purified by using HPLC to prepare 6-fluoro-1-(3-chloropropoxyl)benzotriazole, with a yield of 75.0%).

6-fluoro-1-(3-chloropropoxyl)benzotriazole (0.06 mol) was dissolved into 150 ml of acetonitrile, 4-(3-(6-fluorobenzisothiazolyl)) piperazine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 14.1 g 6-fluoro-1-(4-(4-(3-(6-fluoro-benzisothiazolyl))piperazine-1-yl)propoxyl)-1H-benzotriazole (I-53) with a yield of 65.6%. ESI-MS [M+H]$^+$: m/z 430.1.

Example 54

Preparation of 6-chloro-1-(4-(4-(3-trifluoromethylphenyl)piperazine-1-yl)butyl)-1H-benzotriazole (I-54)

6-chloro-benzotriazole (15.3 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 19.2 g of 6-chloro-1-(4-chlorobutyl)-1H-benzotriazole, with a yield of 79.0%.

6-chloro-1-(4-chlorobutyl)-1H-benzotriazole (8.75 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.5 g compound (I-54) with a yield of 64.7%. ESI-MS [M+H]$^+$: m/z 437.2.

Example 55

Preparation of 6-cyano-1-(4-(4-(3-trifluoromethylphenyl)piperazine-1-yl)butyl)-1H-benzotriazole (I-55)

6-cyano-benzotriazole (14.4 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.8 g of 6-cyano-1-(4-chlorobutyl)-1H-benzotriazole, with a yield of 76.0%.

6-cyano-1-(4-chlorobutyl)-1H-benzotriazole (8.42 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.5 g compound (I-55) with a yield of 66.4%. ESI-MS [M+H]$^+$: m/z 428.2.

Example 56

Preparation of 6-methoxycarbonyl-1-(4-(4-(3-trifluoromethylphenyl)piperazine-1-yl)butyl)-1H-benzotriazole (I-56)

6-methoxycarbonyl-benzotriazole (17.7 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 19.5 g of 6-methoxycarbonyl-1-(4-chlorobutyl)-1H-benzotriazole, with a yield of 73.0%.

6-methoxycarbonyl-1-(4-chlorobutyl)-1H-benzotriazole (9.61 g, 0.036 mol) was dissolved into 100 ml of acetonitrile, 3-trifluoro methylphenylpiperazine (6.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 8.8 g compound (I-56) with a yield of 63.4%. ESI-MS [M+H]$^+$: m/z 461.2.

Example 57

Preparation of 1-(4-(4-(3-trifluoromethylphenyl) piperazine-1-yl)butyl)-1H-indole (I-57)

1H-indole (11.7 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 12.5 g of 1-(4-chlorobutyl)-1H-indole, with a yield of 60.1%.

1-(4-chlorobutyl)-1H-indole (7.45 g, 0.036 mol) was dissolved into 100 ml of acetonitrile, 3-trichloromethyl phenylpiperazine (6.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 7.3 g compound (I-57) with a yield of 60.6%. ESI-MS $[M+H]^+$: m/z 402.2.

Example 58

Preparation of 6-cyano-1-(4-(4-(3-chlorophenyl) piperazine-1-yl)butyl)-1H-indole (I-58)

6-cyano-1H-indole (14.2 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 13.9 g of 6-cyano-1-(4-chlorobutyl)-1H-indole, with a yield of 60.3%.

6-cyano-1-(4-chlorobutyl)-1H-indole (8.35 g, 0.036 mol) was dissolved into 100 ml of acetonitrile, 3-trichloro phenylpiperazine (6.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 6.9 g compound (I-58) with a yield of 62.3%. ESI-MS $[M+H]^+$: m/z 393.2.

Example 59

Preparation of 1-(3-(4-(3-trifluoromethylphenyl) piperazine-1-yl)propyl)-1H-benzopyrazole (I-59)

1H-benzopyrazole (11.8 g, 0.10 mol) was dissolved into 200 ml of 20% wt. sodium hydroxide, 3-chlorobromopropane (31.2 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 11.5 g of 1-(3-chloropropyl)-1H-benzopyrazole, with a yield of 59.3%.

1-(3-chloropropyl)-1H-benzopyrazole (6.98 g, 0.036 mol) was dissolved into 100 ml of acetonitrile, 3-trifluoromethyl phenyl piperazine (6.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral $Al_2O_3$, eluted with dichloromethane/methanol mixture to produce 7.6 g compound (I-59) with a yield of 63.1%. ESI-MS $[M+H]^+$: m/z 389.2.

Example 60

Preparation of 6-cyano-1-(3-(4-(2,3-fluorophenyl) piperazine-1-yl)propyl)-1H-benzopyrazole (I-60)

6-cyano-1H-benzopyrazole (14.3 g, 0.10 mol) was dissolved into 200 ml of 20% wt. sodium hydroxide, 3-chlorobromopropane (31.2 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 13.9 g of 6-cyano-1-(3-chloropropyl)-1H-benzopyrazole, with a yield of 63.8%.

6-cyano-1-(3-chloropropyl)-1H-benzimidazole (7.88 g, 0.036 mol) was dissolved into 100 ml of acetonitrile, 2,3-dicholoro phenylpiperazine (6.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 7.6 g compound (I-60) with a yield of 61.1%. ESI-MS $[M+H]^+$: m/z 414.1.

Example 61

The said compounds (I-61 to I-65) in this invention were prepared according to the method described in applying patent US20100329978A1.

Example 62

The said compounds (I-66 to I-83) in this invention were prepared according to the method described in China patent 200610097269.1.

Example 63

Preparation of N-(3-(1H-benzotriazole-1-yl)propyl)-4-(3-benzisoxazolyl)piperidine (I-84)

Benzotriazole (11.9 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted and separated with dichlormethane to produce 16.0 g of 1-(3-chloropropyl)-1H-benzotriazole, with a yield of 82%.

1-(3-chloropropyl)-1H-benzotriazole (11.7 g, 0.06 mol) was dissolved into 150 ml of acetonitrile, 3-(piperidine-4-yl)benzisoxazole (10.1 g, 0.05 mol), diisopropylethylamine (25.8 g, 0.02 mol) and potassium iodide (8.3 g, 0.05 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 12.6 g compound (I-84) with a yield of 69.7%. ESI-MS $[M+H]^+$: m/z 362.2.

Example 64

Preparation of N-(3-(1H-benzotriazole-1-yl)propyl) 4-(3-(6-fluoro benzisoxazolyl))piperidine (I-85)

The method described in Example 63 was adopted to prepare 1-(3-chloropropyl)-1H-benzotriazole.

1-(3-chloropropyl)-1H-benzotriazole (11.7 g, 0.06 mol) was dissolved into 150 ml of acetonitrile, 6-fluoro-3-(piperidine-4-yl)benzisoxazole (11.0 g, 0.05 mol), diisopropylethylamine (25.8 g, 0.02 mol) and potassium iodide (8.3 g, 0.05 mol) were respectively added. The mixture was stirred and mixed for 10 min at ambient temperature, then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.47 g N-(3-(1H-benzotriazole-1-yl)propyl)4-(3-(6-fluoro benzisoxazolyl)) piperidine (I-85) with a yield of 71.0%. ESI-MS $[M+H]^+$: m/z 380.2.

Example 65

Preparation of N-(3-(1H-benzotriazole-1-yl)propyl)-4-(3-(6-methyl benzisoxazolyl))piperidine (I-86)

1-(3-chloropropyl)-1H-benzotriazole (11.7 g, 0.06 mol) was dissolved into 150 ml of acetonitrile, 6-methyl-3-(piperidine-4-yl)benzisoxazole (10.8 g, 0.05 mol), diisopropylethylamine (25.8 g, 0.02 mol) and potassium iodide (8.3 g, 0.05 mol) were respectively added. The mixture was stirred and mixed for 10 min at ambient temperature, then heated and refluxed to react for 15 hours. After treatment according to common method three for synthesis produced 12.4 g compound (I-86), with a yield of 66.1%. ESI-MS $[M+H]^+$: m/z 376.2.

Example 66

Preparation of N-(3-(1H-benzotriazole-1-yl)propyl)-4-(3-(6-methoxyl benzisoxazolyl))piperidine (I-87)

1-(3-chloropropyl)-1H-benzotriazole (11.7 g, 0.06 mol) was dissolved into 150 ml of acetonitrile, 6-methoxyl-3-(piperidine-4-yl)benzisoxazole (11.6 g, 0.05 mol), diisopropylethylamine (25.8 g, 0.02 mol) and potassium iodide (8.3 g, 0.05 mol) were respectively added. The mixture was stirred and mixed for 10 min at ambient temperature, then heated and refluxed to react for 15 hours. After treatment according to common method three for synthesis produced 13.3 g compound (I-87), with a yield of 67.7%. ESI-MS $[M+H]^+$: m/z 392.2.

Example 67

Preparation of N-(3-(6-fluoro-1H-benzotriazole-1-yl) propyl)-4-(3-(6-fluoro benzisoxazolyl))piperidine (I-88)

Preparation of 1-(3-chloro propyl)-6-fluoro-1H-benzotriazole 6-fluoro-1H-benzotriazole (13.7 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 6.9 g of 1-(3-chloropropyl)-6-fluoro-1H-benzotriazole, with a yield of 32.3%.

Preparation of N-(3-(6-fluoro-1H-benzotriazole-1-yl) propyl)-4-(3-(6-fluoro benzisoxazolyl))piperidine (I-88)

1-(3-chloropropyl)-6-fluoro-1H-benzotriazole (6.41 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.3 g compound (I-88), with a yield of 69.6%. ESI-MS $[M+H]^+$: m/z 398.2.

Example 68

Preparation of N-(3-(6-chloro-1H-benzotriazole-1-yl)propyl)-4-(3-(6-fluoro benzisoxazolyl))piperidine (I-89)

Preparation of 1-(3-chloro propyl)-6-chloro-1H-benzotriazole 6-chloro-1H-benzotriazole (15.4 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.3 g of 1-(3-chloropropyl)-6-chloro-1H-benzotriazole, with a yield of 31.7%.

Preparation of N-(3-(6-chloro-1H-benzotriazole-1-yl)propyl)-4-(3-(6-fluoro benzisoxazolyl))piperidine (I-89)

1-(3-chloropropyl)-6-chloro-1H-benzotriazole (6.90 g, 0.03 mol) was dissolved into 150 ml of acetonitrile, 6-fluoro- 3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.1 g compound (I-89), with a yield of 65.2%. ESI-MS [M+H]$^+$: m/z 414.1.

Example 69

Preparation of N-(3-(6-methyl-1H-benzotriazole-1-yl)propyl)-4-(3-(6-fluoro benzisoxazolyl))piperidine (I-90)

Preparation of 1-(3-chloro propyl)-6-methyl-1H-benzotriazole 6-methyl-1H-benzotriazole (13.3 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.2 g of 1-(3-chloropropyl)-6-methyl-1H-benzotriazole, with a yield of 34.3%.

Preparation of N-(3-(6-methyl-1H-benzotriazole-1-yl)propyl)-4-(3-(6-fluoro benzisoxazolyl))piperidine (I-90)

1-(3-chloropropyl)-6-methyl-1H-benzotriazole (6.29 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.5 g compound (I-90), with a yield of 71.9%. ESI-MS [M+H]$^+$: m/z 394.2.

Example 70

Preparation of N-(3-(6-methoxyl-1H-benzotriazole-1-yl)propyl)-4-(3-(6-fluoro benzisoxazolyl))piperidine (I-91)

Preparation of 1-(3-chloro propyl)-6-methoxyl-1H-benzotriazole 6-methoxyl-1H-benzotriazole (14.9 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.7 g of 1-(3-chloropropyl)-6-methoxyl-1H-benzotriazole, with a yield of 34.1%.

Preparation of N-(3-(6-methoxyl-1H-benzotriazole-1-yl)propyl)-4-(3-(6-fluoro benzisoxazolyl))piperidine (I-91)

1-(3-chloropropyl)-6-methoxyl-1H-benzotriazole (6.77 g, 0.03 mol) was dissolved into 150 ml of acetonitrile, -6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.6 g compound (I-91), with a yield of 70.0%. ESI-MS [M+H]$^+$: m/z 410.2.

Example 71

Preparation of N-(3-(6-formoxyl-1H-benzotriazole-1-yl)propyl)-4-(3-(6-fluoro benzisoxazolyl))piperidine (I-92)

Preparation of 1-(3-chloro propyl)-6-formoxyl-1H-benzotriazole 6-formoxyl-1H-benzotriazole (16.2 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.9 g of 1-(3-chloropropyl)-6-formoxyl-1H-benzotriazole, with a yield of 33.2%.

Preparation of N-(3-(6-formoxyl-1H-benzotriazole-1-yl)propyl)-4-(3-(6-fluoro benzisoxazolyl))piperidine (I-92)

1-(3-chloropropyl)-6-formoxyl-1H-benzotriazole (7.13 g, 0.03 mol) was dissolved into 150 ml of acetonitrile, -6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 15 hours. After treatment according to common method three for synthesis produced 7.5 g compound (I-92), with a yield of 73.6%. ESI-MS [M+H]$^+$: m/z 408.2.

Example 72

Preparation of N-(3-(1H-benzotriazole-1-yl) propyl)-4-(3-(6-fluoro benzisoxazolyl)) piperidine hydrochlorate (II-85)

Compound (I-85) (11.38 g, 0.03 mol) was dissolved in 100 ml of ethyl acetate and 10 ml of anhydrous ethanol. Under cooling conditions of icy water bath, 3 mol/L hydrogen chloride/ethyl acetate solution is dripped, and the pH value is adjusted to 2. The mixture is stirred for 10 min, filtered and dried to produce 11.4 g solid compound (II-85) with a yield of 91.2%.

Example 73

Preparation of N-(3-(6-methoxyl benzotriazolyl) propyl)-4-(3-benzisoxazolyl)piperidine (I-93)

Preparation of N-(3-chloro propyl)-6-methoxyl-benzotriazole 6-methoxyl-1H-benzotriazole (14.9 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.7 g of N-(3-chloropropyl)-6-methoxyl-benzotriazole, with a yield of 34.1%.

N-(3-chloropropyl)-6-methoxyl benzotriazole (0.06 mol) was dissolved into 150 ml of acetonitrile, 4-(3-benzisoxazolyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.14 g N-(3-(6-methoxyl benzotriazolyl)propyl)-4-(3-benzisoxazolyl)piperidine (I-93) with a yield of 67.2%. ESI-MS $[M+H]^+$: m/z 391.2.

Example 74

Preparation of N-(2-(1-benzotriazolyl)ethyl)-4-(3-(6-fluoro benzisoxazolyl))piperidine (I-94)

The method described in Example 63 was adopted to prepare 1-(3-chloropropyl)-1H-benzotriazole.

1-(3-chloropropyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.67 g N-(2-(1-benzotriazolyl)ethyl)-4-(3-(6-benzisoxazolyl)) piperidine (I-94) with a yield of 69.4%. ESI-MS $[M+H]^+$: m/z 365.2.

Example 75

Preparation of N-(4-(1-benzotriazolyl)butyl)-4-(3-(6-fluoro benzisoxazolyl))piperidine (I-95)

Benzotriazole (11.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.0 g of 1-(4-chlorobutyl)-1H-benzotriazole, with a yield of 81.0%.

1-(4-chlorobutyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.96 g N-(4-(1-benzotriazolyl) butyl)-4-(3-(6-benzisoxazolyl)) piperidine (I-95) with a yield of 71.0%. ESI-MS $[M+H]^+$: m/z 393.2.

Example 76

Preparation of N-(4-(6-cyano benzotriazolyl)butyl)-4-(3-(6-fluoro benzisoxazolyl))piperidine (I-96)

Preparation of 1-(3-chloro butyl)-6-cyano-1H-benzotriazole 6-cyano-1H-benzotriazole (15.9 g, 0.10 mol) is dissolved into 100 ml of 30% wt. sodium hydroxide, 3-chlorobromobutane (32.6 g, 0.10 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 9.1 g of 1-(3-chlorobutyl)-6-cyano-1H-benzotriazole, with a yield of 32.6%.

N-(3-chlorobutyl)-6-cyano benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 15.07 g N-(4-(6-cyano benzotriazolyl)butyl)-4-(3-(6-benzisoxazolyl)) piperidine (I-96) with a yield of 72.1%. ESI-MS $[M+H]^+$: m/z 418.2.

Example 77

Preparation of N-(4-(6-cyano benzotriazolyl)butyl)-4-(3-(6-methoxyl benzisoxazolyl))piperidine (I-97)

The method described in Example 76 was adopted to prepare N-(3-chlorobutyl)-6-cyano benzotriazole.

N-(3-chlorobutyl)-6-cyano benzotriazole (0.06 mol) was dissolved into 150 ml of acetonitrile, 4-(3-(6-methoxyl benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 15.01 g N-(4-(6-cyano benzotriazolyl)butyl)-4-(3-(6-methoxyl benzisoxazolyl))piperidine (I-97) with a yield of 69.8%. ESI-MS $[M+H]^+$: m/z 430.2.

Example 78

Preparation of N-(2-(6-methoxyl benzotriazolyl) ethoxyl)-4-(3-(6-fluoro benzisoxazolyl))piperidine (I-98)

The method described in common method four for synthesis was adopted to prepare N-hydroxyl-methoxyl benzotriazole.

The compound was prepared by using the methods for synthesis and after treatment with N-hydroxyl-6-methoxyl benzotriazole as the material. N-(2-chloro ethoxyl-6-methoxyl benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 14.21 g N-(2-(6-methoxyl benzotriazolyl)ethoxyl)-4-(3-(6-fluoro benzisoxazolyl))piperidine (I-98) with a yield of 69.1%. ESI-MS [M+H]$^+$: m/z 411.2.

Example 79

Preparation of N-(2-(1-benzotriazolyl)ethoxyl)-4-(3-(6-fluoro benzisoxazolyl))piperidine (I-99)

The method described in common method four for synthesis was adopted to prepare N-hydroxyl benzotriazole.

The compound was prepared by using the methods for synthesis and after treatment with N-hydroxyl benzotriazole as the material. N-(2-chloro ethoxyl benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.88 g N-(2-(1-benzotriazolyl)ethoxyl)-4-(3-(6-fluoro benzisoxazolyl))piperidine (I-99) with a yield of 67.6%. ESI-MS [M+H]$^+$: m/z 381.2.

Example 80

Preparation of N-(3-(6-methoxyl benzotriazolyl) propyl)-4-(3-benzisothiazolyl)piperidine (I-100)

The method described in Example 73 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-benzisothiazolyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.17 g N-(3-(6-methoxyl benzotriazolyl)propyl)-4-(3-benzisothiazolyl)piperidine (I-100) with a yield of 69.1%. ESI-MS [M+H]$^+$: m/z 426.2.

Example 81

Preparation of N-(3-(6-methoxyl benzotriazolyl) propyl)-4-(3-benzopyrazol)piperidine (I-101)

The method described in Example 73 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-benzopyrazol) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.11 g N-(3-(6-methoxyl benzotriazolyl)propyl)-4-(3-benzopyrazol)piperidine (I-101) with a yield of 66.5%. ESI-MS [M+H]$^+$: m/z 409.2.

Example 82

Preparation of N-(3-(6-methoxyl benzotriazolyl) propyl)-4-(3-benzofuranyl)piperidine (I-102)

The method described in Example 73 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-benzofuranyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.40 g N-(3-(6-methoxyl benzotriazolyl)propyl)-4-(3-benzofuranyl)piperidine (I-102) with a yield of 68.1%. ESI-MS [M+H]$^+$: m/z 409.2.

Known synthesis approach from current techniques could be referred to prepare relevant compound, e.g., method described in China patent 200810207606.7 could be used to prepare compound (I-103 to I-106).

Example 83

Preparation of N-(4-(1H-benzimidazoyl-1-yl)butyl)-4-(3-chlorophenyl)piperidine (I-107)

1H-benzimidazole (11.8 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 12.5 g of 1-(4-chlorobutyl)-1H-benzimidazole, with a yield of 60.0%.

1-(4-chlorobutyl)-1H-benzimidazole (7.51 g, 0.036 mol) was dissolved into 100 ml of acetonitrile, 3-trichloro phenylpiperidine (5.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 7.3 g compound (I-107) with a yield of 66.4%. ESI-MS [M+H]$^+$: m/z 368.2.

Example 84

Preparation of N-(4-(1H-benzotriazole-1-yl)butyl)-4-(3-chlorophenyl)piperidine (I-108)

Benzotriazole (11.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral Al$_2$O$_3$, and eluted with dichlormethane to produce 17.0 g of 1-(4-chlorobutyl)-1H-benzotriazole, with a yield of 81.0%.

1-(4-chlorobutyl)-1H-benzotriazole (7.55 g, 0.036 mol) was dissolved into 100 ml of acetonitrile, 3-trichloro phenylpiperidine (5.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral Al$_2$O$_3$ and purified, eluted with dichloromethane to produce 7.8 g compound (I-108) with a yield of 70.3%. ESI-MS [M+H]$^+$: m/z 369.2.

Compound (I-108) (5.55 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.4 g solid compound (II-108) with a yield of 88.0%.

Example 85

Preparation of N-(4-(1H-benzimidazoyl-1-yl)butyl)-4-(3-trifluoromethylphenyl)piperidine (I-109)

The method described in Example 63 was adopted to prepare 1-(4-chlorobutyl)-1H-benzimidazole.

1-(4-chlorobutyl)-1H-benzimidazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 11.0 g N-(4-(1H-benzimidazoyl-1-yl)butyl)-4-(3-trifluoromethylphenyl)piperidine (I-109) with a yield of 64.9%. ESI-MS [M+H]$^+$: m/z 402.2.

Compound (I-109) (6.02 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.4 g solid compound (II-109) with a yield of 89.0%.

Example 86

Preparation of N-(4-(1H-benzotriazole-1-yl)butyl)-4-(3-trifluoromethylphenyl)piperidine (I-110)

The method described in Example 64 was adopted to prepare 1-(4-chlorobutyl)-1H-benzotriazole.

1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.6 g N-(4-(1H-benzotriazole-1-yl)butyl)-4-(3-trifluoromethylphenyl)piperidine (I-110) with a yield of 67.8%. ESI-MS [M+H]$^+$: m/z 403.2.

Example 87

Preparation of N-(4-(1H-benzimidazoyl-1-yl)butyl)-4-(3-fluorophenyl)piperidine (I-111)

The method described in Example 63 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 3-trifluoro phenylpiperidine (5.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, eluted with dichloromethane/methanol mixture to produce 7.1 g compound (I-111) with a yield of 67.2%. ESI-MS [M+H]$^+$: m/z 352.2.

Example 88

Preparation of N-(4-(1H-benzimidazoyl-1-yl)butyl)-4-(2-methoxylphenyl)piperidine (I-112)

The method described in Example 63 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 2-methoxyphenyl piperidine (5.7 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral Al$_2$O$_3$, eluted with dichloromethane/methanol mixture to produce 6.7 g compound (I-112) with a yield of 61.3%. ESI-MS [M+H]$^+$: m/z 364.2.

Example 89

Preparation of N-(4-(6-fluoro-1H-benzotriazole-1-yl)butyl)-4-(3-trifluoromethylphenyl)piperidine (I-113)

6-fluoro-benzotriazole (15.3 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.0 g of 6-fluoro-1-(4-chlorobutyl)-1H-benzotriazole, with a yield of 77.0%.

6-fluoro-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.5 g N-(4-(1H-benzotriazole-1-yl)butyl)-4-(3-trifluoromethylphenyl)piperidine (I-113) with a yield of 64.1%. ESI-MS [M+H]$^+$: m/z 421.2.

Example 90

Preparation of N-(4-(6-methoxyl-1H-benzotriazole-1-yl)butyl)-4-(3-trifluoromethylphenyl)piperidine (I-114)

6-methoxyl-benzotriazole (14.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.9 g of 6-methoxyl-1-(4-chlorobutyl)-1H-benzotriazole, with a yield of 75.0%.

6-methoxyl-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 14.0 g N-(4-(1H-benzotriazole-1-yl)butyl)-4-(3-trifluoromethylphenyl)piperidine (I-114) with a yield of 64.6%. ESI-MS [M+H]+: m/z 433.2.

Example 91

Preparation of N-(4-(6-cyano-1H-benzotriazole-1-yl)butyl)-4-(3-trifluoromethylphenyl)piperidine (I-115)

6-cyano-benzotriazole (14.4 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.3 g of 6-cyano-1-(4-chlorobutyl)-1H-benzotriazole, with a yield of 74.0%.

6-cyano-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.5 g N-(4-(1H-benzotriazole-1-yl)butyl)-4-(3-trifluoromethylphenyl)piperidine (I-115) with a yield of 63.1%. ESI-MS [M+H]$^+$: m/z 427.2.

Example 92

Preparation of N-(4-(1H-benzotriazole-1-yl)propoxyl)-4-(3-trifluoromethylphenyl)piperidine (I-116)

Preparation of N-(2-chloro propoxyl)benzotriazole

Substituted 1-hydroxyl benzotriazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral $Al_2O_3$, or separated and purified by using HPLC to prepare 1-(3-chloropropoxyl)benzotriazole, with a yield of 75.0%-85.0%.

1-(3-chloropropoxyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.2 g N-(4-(1H-benzotriazole-1-yl)propoxyl)-4-(3-trifluoromethylphenyl)piperidine (I-116) with a yield of 65.3%. ESI-MS $[M+H]^+$: m/z 405.2.

Example 93

Preparation of N-(4-(1H-benzimidazole-1-yl)propoxyl)-4-(3-trifluoromethylphenyl)piperidine (I-117)

Preparation of N-(2-chloro propoxyl)benzimidazole

Substituted 1-hydroxyl benzimidazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral $Al_2O_3$, or separated and purified by using HPLC to prepare 1-(3-chloropropoxyl)benzimidazole, with a yield of 75.0%.

1-(3-chloropropoxyl)benzimidazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce N-(4-(1H-benzimidazole-1-yl)propoxyl)-4-(3-trifluoromethylphenyl)piperidine (I-117) with a yield of 67.1%. ESI-MS $[M+H]^+$: m/z 404.2.

Example 94

Preparation of N-(4-(1H-benzimidazoyl-1-yl)butyl)-4-(2-furyl)piperidine (I-118)

1H-benzimidazole (11.8 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 12.5 g of 1-(4-chlorobutyl)-1H-benzimidazole, with a yield of 60.0%.

1-(4-chlorobutyl)-1H-benzimidazole (7.51 g, 0.036 mol) was dissolved into 100 ml of acetonitrile, 4-(2-furyl) piperidine (4.6 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.0 g compound (I-118) with a yield of 61.6%. ESI-MS $[M+H]^+$: m/z 324.2.

Example 95

Preparation of N-(4-(1H-benzimidazoyl-1-yl)butyl)-4-(4-pyridyl)piperidine (I-119)

The method described in Example 94 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(4-pyridyl) piperidine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.3 g compound (I-119) with a yield of 62.1%. ESI-MS $[M+H]^+$: m/z 335.2.

Example 96

Preparation of N-(4-(1H-benzimidazoyl-1-yl)butyl)-4-(2-pyrimidinyl)piperidine (I-120)

The method described in Example 94 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-pyrimidinyl) piperidine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.1 g compound (I-120) with a yield of 60.1%. ESI-MS $[M+H]^+$: m/z 336.2.

Example 97

Preparation of N-(4-(1H-benzotriazole-1-yl)butyl)-4-(4-cyclohexyl)piperidine (I-121)

The method described in Example 64 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-cyclohexyl) piperidine (5.1 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with

Example 98

Preparation of N-(4-(1H-benzotriazole-1-yl)butyl)-4-(1-naphthyl)piperidine (I-122)

The method described in Example 64 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-naphthyl)piperidine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.9 g compound (I-122) with a yield of 60.1%. ESI-MS [M+H]$^+$: m/z 385.3.

Example 99

Preparation of N-(4-(1H-benzotriazole-1-yl)butyl)-4-(2-quinoxalinyl)piperidine (I-123)

The method described in Example 64 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(2-quinoxalinyl)piperidine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.3 g compound (I-123) with a yield of 62.7%. ESI-MS [M+H]$^+$: m/z 387.2.

Example 100

Preparation of N-(4-(1H-benzimidazoyl-1-yl)butyl)-4-(3-chlorophenyl)piperidine (I-124)

1H-benzimidazole (11.8 g, 0.10 mol) was dissolved into 200 ml of 20% wt. sodium hydroxide, 4-chlorobromobutane (34.3 g, 0.20 mol) and tetrabutyl ammonium bromide (1.0 g) were added, and mixed for 5 min. The mixture was heated to 60° C., stirred to react for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$ to produce 12.5 g of 1-(4-chlorobutyl)-1H-benzimidazole, with a yield of 60.0%.

1-(4-chlorobutyl)-1H-benzimidazole (7.51 g, 0.036 mol) was dissolved into 100 ml of acetonitrile, 3-trichloro phenylpiperidine (5.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 7.3 g compound (I-124) with a yield of 66.4%. ESI-MS [M+H]$^+$: m/z 368.2.

Example 101

Preparation of N-(4-(1H-benzotriazole-1-yl)butyl)-4-(3-chlorophenyl)piperidine (I-125)

Benzotriazole (11.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.0 g of 1-(4-chlorobutyl)-1H-benzotriazole, with a yield of 81.0%.

1-(4-chlorobutyl)-1H-benzotriazole (7.55 g, 0.036 mol) was dissolved into 100 ml of acetonitrile, 3-trichloro phenylpiperidine (5.9 g, 0.03 mol), diisopropylethylamine (15.5 g, 0.12 mol) and potassium iodide (5.0 g, 0.03 mol) were respectively added. The mixture was stirred and mixed, then heated and refluxed to react for 15 hours. The mixture was cooled down to ambient temperature and filtered. The filtrate was concentrated to produce oily products, and treated by chromatography with neutral $Al_2O_3$ and purified, eluted with dichloromethane to produce 7.8 g compound (I-125) with a yield of 70.3%. ESI-MS [M+H]$^+$: m/z 369.2.

Compound (I-124) (5.55 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.4 g solid compound (II-125) with a yield of 88.0%.

Example 102

Preparation of N-(4-(1H-benzimidazoyl-1-yl)butyl)-4-(3-trifluoromethylphenyl)piperidine (I-126)

The method described in Example 100 was adopted to prepare 1-(4-chlorobutyl)-1H-benzimidazole.

1-(4-chlorobutyl)-1H-benzimidazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 11.0 g N-(4-(1H-benzimidazoyl-1-yl)butyl)-4-(3-trifluoromethylphenyl)piperidine (I-126) with a yield of 64.9%. ESI-MS [M+H]$^+$: m/z 402.2.

Compound (I-126) (6.02 g, 0.015 mol) was dissolved in 50 ml of ethyl acetate. Under cooling conditions of icy water bath, 3 mol/L hydrogen chloride/ethyl acetate solution is dripped, and the pH value is adjusted to 2. The mixture is stirred for 10 min, filtered and dried to produce 5.4 g solid compound (II-126) with a yield of 89.0%.

Example 103

Preparation of N-(4-(1H-benzotriazole-1-yl)butyl)-4-(3-trifluoromethylphenyl)piperidine (I-127)

The method described in Example 101 was adopted to prepare 1-(4-chlorobutyl)-1H-benzotriazole.

1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (25.8 g, 0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.6 g N-(4-(1H-benzotriazole-1-yl)butyl)-4-(3-trifluoromethylphenyl)piperidine (I-127) with a yield of 67.8%. ESI-MS [M+H]$^+$: m/z 403.2.

Example 104

Preparation of N-(4-(1H-benzimidazoyl-1-yl)butyl)-4-(3-fluorophenyl)piperidine (I-128)

The method described in Example 100 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 3-trifluoro phenylpiperidine (5.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, eluted with dichloromethane/methanol mixture to produce 7.1 g compound (I-128) with a yield of 67.2%. ESI-MS [M+H]$^+$: m/z 352.2.

Example 105

Preparation of N-(4-(1H-benzimidazoyl-1-yl)butyl)-4-(2-methoxylphenyl)piperidine (I-119)

The method described in Example 100 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 2-methoxyphenyl piperidine (5.7 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 10-15 hours. The mixture was cooled down to ambient temperature and filtered. The filtrate was concentrated to produce oily products, and treated by chromatography with neutral $Al_2O_3$, eluted with dichloromethane/methanol mixture to produce 6.7 g compound (I-129) with a yield of 61.3%. ESI-MS [M+H]$^+$: m/z 364.2.

Example 106

Preparation of N-(4-(6-fluoro-1H-benzotriazole-1-yl)butyl)-4-(3-trifluoromethylphenyl)piperidine (I-130)

6-fluoro-benzotriazole (15.3 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.0 g of 6-fluoro-1-(4-chlorobutyl)-1H-benzotriazole, with a yield of 77.0%.

6-fluoro-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.5 g N-(4-(1H-benzotriazole-1-yl)butyl)-4-(3-trifluoromethylphenyl)piperidine (I-130) with a yield of 64.1%. ESI-MS [M+H]$^+$: m/z 421.2.

Example 107

Preparation of N-(4-(6-methoxyl-1H-benzotriazole-1-yl)butyl)-4-(3-trifluoromethylphenyl)piperidine (I-131)

6-methoxyl-benzotriazole (14.9 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral $Al_2O_3$, and eluted with dichlormethane to produce 17.9 g of 6-methoxyl-1-(4-chlorobutyl)-1H-benzotriazole, with a yield of 75.0%.

6-methoxyl-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 14.0 g N-(4-(1H-benzotriazole-1-yl)butyl)-4-(3-trifluoromethylphenyl)piperidine (I-131) with a yield of 64.6%. ESI-MS [M+H]$^+$: m/z 433.2.

Example 108

Preparation of N-(4-(6-cyano-1H-benzotriazole-1-yl) butyl)-4-(3-trifluoromethylphenyl)piperidine (I-132)

6-cyano-benzotriazole (14.4 g, 0.10 mol) is dissolved into 100 ml of 30% wt. sodium hydroxide, 4-chlorobromobutane (34.3 g, 0.20 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral Al$_2$O$_3$, and eluted with dichlormethane to produce 17.3 g of 6-cyano-1-(4-chlorobutyl)-1H-benzotriazole, with a yield of 74.0%.

6-cyano-1-(4-chlorobutyl)-1H-benzotriazole (0.06 mol) was dissolved into 150 ml of acetonitrile, 4-(3-(3-trifluoromethylphenyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.5 g N-(4-(1H-benzotriazole-1-yl)butyl)-4-(3-trifluoromethylphenyl)piperidine (I-132) with a yield of 63.1%. ESI-MS [M+H]$^+$: m/z 427.2.

Example 109

Preparation of N-(4-(1H-benzotriazole-1-yl)propoxyl)-4-(3-trifluoromethylphenyl)piperidine (I-133)

Preparation of N-(2-chloro propoxyl)benzotriazole

Substituted 1-hydroxyl benzotriazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral Al$_2$O$_3$, or separated and purified by using HPLC to prepare 1-(3-chloropropoxyl)benzotriazole, with a yield of 75.0%-85.0%.

1-(3-chloropropoxyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.2 g N-(4-(1H-benzotriazole-1-yl)propoxyl)-4-(3-trifluoromethylphenyl)piperidine (I-133) with a yield of 65.3%. ESI-MS [M+H]$^+$: m/z 405.2.

Example 110

Preparation of N-(4-(1H-benzimidazole-1-yl)propoxyl)-4-(3-trifluoromethylphenyl)piperidine (I-134)

Preparation of N-(2-chloro propoxyl)benzimidazole

Substituted 1-hydroxyl benzimidazole (0.01 mol) was dissolved in 10 ml of NMP, solid paraffin mixture containing 50% (w/w) hydrogen and oxygen was added in different times, stirred to react for 0.5 h. Meanwhile, 3-bromochloropropane (0.015 mol) was dissolved in 5 ml of NMP and added into the above said solution, and stirred to react for 12 h. Reaction solution was poured into 50 ml of water, extracted with ethyl acetate (3×50 mL). Organic phases were mixed and washed with 30 ml of water. Anhydrous magnesium sulfate was added to dry organic phase, filtered, with solvent evaporated. Oily products were analyzed by chromatography with neutral Al$_2$O$_3$, or separated and purified by using HPLC to prepare 1-(3-chloropropoxyl)benzimidazole, with a yield of 75.0%.

1-(3-chloropropoxyl)benzimidazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.6 g N-(4-(1H-benzimidazole-1-yl)propoxyl)-4-(3-trifluoromethylphenyl)piperidine (I-134) with a yield of 67.1%. ESI-MS [M+H]$^+$: m/z 404.2.

Example 111

Preparation of N-(3-(1H-benzotriazole-1-yl)propyl)-4-(3-(6-methyl benzisoxazolyl))piperidine (I-135)

1-(3-chloropropyl)-1H-benzotriazole (11.7 g, 0.06 mol) was dissolved into 150 ml of acetonitrile, 6-methyl-3-(piperidine-4-yl)benzisoxazole (10.8 g, 0.05 mol), diisopropylethylamine (25.8 g, 0.02 mol) and potassium iodide (8.3 g, 0.05 mol) were respectively added. The mixture was stirred and mixed for 10 min at ambient temperature, then heated and refluxed to react for 15 hours. After treatment according to common method three for synthesis produced 12.4 g compound (I-135), with a yield of 66.1%. ESI-MS [M+H]$^+$: m/z 376.2.

Example 112

Preparation of N-(3-(1H-benzotriazole-1-yl)propyl)-4-(3-(6-methyl benzisoxazolyl))piperidine (I-136)

1-(3-chloropropyl)-1H-benzotriazole (11.7 g, 0.06 mol) was dissolved into 150 ml of acetonitrile, 6-methoxyl-3-(piperidine-4-yl)benzisoxazole (11.6 g, 0.05 mol), diisopropylethylamine (25.8 g, 0.02 mol) and potassium iodide (8.3 g, 0.05 mol) were respectively added. The mixture was stirred and mixed for 10 min at ambient temperature, then heated and refluxed to react for 15 hours. After treatment according to common method three for synthesis produced 13.3 g compound (I-136), with a yield of 67.7%. ESI-MS [M+H]$^+$: m/z 392.2.

Example 113

Preparation of N-(3-(6-fluoro-1H-benzotriazole-1-yl) propyl)-4-(3-(6-fluoro benzisoxazolyl))piperidine (I-137)

Preparation of 1-(3-chloro propyl)-6-fluoro-1H-benzotriazole 6-fluoro-1H-benzotriazole (13.7 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 6.9 g of 1-(3-chloropropyl)-6-fluoro-1H-benzotriazole, with a yield of 32.3%.

Preparation of N-(3-(6-fluoro-1H-benzotriazole-1-yl) propyl)-4-(3-(6-fluoro benzisoxazolyl))piperidine (I-137)

1-(3-chloropropyl)-6-fluoro-1H-benzotriazole (6.41 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.3 g compound (I-137), with a yield of 69.6%. ESI-MS [M+H]$^+$: m/z 398.2.

Example 114

Preparation of N-(3-(6-chloro-1H-benzotriazole-1-yl)propyl)-4-(3-(6-fluoro benzisoxazolyl))piperidine (I-138)

Preparation of 1-(3-chloro propyl)-6-chloro-1H-benzotriazole 6-chloro-1H-benzotriazole (15.4 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 7.3 g of 1-(3-chloropropyl)-6-chloro-1H-benzotriazole, with a yield of 31.7%.

Preparation of N-(3-(6-chloro-1H-benzotriazole-1-yl)propyl)-4-(3-(6-fluoro benzisoxazolyl)) piperidine (I-138)

1-(3-chloropropyl)-6-chloro-1H-benzotriazole (6.90 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.1 g compound (I-138), with a yield of 65.2%. ESI-MS [M+H]$^+$: m/z 414.1.

Example 115

Preparation of N-(3-(6-methyl-1H-benzotriazole-1-yl)propyl)-4-(3-(6-fluoro benzisoxazolyl))piperidine (I-139)

Preparation of 1-(3-chloro propyl)-6-methyl-1H-benzotriazole 6-methyl-1H-benzotriazole (13.3 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.2 g of 1-(3-chloropropyl)-6-methyl-1H-benzotriazole, with a yield of 34.3%.

Preparation of N-(3-(6-methyl-1H-benzotriazole-1-yl)propyl)-4-(3-(6-fluoro benzisoxazolyl))piperidine (I-139)

1-(3-chloropropyl)-6-methyl-1H-benzotriazole (6.29 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.5 g compound (I-139), with a yield of 71.9%. ESI-MS [M+H]$^+$: m/z 394.2.

Example 116

Preparation of N-(3-(6-methoxyl-1H-benzotriazole-1-yl)propyl)-4-(3-(6-fluoro benzisoxazolyl))piperidine (I-140)

Preparation of N-(3-chloro propyl)-6-methoxyl-benzotriazole 6-methoxyl-1H-benzotriazole (14.9 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.7 g of N-(3-chloropropyl)-6-methoxyl-benzotriazole, with a yield of 34.1%.

Preparation of N-(3-(6-methoxyl-1H-benzotriazole-1-yl)propyl)-4-(3-(6-fluoro benzisoxazolyl))piperidine (I-140)

1-(3-chloropropyl)-6-methoxyl-1H-benzotriazole (6.77 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 16 hours. After treatment according to common method three for synthesis produced 8.6 g compound (I-140), with a yield of 70%. ESI-MS [M+H]$^+$: m/z 410.2.

Example 117

Preparation of N-(3-(6-formoxyl-1H-benzotriazole-1-yl)propyl)-4-(3-(6-fluoro benzisoxazolyl))piperidine (I-141)

Preparation of 1-(3-chloro propyl)-6-formoxyl-1H-benzotriazole 6-formoxyl-1H-benzotriazole (16.2 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Post treatment was performed based on common method two for synthesis. The solution was separated and purified by HPLC to produce 7.9 g of 1-(3-chloropropyl)-6-formoxyl-1H-benzotriazole, with a yield of 33.2%.

Preparation of N-(3-(6-formoxyl-1H-benzotriazole-1-yl)propyl)-4-(3-(6-fluoro benzisoxazolyl))piperidine (I-141)

1-(3-chloropropyl)-6-formoxyl-1H-benzotriazole (7.13 g, 0.03 mol) was dissolved into 150 ml of acetonitrile, 6-fluoro-3-(piperidine-4-yl)benzisoxazole (5.5 g, 0.025 mol), diisopropylethylamine (12.9 g, 0.1 mol) and potassium iodide (4.15 g, 0.025 mol) were respectively added. The mixture was stirred and mixed for 10 min at ambient temperature, then heated and refluxed to react for 15 hours. After treatment according to common method three for synthesis produced 7.5 g compound (I-141), with a yield of 73.6%. ESI-MS [M+H]$^+$: m/z 408.2.

Example 118

Preparation of N-(3-(6-methoxyl benzotriazolyl) propyl)-4-(3-benzisoxazolyl)piperidine (I-142)

The method described in Example 116 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-benzisoxazolyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.14 g N-(3-(6-methoxyl benzisoxazolyl) propyl)-4-(3-benzisothiazolyl) piperidine (I-142) with a yield of 67.2%. ESI-MS [M+H]$^+$: m/z 391.2.

Example 119

Preparation of N-(2-(1-benzotriazolyl)ethyl)-4-(3-(6-fluoro benzisoxazolyl))piperidine (I-143)

Benzotriazole (11.9 g, 0.10 mol) is dissolved into 100 ml of 30% wt. sodium hydroxide, 3-chlorobromopropane (31.4 g, 0.10 mol), tetrabutyl ammonium bromide (0.8 g) are added, and mixed for 5 min. The reaction solution is gradually heated to 60° C., stirred for reaction for 2 hours. Then the reaction solution was cooled down to ambient temperature, 100 ml of dichloromethane was added for extraction and liquid separation. To the aqueous phase, 100 of dichloromethane was added for extraction. Organic phases were mixed, washed with 100 ml of saturated saline. Liquid was separated, and organic phase was evaporated to dryness to produce oily product. Oily products were separated and purified by chromatography with neutral Al$_2$O$_3$, and eluted and separated with dichlormethane to produce 16.0 g of 1-(3-chloropropyl)-1H-benzotriazole, with a yield of 82.0%.

1-(3-chloropropyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 12.67 g N-(2-(1-benzotriazolyl)ethyl)-4-(3-(6-fluoro benzisoxazolyl))piperidine (I-143) with a yield of 69.4%. ESI-MS [M+H]$^+$: m/z 365.2.

Example 120

Preparation of N-(4-(1-benzotriazolyl)butyl)-4-(3-(6-fluoro benzisoxazolyl))piperidine (I-144)

The method described in Example 101 was adopted to prepare 1-(4-chlorobutyl)-1H-benzotriazole.

1-(4-chlorobutyl)benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral Al$_2$O$_3$, purified, eluted with dichloromethane/methanol mixture to produce 13.96 g N-(4-(1-benzotriazolyl)butyl)-4-(3-(6-fluoro benzisoxazolyl))piperidine (I-144) with a yield of 71.0%. ESI-MS [M+H]$^+$: m/z 393.2.

Example 121

Preparation of N-(4-(6-cyano benzotriazolyl)butyl)-4-(3-(6-fluoro benzisoxazolyl))piperidine (I-145)

Preparation of 1-(3-chloro butyl)-6-cyano-1H-benzotriazole 6-cyano-1H-benzotriazole (15.9 g, 0.10 mol) is dissolved into 100 ml of 30% wt. sodium hydroxide, 3-chlorobromobutane (32.6 g, 0.10 mol), tetrabutyl ammonium bromide (0.8 g) are added, and mixed for 5 min. The reaction solution is gradually heated to 60° C., stirred for reaction for 2 hours. Post treatment was performed based on common method one for synthesis. The solution was separated and purified by HPLC to produce 9.1 g of 1-(3-chlorobutyl)-6-cyano-1H-benzotriazole, with a yield of 32.6%.

1-(3-chlorobutyl)-6-cyano benzotriazole (0.06 mol) was dissolved into 150 ml of acetonitrile, 4-(3-(6-fluoro benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 15.07 g N-(4-(6-cyanobenzotriazolyl)butyl)-4-(3-(6-fluoro benzisoxazolyl))piperidine (I-145) with a yield of 72.1%. ESI-MS [M+H]$^+$: m/z 418.2.

Example 122

Preparation of N-(4-(6-cyano benzotriazolyl)butyl)-4-(3-(6-methoxyl benzisoxazolyl))piperidine (I-146)

The method described in Example 121 was adopted to prepare 1-(3-chlorobutyl)-6-cyano benzotriazole.

1-(3-chlorobutyl)-6-cyano benzotriazole (0.06 mol) was dissolved into 150 ml of acetonitrile, 4-(3-(6-methoxyl benzisoxazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 15.01 g N-(4-(6-cyanobenzotriazolyl)butyl)-4-(3-(6-methoxyl benzisoxazolyl))piperidine (I-146) with a yield of 69.8%. ESI-MS [M+H]$^+$: m/z 430.2.

Example 123

Preparation of N-(2-(6-methoxyl benzotriazolyl) ethoxyl)-4-(3-benzisoxazolyl)piperidine (I-147)

The method described in common method four for synthesis was adopted to prepare N-hydroxyl-methoxyl benzotriazole.

The compound was prepared by using the methods for synthesis and after treatment with N-hydroxyl-6-methoxyl benzotriazole as the material. N-(2-chloro ethoxyl-6-methoxyl benzotriazole (0.06 mol) was dissolved into 150 ml of acetonitrile, 4-(3-benzisoxazolyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 14.21 g N-(2-(6-methoxyl benzisoxazolyl) ethoxyl)-4-(3-benzisothiazolyl) piperidine (I-147) with a yield of 69.1%. ESI-MS [M+H]$^+$: m/z 394.2.

Example 124

Preparation of N-(2-(1-benzotriazolyl)ethyl)-4-(3-fluoro benzisoxazolyl) piperidine (I-148)

The method described in common method four for synthesis was adopted to prepare N-hydroxyl benzotriazole.

The compound was prepared by using the methods for synthesis and after treatment with N-hydroxyl benzotriazole as the material. N-(2-chloro ethoxyl benzotriazole (0.06 mol) was dissolved into 150 ml of acetonitrile, 4-(3-benzisoxazolyl) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.88 g N-(2-(1-benzisoxazolyl) ethoxyl)-4-(3-fluoro benzisothiazolyl) piperidine (I-148) with a yield of 67.6%. ESI-MS [M+H]$^+$: m/z 364.2.

Example 125

Preparation of N-(3-(6-methoxyl benzotriazolyl) propyl)-4-(3-(6-fluoro benzisothiazolyl))piperidine (I-149)

The method described in Example 116 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-(6-fluoro benzisothiazolyl)) piperidine (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 13.17 g N-(3-(6-methoxyl benzotriazolyl)propyl)-4-(3-(6-fluoro benzisothiazolyl))piperidine (I-149) with a yield of 69.1%. ESI-MS [M+H]$^+$: m/z 426.1.

Example 126

Preparation of N-(3-(6-methoxyl benzotriazolyl) propyl)-4-(3-(6-fluoro benzopyrazol))piperidine (I-150)

The method described in Example 116 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-(6-fluoro benzisothiazole)) (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.11 g N-(3-(6-methoxyl benzotriazolyl)propyl)-4-(3-(6-fluoro benzopyrazol))piperidine (I-150) with a yield of 66.5%. ESI-MS [M+H]$^+$: m/z 409.2.

Example 127

Preparation of N-(3-(6-methoxyl benzotriazolyl) propyl)-4-(3-(6-fluoro benzofuranyl))piperidine (I-151)

The method described in Example 116 was adopted to prepare N-(3-chloropropyl)-6-methoxyl benzotriazole.

N-(3-chloropropyl)-6-methoxyl benzotriazole (0.06 mol) was dissolved into 150 ml of acetonitrile, 4-(3-(6-fluoro benzisothiazole)) (0.05 mol), diisopropylethylamine (0.2 mol) and potassium iodide (0.05 mol) were respectively added. The mixture was stirred for 10 min at ambient temperature, and then heated and refluxed to react for 15 hours. The mixture was cooled down to ambient temperature and filtered. The filtrate was concentrated to produce oily products, and treated by chromatography with neutral $Al_2O_3$, purified, eluted with dichloromethane/methanol mixture to produce 12.40 g N-(3-(6-methoxyl benzotriazolyl)propyl)-4-(3-(6-fluoro benzofuranyl))piperidine (I-151) with a yield of 68.1%. ESI-MS $[M+H]^+$: m/z 409.2.

Example 128

Preparation of N-(4-(1H-benzimidazoyl-1-yl)butyl)-4-(2-furyl)piperidine (I-152)

The method described in Example 100 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-furyl) piperidine (4.6 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.0 g compound (I-152) with a yield of 61.6%. ESI-MS $[M+H]^+$: m/z 324.2.

Example 129

Preparation of N-(4-(1H-benzimidazoyl-1-yl)butyl)-4-(4-pyridyl)piperidine (I-153)

The method described in Example 100 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(4-pyridyl) piperidine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.3 g compound (I-153) with a yield of 62.1%. ESI-MS $[M+H]^+$: m/z 335.2.

Example 130

Preparation of N-(4-(1H-benzimidazoyl-1-yl)butyl)-4-(2-pyrimidinyl)piperidine (I-154)

The method described in Example 100 was adopted to prepare 1-(4-chlorobutyl)-1H-benzimidazole.

1-(4-chlorobutyl)-1H-benzimidazole (7.51 g, 0.036 mol) was dissolved into 100 ml of acetonitrile, 4-(2-pyrimidinyl) piperidine (4.9 g, 0.03 mol), diisopropylethylamine (15.5 g, 0.12 mol) and potassium iodide (5.0 g, 0.03 mol) were respectively added. The mixture was stirred for 10 min at ambient temperature, and then heated and refluxed to react for 20 hours. The mixture was cooled down to ambient temperature and filtered. The filtrate was concentrated to produce oily products, and treated by chromatography with neutral $Al_2O_3$, eluted with dichloromethane/methanol mixture to produce 6.1 g compound (I-154) with a yield of 60.1%. ESI-MS $[M+H]^+$: m/z 336.2.

Example 131

Preparation of N-(4-(1H-benzotriazole-1-yl)butyl)-4-cyclohexyl piperidine (I-155)

The method described in Example 101 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-cyclohexyl) piperidine (5.1 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.5 g compound (I-155) with a yield of 63.7%. ESI-MS $[M+H]^+$: m/z 341.3.

Example 132

Preparation of N-(4-(1H-benzotriazole-1-yl)butyl)-4-(1-naphthyl)piperidine (I-156)

The method described in Example 101 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(1-naphthyl)piperidine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 6.9 g compound (I-156) with a yield of 60.1%. ESI-MS $[M+H]^+$: m/z 385.3.

Example 133

Preparation of N-(4-(1H-benzotriazole-1-yl)butyl)-4-(2-quinoxalinyl)piperidine (I-157)

The method described in Example 101 was adopted to prepare 1-(4-chlorobutyl)-1H-benzotriazole.

1-(4-chlorobutyl)-1H-benzotriazole (7.55 g, 0.036 mol) was dissolved into 100 ml of acetonitrile, 4-(2-quinoxalinyl) piperidine (6.4 g, 0.03 mol), diisopropylethylamine (15.5 g, 0.12 mol) and potassium iodide (5.0 g, 0.03 mol) were respectively added. The mixture was stirred and mixed, then heated and refluxed to react for 20 hours. The mixture was cooled down to ambient temperature and filtered. The filtrate was concentrated to produce oily products, and treated by chromatography with neutral $Al_2O_3$ and purified, eluted with dichloromethane to produce 7.3 g compound (I-157) with a yield of 62.7%. ESI-MS $[M+H]^+$: m/z 387.2.

Example 134

Relaxing effects of compound II-1 to II-60 and II-84 to II-157 on vascular smooth muscle constricted by convulsant in vitro 1. Experimental Animals:

Rabbits, male or female, 2.0-3.0 kg, were provided by Experimental Animal Center, China Medical university.

2. Drugs and Reagents

Compound II-1 to II-60 and II-84 to II-157, i.e., salts (hydrochlorates) prepared by using the above methods, were used for the following experiments.

Sodium chloride (NaCl): bought from Tianjin Damao Chemical Reagent Factory, batch number 20120413.

Kalium chloride (NaCl): bought from Tianjin Damao Chemical Reagent Factory, batch number 20111123.

Anhydrous magnesium sulfate ($MgSO_4$): bought from Tianjin Damao Chemical Reagent Factory, batch number 20101029.

Anhydrous calcium chloride ($CaCl_2$): bought from Tianjin Damao Chemical Reagent Factory, batch number 20110314.

Sodium bicarbonate ($NaHCO_3$): bought from Tianjin Damao Chemical Reagent Factory, batch number 20120507.

Glucose: bought from Tianjin Damao Chemical Reagent Factory, batch number 20120512.

Kalium dihydrogen phosphate ($KH_2PO_4$): bought from Tianjin Damao Chemical Reagent Factory, batch number 20110928.

Sodium chloride injection (NaCl): bought from Shenyang Zhiying Pharmaceutical Factory, batch number: 12021001.

Epinephrine hydrochloride injection: strength: 1 mg/1 ml, bought from Grandpharma (China) Co., Ltd., batch number: 120105.

Norepinephrine bitartrate injection: strength: 2 mg/1 ml, bought from Grandpharma (China) Co., Ltd., batch number: 120304.

3. Experimental Instruments

HSS-1(B) thermostat bath: Chengdu Instrument Factory.

RM6240B multi-channel physiological signal collection & processing system: Chengdu Instrument Factory.

JZJ01 muscular strength transducer: Chengdu Instrument Factory.

YPJ01 pressure transducer: Chengdu Instrument Factory.

TG-328A photoelectric analytical balance: Shanghai Balance Factory.

T-500 electronic balance: Chuangshu Shuangjie Test Instrument Factory.

Micropipette: Shanghai Rongtai Biochemical Engineering Co., Ltd.

electrical heated thermostatic water bath: Tianjin Taisite Instrument Co., Ltd.

4. Preparation of Nutrient Solution

Krebs-Henseleit (K-H) normal saline: NaCl 6.92 (concentration unit), KCl 0.35, $MgSO_4$ 0.29, $KH_2PO_4$ 0.16, $CaCl_2$ 0.28, $NaHCO_3$ 2.1, Glucose 2.0 (g/L), pH 7.2.

High kalium solution: removing equal mole of NaCl from K-H solution, adding KCl to prepare modified K-H solution containing $K^+$ 60 mmol/L.

K-H free solution: removing $CaCl_2$ from K-H solution, adding equal mole of KCl and $EDTA^{-2}Na^+$ 0.1 mmol/L, other components not changed.

Calcium free high kalium solution: removing $CaCl_2$ from high kalium solution, adding equal mole of KCl and $EDTA^{-2}Na^+$ 0.1 mmol/L, other components not changed.

Preparation of compound II-1 to II-60 and II-84 to II-157 solutions: weigh appropriate amount of compound sample, dilute to solutions of series concentrations with distilled water ($10^{-10}$-$10^{-2}$ mol/L) for later use.

5. Preparation of Excised Vascular Smooth Muscle Sample from Rabbits

Rabbits were hit to be dizzy, with thoracic cavity quickly cut open, descending aorta exposed, connective tissues and surrounding fatty tissues (for hydroxytryptamine receptor antagonism test, endothelia should be removed with smooth stainless steel rod) removed, the aorta was cut into 3-5 mm vascular rings which were penetrated together with a steel wire with one end fixed on ventilation hook, another end on pressure tonotransducer. The aorta rings were put into a bath tube with 20 ml of nutritional solution, and the tension changes were recorded by using the recorder. The temperature of bath tube was maintained at 37±0.5° C., and mixed gas (95% $O_2$+5% $CO_2$) was ventilated at a rate of I-2 bubbles/second. The initial load of the sample was 1.5 g, nutritional solution was changed for every 20 min. The sample was balanced for 2 hours, and the experiment would be started when baseline became stable.

6. Specific Experimental Procedure and Results 6.1 Relaxing Effects of Compound II-1 to II-60 and II-84 to II-157 on Vascular Smooth Muscle Constricted by Convulsant Adrenaline Hydrochloride (AD) In Vitro After sample tension became stable, a piece of waveform was recorded. Adrenaline hydrochloride (AD) ($10^{-5}$ mol/L) was added into a bath tube to induce constriction, when maximal constriction was achieved, the sample was completely flushed, K-H solution was changed for every 20 min. Contents in the tube was balanced for 60 min, when baseline recovered to be stable, the convulsant was added at the same concentration to induce constriction. When the later maximal constriction response was basically consistent with the former one, the prepared compound solutions were subsequently added, including compound II-1 to II-60 solutions ($1\times10^{-8}$-$1\times10^{-3}$ mol/L), compound II-84 to II-123 solutions ($1\times10^{-10}$-$1\times10^{-2}$ mol/L) and compound II-124 to II-157 solutions ($1\times10^{-10}$~$1\times10^{-3}$ mol/L), to record the waveforms. Relaxing percentage of the compound was used as Y axis, maximal relaxation response was 100%, negative logarithm of different concentration was used as X axis, to draw dose effect curve (expressed in mean±SEM (—•—), n=5). Compounds II-2 and II-3 had the most obvious relaxing effects (FIG. 1 and FIG. 8).

From FIG. 1 and FIG. 8, compounds II-2 and II-3 had relaxing effects on samples constricted by AD in certain dose dependent manner. The $-\log EC_{50}$ value was 5.73±0.03 for compound II-2 to relax adrenaline constricted rabbit aorta, and 6.01±0.05 for compound II-3.

Compound II-31 also had relatively obvious relaxing effects, negative logarithms of different concentrations were used as X axis to draw dose effective curves, which were shown in FIG. 10. II-29 also had obvious relaxing effects, and its dose effect curve was shown in FIG. 15. From FIG. 10, compound II-31 had relaxing effects on samples constricted by AD in certain dose dependent manner. The $-\log EC_{50}$ value was 6.19±0.03 for compound II-31 to relax AD constricted rabbit aorta. Similarly, the relaxing effects of compound II-29 against AD was also in a dose dependent manner. The $-\log EC_{50}$ value was 6.01±0.02 for compound II-29 to relax AD constricted rabbit aorta.

Figure 17:
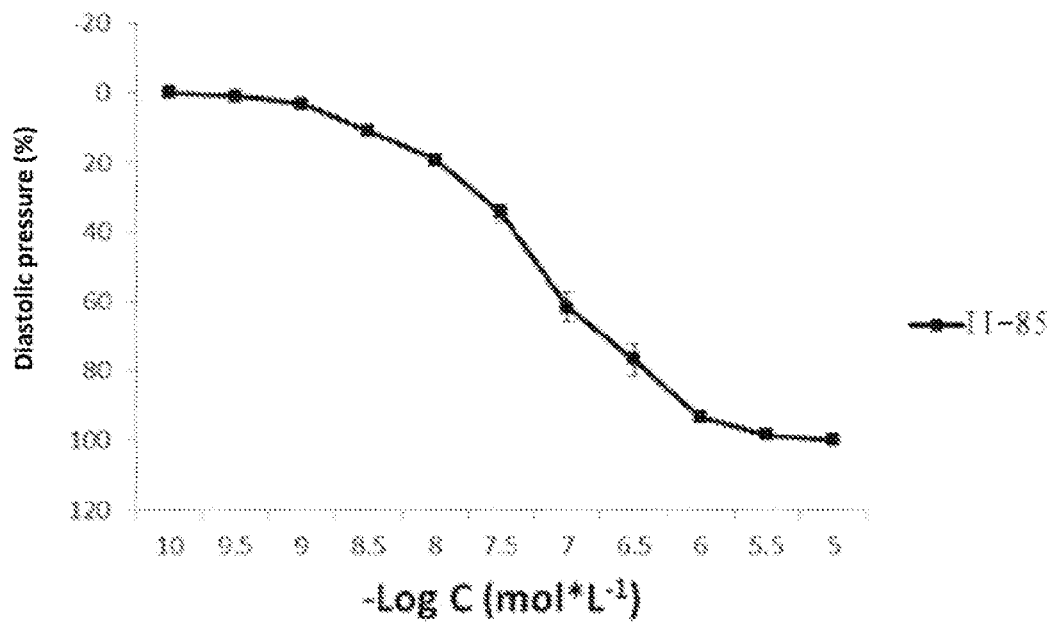
FIG. 17 illustrates the accumulated concentration effect curve of vasodilative effects of compound II-85 ($10^{-10}$-$10^{-2}$ mol·L$^{-1}$) versus vasoconstrictive effects of adrenaline ($10^{-5}$ mol·L$^{-1}$) on excised blood vessels from rabbits.

From FIG. 17, compound II-85 had relaxing effects on vascular samples constricted by AD in certain dose dependent manner. The $-\log EC_{50}$ value was 7.30±0.05 for compound II-85 to relax AD constricted rabbit aorta.

Relaxing effects of compound II-1 to II-60, II-84 to II-123 and II-124 to II-157 on vascular smooth muscle constricted by AD were shown in table 1:

TABLE 1

| Compound | $-\log EC_{50}$ |
|---|---|
| II-1 | 5.03 ± 0.04 |
| II-2 | 5.73 ± 0.03 |
| II-3 | 6.01 ± 0.05 |
| II-4 | 4.96 ± 0.03 |
| II-5 | 4.78 ± 0.04 |
| II-6 | 4.63 ± 0.06 |
| II-7 | 4.29 ± 0.05 |
| II-8 | 4.71 ± 0.04 |
| II-9 | 4.37 ± 0.03 |
| II-10 | 4.26 ± 0.05 |
| II-11 | 4.05 ± 0.04 |
| II-12 | 4.35 ± 0.06 |
| II-13 | 4.41 ± 0.05 |
| II-14 | 4.22 ± 0.04 |
| II-15 | 4.47 ± 0.04 |
| II-16 | 4.29 ± 0.03 |
| II-17 | 4.53 ± 0.03 |
| II-18 | 4.86 ± 0.06 |
| II-19 | 4.18 ± 0.04 |
| II-20 | 4.23 ± 0.05 |
| II-21 | 4.05 ± 0.03 |
| II-22 | 4.55 ± 0.04 |
| II-23 | 4.72 ± 0.03 |
| II-24 | 4.52 ± 0.04 |
| II-25 | 4.79 ± 0.05 |
| II-26 | 4.19 ± 0.04 |
| II-27 | 4.31 ± 0.04 |
| II-28 | 3.99 ± 0.03 |
| II-29 | 6.01 ± 0.02 |
| II-30 | 5.52 ± 0.03 |
| II-31 | 6.19 ± 0.03 |
| II-32 | 5.41 ± 0.03 |
| II-33 | 4.39 ± 0.04 |
| II-34 | 8.07 ± 0.06 |
| II-35 | 4.89 ± 0.05 |
| II-36 | 5.31 ± 0.04 |
| II-37 | 5.56 ± 0.03 |
| II-38 | 5.72 ± 0.05 |
| II-39 | 5.47 ± 0.04 |
| II-40 | 5.35 ± 0.06 |
| II-41 | 4.51 ± 0.05 |
| II-42 | 4.39 ± 0.04 |
| II-43 | 4.45 ± 0.04 |
| II-44 | 4.15 ± 0.03 |
| II-45 | 4.33 ± 0.03 |
| II-46 | 4.26 ± 0.06 |
| II-47 | 3.88 ± 0.04 |
| II-48 | 3.83 ± 0.05 |
| II-49 | 4.05 ± 0.03 |
| II-50 | 4.35 ± 0.04 |
| II-51 | 4.52 ± 0.03 |
| II-52 | 4.88 ± 0.04 |
| II-53 | 4.28 ± 0.05 |
| II-54 | 5.21 ± 0.04 |
| II-55 | 4.01 ± 0.03 |
| II-56 | 4.26 ± 0.05 |
| II-57 | 4.21 ± 0.03 |
| II-58 | 4.17 ± 0.04 |
| II-59 | 4.53 ± 0.05 |
| II-60 | 4.05 ± 0.04 |
| II-84 | 6.23 ± 0.04 |
| II-85 | 7.30 ± 0.05 |
| II-86 | 5.45 ± 0.04 |
| II-87 | 5.34 ± 0.03 |
| II-88 | 5.61 ± 0.05 |
| II-89 | 5.42 ± 0.04 |
| II-90 | 5.38 ± 0.03 |
| II-91 | 5.23 ± 0.05 |
| II-92 | 5.56 ± 0.04 |
| II-93 | 6.11 ± 0.07 |
| II-94 | 5.92 ± 0.05 |
| II-95 | 5.96 ± 0.04 |
| II-96 | 5.53 ± 0.07 |
| II-97 | 5.23 ± 0.06 |
| II-98 | 4.03 ± 0.05 |
| II-99 | 4.26 ± 0.04 |
| II-100 | 4.01 ± 0.03 |
| II-101 | 4.13 ± 0.05 |
| II-102 | 4.26 ± 0.06 |
| II-103 | 5.21 ± 0.05 |
| II-104 | 5.02 ± 0.04 |
| II-105 | 5.18 ± 0.03 |
| II-106 | 5.21 ± 0.05 |
| II-107 | 5.03 ± 0.02 |
| II-108 | 5.16 ± 0.03 |
| II-109 | 6.21 ± 0.04 |
| II-110 | 6.36 ± 0.03 |
| II-111 | 4.89 ± 0.02 |
| II-112 | 4.76 ± 0.03 |
| II-113 | 5.31 ± 0.04 |
| II-114 | 4.86 ± 0.03 |
| II-115 | 4.79 ± 0.02 |
| II-116 | 5.56 ± 0.05 |
| II-117 | 5.31 ± 0.06 |
| II-118 | 4.43 ± 0.05 |
| II-119 | 4.86 ± 0.04 |
| II-120 | 4.72 ± 0.03 |
| II-121 | 4.39 ± 0.05 |
| II-122 | 4.22 ± 0.06 |
| II-123 | 4.83 ± 0.05 |
| II-124 | 5.03 ± 0.02 |
| II-125 | 5.16 ± 0.03 |
| II-126 | 6.21 ± 0.04 |
| II-127 | 6.36 ± 0.03 |
| II-128 | 4.89 ± 0.02 |
| II-129 | 4.76 ± 0.03 |
| II-130 | 5.31 ± 0.04 |
| II-131 | 4.86 ± 0.03 |
| II-132 | 4.79 ± 0.02 |
| II-133 | 5.56 ± 0.05 |
| II-134 | 5.31 ± 0.06 |
| II-135 | 5.45 ± 0.04 |
| II-136 | 5.34 ± 0.03 |
| II-137 | 5.61 ± 0.05 |
| II-138 | 5.42 ± 0.04 |
| II-139 | 5.38 ± 0.03 |
| II-140 | 5.23 ± 0.05 |
| II-141 | 5.56 ± 0.04 |
| II-142 | 6.11 ± 0.07 |
| II-143 | 5.92 ± 0.05 |
| II-144 | 5.96 ± 0.04 |
| II-145 | 5.53 ± 0.07 |
| II-146 | 5.23 ± 0.06 |
| II-147 | 4.03 ± 0.05 |
| II-148 | 4.26 ± 0.04 |
| II-149 | 4.01 ± 0.03 |
| II-150 | 4.13 ± 0.05 |
| II-151 | 4.26 ± 0.06 |
| II-152 | 4.43 ± 0.05 |
| II-153 | 4.86 ± 0.04 |
| II-154 | 4.72 ± 0.03 |
| II-155 | 4.39 ± 0.05 |
| II-156 | 4.22 ± 0.06 |
| II-157 | 4.83 ± 0.05 |

6.2 Relaxing Effects of Compound II-84 to II-157 on Vascular Smooth Muscle Constricted by Noradrenaline (NA) In Vitro After sample tension became stable, a piece of waveform was recorded. Adrenaline hydrochloride (AD) ($10^{-5}$ mol/L) was added into a bath tube to induce constriction, when maximal constriction was achieved, the sample was completely flushed, K-H solution was changed for every 20 min. Contents in the tube was balanced for 60 min, when baseline recovered to be stable, noradrenaline bitartrate (NA) ($10^{-5}$ mol/L) was added to induce constriction. When the later maximal constriction response was basically consistent with the former one, the prepared compound solutions were subsequently added, including compound II-84 to II-123 solutions ($1\times10^{-10}$-$1\times10^{-2}$ mol/L), compound II-124 to II-157 solutions ($1\times10^{-10}$-$1\times10^{-3}$ mol/L), to record the waveforms. Relaxing percentage of the compound was used as Y axis, maximal relaxation response was 100%, negative logarithm of different concentration was used as X axis, to draw dose effect curve (expressed in mean±SEM (—•—), n=5).

Figure 18:
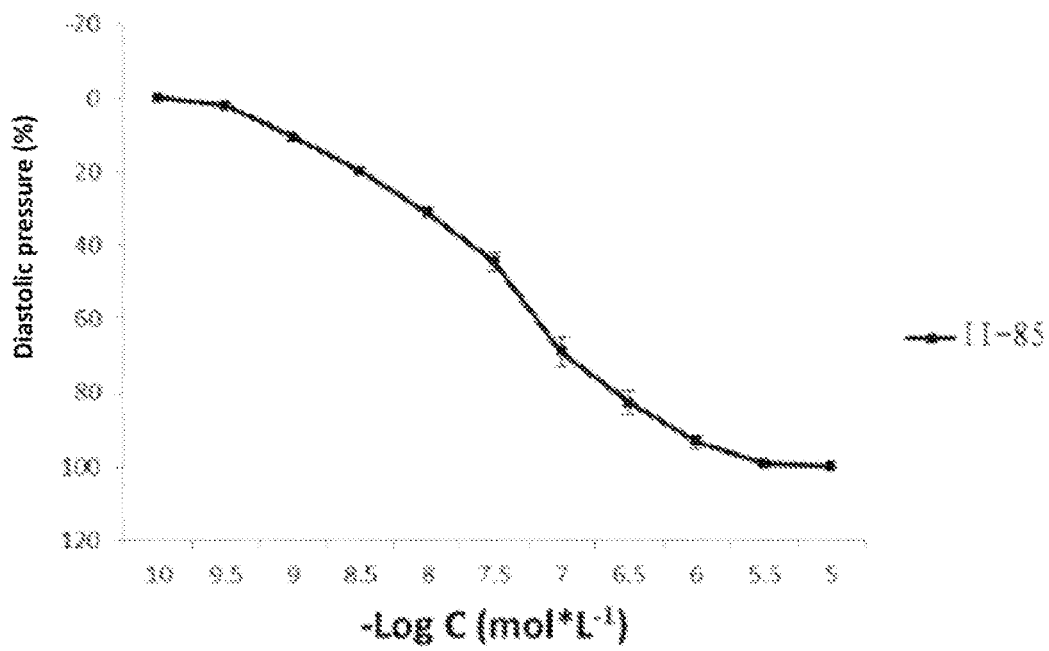
FIG. 18 illustrates the accumulated concentration effect curve of vasodilative effects of compound II-85 ($10^{-10}$-$10^{-2}$ mol·L$^{-1}$) versus vasoconstrictive effects of noradrenaline ($10^{-5}$ mol·L$^{-1}$) on excised blood vessels from rabbits.

From FIG. 18, compound II-85 had relaxing effects on vascular samples constricted by NA in certain dose dependent manner. The $-\log EC_{50}$ value was 7.51±0.05 for compound II-85 to relax NA constricted rabbit aorta.

Relaxing effects of compound II-84 to II-157 on vascular smooth muscle constricted by NA in vitro were shown in table 2:

TABLE 2

| Compound | $-\log EC_{50}$ |
|---|---|
| II-84 | 6.17 ± 0.03 |
| II-85 | 7.51 ± 0.05 |
| II-86 | 5.26 ± 0.04 |
| II-87 | 5.04 ± 0.03 |
| II-88 | 5.73 ± 0.05 |
| II-89 | 5.22 ± 0.04 |
| II-90 | 5.35 ± 0.03 |
| II-91 | 5.31 ± 0.05 |
| II-92 | 5.73 ± 0.04 |
| II-93 | 6.07 ± 0.04 |
| II-94 | 5.81 ± 0.03 |
| II-95 | 5.73 ± 0.04 |
| II-96 | 5.31 ± 0.06 |
| II-97 | 5.09 ± 0.04 |
| II-98 | 4.31 ± 0.05 |
| II-99 | 4.04 ± 0.07 |
| II-100 | 4.19 ± 0.03 |
| II-101 | 4.43 ± 0.04 |
| II-102 | 4.06 ± 0.06 |
| II-103 | 5.11 ± 0.05 |
| II-104 | 5.02 ± 0.04 |
| II-105 | 5.11 ± 0.03 |
| II-106 | 5.10 ± 0.05 |
| II-107 | 5.11 ± 0.02 |
| II-108 | 5.27 ± 0.03 |
| II-109 | 6.32 ± 0.04 |
| II-110 | 6.45 ± 0.03 |
| II-111 | 4.67 ± 0.02 |
| II-112 | 4.55 ± 0.03 |
| II-113 | 5.21 ± 0.04 |
| II-114 | 4.77 ± 0.03 |
| II-115 | 4.53 ± 0.02 |
| II-116 | 5.36 ± 0.05 |
| II-117 | 5.15 ± 0.06 |
| II-118 | 4.23 ± 0.03 |
| II-119 | 4.66 ± 0.02 |
| II-120 | 4.52 ± 0.04 |
| II-121 | 4.44 ± 0.05 |
| II-122 | 4.34 ± 0.04 |
| II-123 | 4.53 ± 0.05 |
| II-124 | 5.11 ± 0.02 |
| II-125 | 5.27 ± 0.03 |
| II-126 | 6.32 ± 0.04 |
| II-127 | 6.45 ± 0.03 |
| II-128 | 4.67 ± 0.02 |
| II-129 | 4.55 ± 0.03 |
| II-130 | 5.21 ± 0.04 |
| II-131 | 4.77 ± 0.03 |
| II-132 | 4.53 ± 0.02 |
| II-133 | 5.36 ± 0.05 |
| II-134 | 5.15 ± 0.06 |
| II-135 | 5.26 ± 0.04 |
| II-136 | 5.04 ± 0.03 |
| II-137 | 5.73 ± 0.05 |
| II-138 | 5.22 ± 0.04 |
| II-139 | 5.35 ± 0.03 |
| II-140 | 5.31 ± 0.05 |
| II-141 | 5.73 ± 0.04 |
| II-142 | 6.07 ± 0.04 |
| II-143 | 5.81 ± 0.03 |
| II-144 | 5.73 ± 0.04 |
| II-145 | 5.31 ± 0.06 |
| II-146 | 5.09 ± 0.04 |
| II-147 | 4.31 ± 0.05 |

TABLE 2-continued

| Compound | $-\log EC_{50}$ |
|---|---|
| II-148 | 4.04 ± 0.07 |
| II-149 | 4.19 ± 0.03 |
| II-150 | 4.43 ± 0.04 |
| II-151 | 4.06 ± 0.06 |
| II-152 | 4.23 ± 0.03 |
| II-153 | 4.66 ± 0.02 |
| II-154 | 4.52 ± 0.04 |
| II-155 | 4.44 ± 0.05 |
| II-156 | 4.34 ± 0.04 |
| II-157 | 4.53 ± 0.05 |

6.3 Relaxing Effects of Compound II-1 to II-60 and II-84 to II-157 on Vascular Smooth Muscle Constricted by High Kalium Concentration In Vitro After sample tension became stable, a piece of waveform was recorded. Adrenaline hydrochloride (AD) ($10^{-5}$ mol/L) was added into a bath tube to induce constriction, when maximal constriction was achieved, the sample was completely flushed, K-H solution was changed for every 20 min. Contents in the tube was balanced for 60 min, when baseline recovered to be stable, K-H solution in the bath tube was replaced with high kalium concentration solution to induce constriction. When the later maximal constriction response was basically consistent with the former one, the prepared compound solutions were subsequently added, including compound II-1 to II-60 solutions ($1\times10^{-8}$-$1\times10^{-3}$ mol/L), compound II-84 to II-123 solutions ($1\times10^{-10}$-$1\times10^{-2}$ mol/L) and compound II-124 to II-157 solutions ($1\times10^{-10}$-$1\times10^{-3}$ mol/L), to record the waveforms. Relaxing percentage of the compound was used as Y axis, maximal relaxation response was 100%, negative logarithm of different concentration was used as X axis, to draw dose effect curve (expressed in mean±SEM (—•—), n=5). Compounds II-2 and II-3 had the most obvious relaxing effects (FIG. 2 and FIG. 9).

From FIG. 2 and FIG. 9, compounds II-2 and II-3 had obvious relaxing effects on samples constricted by high kalium concentration solution in certain dose dependent manner. The $-\log EC_{50}$ value was 5.34±0.02 for compound II-2 to relax high kalium concentration constricted rabbit aorta, and 5.49±0.05 for compound II-3. Of these compounds, compound II-31 also had relatively obvious relaxing effects, negative logarithms of different concentrations were used as X axis to draw dose effective curves, which were shown in FIG. 11. II-29 also had obvious relaxing effects, and its dose effect curve was shown in FIG. 16. From FIG. 11, compound II-31 had relaxing effects on samples constricted by high kalium concentration in certain dose dependent manner. The $-\log EC_{50}$ value was 5.55±0.03 for compound II-31 to relax high kalium concentration constricted rabbit aorta. Similarly, the relaxing effects of compound II-29 against high kalium concentration was also in a dose dependent manner. The $-\log EC_{50}$ value was 5.64±0.01 for compound II-29 to relax high kalium concentration constricted rabbit aorta.

Figure 19:
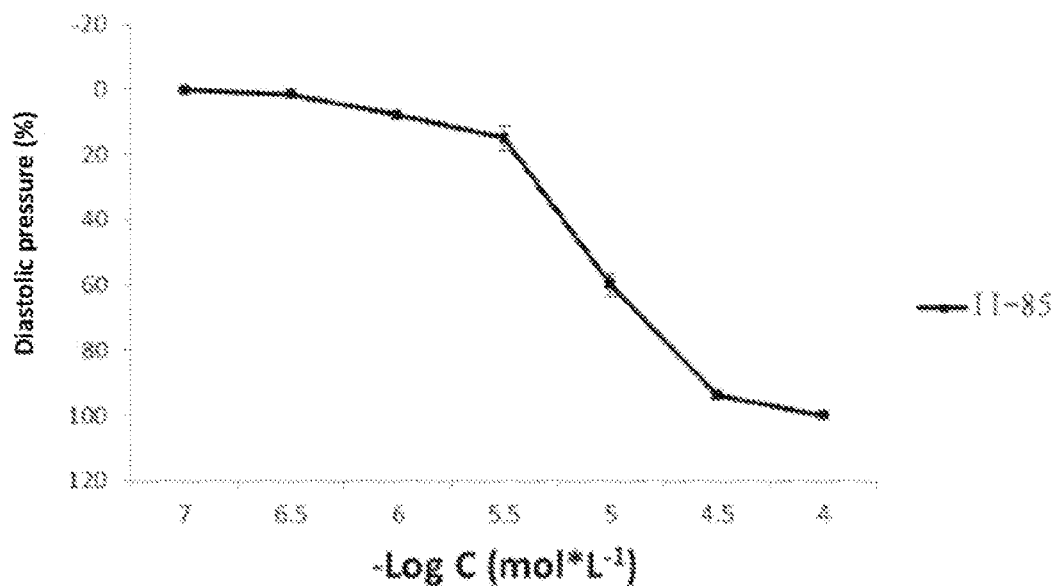
FIG. 19 illustrates the accumulated concentration effect curve of vasodilative effects of compound II-85 ($10^{-10}$-$10^{-2}$ mol·L$^{-1}$) versus vasoconstrictive effects of high potassium concentration (60 mmol·L$^{-1}$) on excised blood vessels from rabbits.

From FIG. 19, compound II-85 had relaxing effects on vascular samples constricted by high kalium concentration in certain dose dependent manner. The $-\log EC_{50}$ value was 6.21±0.03 for compound II-85 to relax high kalium concentration constricted rabbit aorta.

Relaxing effects of compound II-1 to II-60 and II-84 to II-157 on vascular smooth muscle constricted by high kalium concentration in vitro were shown in table 3:

TABLE 3

| Compound | $-\log EC_{50}$ |
|---|---|
| II-1 | 5.05 ± 0.03 |
| II-2 | 5.34 ± 0.02 |
| II-3 | 5.49 ± 0.05 |
| II-4 | 4.79 ± 0.05 |
| II-5 | 4.53 ± 0.03 |
| II-6 | 4.41 ± 0.04 |
| II-7 | 3.79 ± 0.03 |
| II-8 | 4.41 ± 0.05 |
| II-9 | 4.28 ± 0.03 |
| II-10 | 3.96 ± 0.05 |
| II-11 | 3.85 ± 0.04 |
| II-12 | 4.15 ± 0.06 |
| II-13 | 4.52 ± 0.05 |
| II-14 | 4.05 ± 0.04 |
| II-15 | 4.52 ± 0.05 |
| II-16 | 4.19 ± 0.03 |
| II-17 | 4.31 ± 0.04 |
| II-18 | 4.74 ± 0.06 |
| II-19 | 4.06 ± 0.03 |
| II-20 | 3.93 ± 0.02 |
| II-21 | 3.75 ± 0.03 |
| II-22 | 4.64 ± 0.04 |
| II-23 | 4.42 ± 0.05 |
| II-24 | 4.52 ± 0.04 |
| II-25 | 4.53 ± 0.03 |
| II-26 | 3.99 ± 0.05 |
| II-27 | 4.06 ± 0.04 |
| II-28 | 3.85 ± 0.04 |
| II-29 | 5.64 ± 0.01 |
| II-30 | 5.13 ± 0.03 |
| II-31 | 5.55 ± 0.03 |
| II-32 | 4.61 ± 0.03 |
| II-33 | 3.94 ± 0.04 |
| II-34 | 4.77 ± 0.02 |
| II-35 | 4.49 ± 0.05 |
| II-36 | 5.31 ± 0.04 |
| II-37 | 5.43 ± 0.03 |
| II-38 | 5.33 ± 0.04 |
| II-39 | 5.22 ± 0.04 |
| II-40 | 5.29 ± 0.04 |
| II-41 | 4.61 ± 0.05 |
| II-42 | 3.93 ± 0.04 |
| II-43 | 3.85 ± 0.04 |
| II-44 | 3.73 ± 0.03 |
| II-45 | 4.09 ± 0.03 |
| II-46 | 3.92 ± 0.02 |
| II-47 | 3.54 ± 0.03 |
| II-48 | 3.43 ± 0.04 |
| II-49 | 3.85 ± 0.03 |
| II-50 | 3.79 ± 0.04 |
| II-51 | 4.46 ± 0.03 |
| II-52 | 4.58 ± 0.04 |
| II-53 | 3.88 ± 0.02 |
| II-54 | 4.91 ± 0.04 |
| II-55 | 3.71 ± 0.03 |
| II-56 | 3.51 ± 0.02 |
| II-57 | 3.58 ± 0.02 |
| II-58 | 3.75 ± 0.04 |
| II-59 | 4.21 ± 0.03 |
| II-60 | 3.81 ± 0.02 |
| II-84 | 4.27 ± 0.04 |
| II-85 | 5.21 ± 0.03 |
| II-86 | 4.09 ± 0.04 |
| II-87 | 4.12 ± 0.03 |
| II-88 | 4.72 ± 0.05 |
| II-89 | 4.12 ± 0.04 |
| II-90 | 4.28 ± 0.03 |
| II-91 | 4.02 ± 0.05 |
| II-92 | 4.32 ± 0.04 |
| II-93 | 4.11 ± 0.03 |
| II-94 | 3.92 ± 0.02 |
| II-95 | 3.96 ± 0.03 |
| II-96 | 3.53 ± 0.02 |
| II-97 | 3.23 ± 0.04 |
| II-98 | 3.53 ± 0.03 |
| II-99 | 3.26 ± 0.04 |
| II-100 | 3.31 ± 0.03 |
| II-101 | 3.63 ± 0.04 |
| II-102 | 3.46 ± 0.03 |
| II-103 | 3.21 ± 0.05 |
| II-104 | 3.42 ± 0.04 |
| II-105 | 3.38 ± 0.03 |
| II-106 | 3.23 ± 0.05 |
| II-107 | 3.69 ± 0.02 |
| II-108 | 3.82 ± 0.03 |
| II-109 | 5.01 ± 0.04 |
| II-110 | 5.12 ± 0.03 |
| II-111 | 3.44 ± 0.02 |
| II-112 | 3.38 ± 0.03 |
| II-113 | 4.03 ± 0.04 |
| II-114 | 3.56 ± 0.03 |
| II-115 | 3.23 ± 0.02 |
| II-116 | 4.22 ± 0.05 |
| II-117 | 4.17 ± 0.06 |
| II-118 | 3.53 ± 0.03 |
| II-119 | 3.26 ± 0.04 |
| II-120 | 3.32 ± 0.02 |
| II-121 | 3.14 ± 0.05 |
| II-122 | 3.04 ± 0.03 |
| II-123 | 3.13 ± 0.04 |
| II-124 | 4.69 ± 0.02 |
| II-125 | 4.82 ± 0.03 |
| II-126 | 6.01 ± 0.04 |
| II-127 | 6.12 ± 0.03 |
| II-128 | 4.44 ± 0.02 |
| II-129 | 4.38 ± 0.03 |
| II-130 | 5.03 ± 0.04 |
| II-131 | 4.56 ± 0.03 |
| II-132 | 4.23 ± 0.02 |
| II-133 | 5.22 ± 0.05 |
| II-134 | 5.17 ± 0.06 |
| II-135 | 5.09 ± 0.04 |
| II-136 | 5.12 ± 0.03 |
| II-137 | 5.72 ± 0.05 |
| II-138 | 5.12 ± 0.04 |
| II-139 | 5.28 ± 0.03 |
| II-140 | 5.02 ± 0.05 |
| II-141 | 5.32 ± 0.04 |
| II-142 | 5.11 ± 0.03 |
| II-143 | 3.92 ± 0.02 |
| II-144 | 3.96 ± 0.03 |
| II-145 | 3.53 ± 0.02 |
| II-146 | 4.23 ± 0.04 |
| II-147 | 3.53 ± 0.03 |
| II-148 | 4.26 ± 0.04 |
| II-149 | 3.31 ± 0.03 |
| II-150 | 3.63 ± 0.04 |
| II-151 | 3.46 ± 0.03 |
| II-152 | 4.53 ± 0.03 |
| II-153 | 4.26 ± 0.04 |
| II-154 | 4.32 ± 0.02 |
| II-155 | 4.14 ± 0.05 |
| II-156 | 4.04 ± 0.03 |
| II-157 | 4.13 ± 0.04 |

Example 135

Study on Mechanism of Relaxing Effects of Compound II-2 and II-85 on Vascular Smooth Muscle In Vitro 1. Experimental Animals:
Rabbits, male or female, 2.0-3.0 kg, were provided by Experimental Animal Center, China Medical university.
2. Drugs and Reagents
Methods described in Example 2 and 72 were adopted to prepare compound II-2 and II-85.
Sodium chloride (NaCl): bought from Tianjin Damao Chemical Reagent Factory, batch number 20120413.
Kalium chloride (NaCl): bought from Tianjin Damao Chemical Reagent Factory, batch number 20111123.

Anhydrous magnesium sulfate (MgSO$_4$): bought from Tianjin Damao Chemical Reagent Factory, batch number 20101029.

Anhydrous calcium chloride (CaCl$_2$): bought from Tianjin Damao Chemical Reagent Factory, batch number 20110314.

Sodium bicarbonate (NaHCO$_3$): bought from Tianjin Damao Chemical Reagent Factory, batch number 20120507.

Glucose: bought from Tianjin Damao Chemical Reagent Factory, batch number 20120512.

Kalium dihydrogen phosphate (KH$_2$PO$_4$): bought from Tianjin Damao Chemical Reagent Factory, batch number 20110928.

Sodium chloride injection (NaCl): bought from Shenyang Zhiying Pharmaceutical Factory, batch number: 12021001.

Epinephrine hydrochloride injection: strength: 1 mg/1 ml, bought from Grandpharma (China) Co., Ltd., batch number: 120105.

Norepinephrine bitartrate injection: strength: 2 mg/1 ml, bought from Grandpharma (China) Co., Ltd., batch number: 120304.

Doxazosin mesylate: bought from Suizhou hake Pharmaceutical and Chemical Industry Co., Ltd., batch number: 20110305.

Amlodipine besylate tablets: bought from Pfizer, strength: 5 mg/tablet, batch number: 1205018. Epinephrine hydrochloride injection: strength: 1 mg/1 ml, bought from Grandpharma (China) Co., Ltd., batch number: 120105.

(R)-phenylephrine hydrochloride, bought from Tokyo Chemical Industry (Shanghai), batch number: GJ01-TESP.

Serotonin creatinine sulfate monohydrate (5-HT), bought from Tokyo Chemical Industry, batch number: AZ01-TBKD.

Heparin sodium injection: bought from China Wanbang, strength: 2 ml/12500 unit, batch number: 101115.

Urethane: Shanghai Chemical Reagent Company, China National Pharmaceutical Group, batch number: C30191228.

EDTA: bought from Tianjin Damao Chemical Reagent Factory, batch number 20050809.

3. Experimental Instruments

HSS-1(B) thermostat bath: Chengdu Instrument Factory.

RM6240B multi-channel physiological signal collection & processing system: Chengdu Instrument Factory.

JZJ01 muscular strength transducer: Chengdu Instrument Factory.

YPJ01 pressure transducer: Chengdu Instrument Factory.

TG-328A photoelectric analytical balance: Shanghai Balance Factory.

T-500 electronic balance: Chuangshu Shuangjie Test Instrument Factory.

Micropipette: Shanghai Rongtai Biochemical Engineering Co., Ltd.

electrical heated thermostatic water bath: Tianjin Taisite Instrument Co., Ltd.

4. Preparation of Nutrient Solution

Krebs-Henseleit (K-H) normal saline: NaCl 6.92 (concentration unit), KCl 0.35, MgSO$_4$ 0.29, KH$_2$PO$_4$ 0.16, CaCl$_2$ 0.28, NaHCO$_3$ 2.1, Glucose 2.0 (g/L), pH 7.2.

High kalium solution: removing equal mole of NaCl from K-H solution, adding KCl to prepare modified K-H solution containing K$^+$60 mmol/L.

K-H free solution: removing CaCl$_2$ from K-H solution, adding equal mole of KCl and EDTA$^{-2}$Na$^+$0.1 mmol/L, other components not changed.

Calcium free high kalium solution: removing CaCl$_2$ from high kalium solution, adding equal mole of KCl and EDTA$^{-2}$Na$^+$0.1 mmol/L, other components not changed.

Preparation of compound II-2 and II-85 solutions: weigh appropriate amount of compound II-2 and II-85 samples, dilute to solutions of series concentrations with distilled water ($10^{-10}$-$10^{-4}$ mol/L) for later use.

5. Preparation of Excised Vascular Smooth Muscle Sample from Rabbits

Rabbits were hit to be dizzy, with thoracic cavity quickly cut open, descending aorta exposed, connective tissues and surrounding fatty tissues (for hydroxytryptamine receptor antagonism test, endothelia should be removed with smooth stainless steel rod) removed, the aorta was cut into 3-5 mm vascular rings which were penetrated together with a steel wire with one end fixed on ventilation hook, another end on pressure tonotransducer. The aorta rings were put into a bath tube with 20 ml of nutritional solution, and the tension changes were recorded by using the recorder. The temperature of bath tube was maintained at 37±0.5° C., and mixed gas (95% O$_2$+5% CO$_2$) was ventilated at a rate of I-2 bubbles/second. The initial load of the sample was 1.5 g, nutritional solution was changed for every 20 min. The sample was balanced for 2 hours, and the experiment would be started when baseline became stable.

6. Experimental Procedure and Results 6.1 Antagonism of Compound II-2 and II-85 on α-Receptor Agonist of Vascular Smooth Muscle of Rabbits 6.1.1 Effects of Compound II-2 on Dose Effective Curve of Accumulative Constriction by Noradrenaline After sample tension became stable, a piece of waveform was recorded, noradrenaline (NA) ($10^{-8}$-$10^{-4}$ mol/L) was added into the bath tube until maximal response, then waveform was recorded. Then K-H solution was used to flush the sample repeatedly, after balanced for 1 hour, compound II-2 ($3 \times 10^{-7}$ mol/L) was added. NA was also added by using the same method 20 min later. The maximal response was considered 100%, NA constriction percentage was used as Y axis, negative logarithms of different concentrations were used as X axis to draw dose effective curve. The curve was shown in FIG. 3 after compound II-2 ($3 \times 10^{-7}$ mol/L) was added.

NA dose effective curve was obviously moved to right in parallel, with maximal response nearly unchanged. Percentages at different concentrations were statistically analyzed by using t test, most P values <0.01, suggesting significant difference. The PA$_2$ value was 7.37±0.08 for compound II-2 to resist constriction of rabbit aorta by NA.

6.1.2 Effects of Positive Reference Drug Doxazosin on Dose Effective Curve of Accumulative Constriction by Noradrenaline After sample tension became stable, a piece of waveform was recorded, noradrenaline (NA) ($10^{-8}$-$10^{-4}$ mol/L) ($10^{-8}$-$3 \times 10^{-3}$ mol/L) was added into the bath tube until maximal response, then waveform was recorded. Then samples were flushed with K-H solution repeatedly, K-H solution was changed for every 20 min, and the samples were balanced for 60 min. After baseline recovered to be stable, doxazosin ($10^{-7}$ mol/L) was added, and noradrenaline (NA) ($10^{-8}$-$6 \times 10^{-5}$ mol/L) was added by using the same method 15 min later. The maximal response was considered 100%, NA constriction percentage was used as Y axis, negative logarithms of different concentrations were used as X axis to draw dose effective curve. The curve was shown in FIG. 4 after doxazosin ($10^{-7}$ mol/L) was added. Dose effective curve of NA was obviously moved to right in parallel, with maximal response nearly unchanged. Percentages at different concentrations were statistically analyzed, most P values <0.01, suggesting significant difference. The PA$_2$ value was 7.52±0.04 for positive drug doxazosin to resist constriction of rabbit aorta by NA.

Statistical t test showed that, for PA$_2$ values of compound II-2 and positive drug doxazosin against NA, P>0.05, suggesting no significant difference between them, which meant that compound II-2 and doxazosin had similar resisting effects against a receptor agonist.

6.1.3 Effects of Compound II-85 on Dose Effective Curve of Accumulative Constriction by Phenephrine After sample tension became stable, a piece of waveform was recorded, (R)-phenylephrine hydrochloride (PE) ($10^{-8}$-$6\times10^{-3}$ mol/L) was added into the bath tube until maximal response, then waveform was recorded. Then K-H solution was used to flush the sample repeatedly, after balanced for 1 hour, compound II-85 ($10^{-6}$ mol/L) was added. PE was also added by using the same method 20 min later. The maximal response was considered 100%, PE constriction percentage was used as Y axis, negative logarithms of different concentrations were used as X axis to draw dose effective curve (data were expressed in mean±SEM ( —•— ), n=5). The curve was shown in FIG. 20 after compound II-85 ($10^{-6}$ mol/L) was added.

Figure 20:
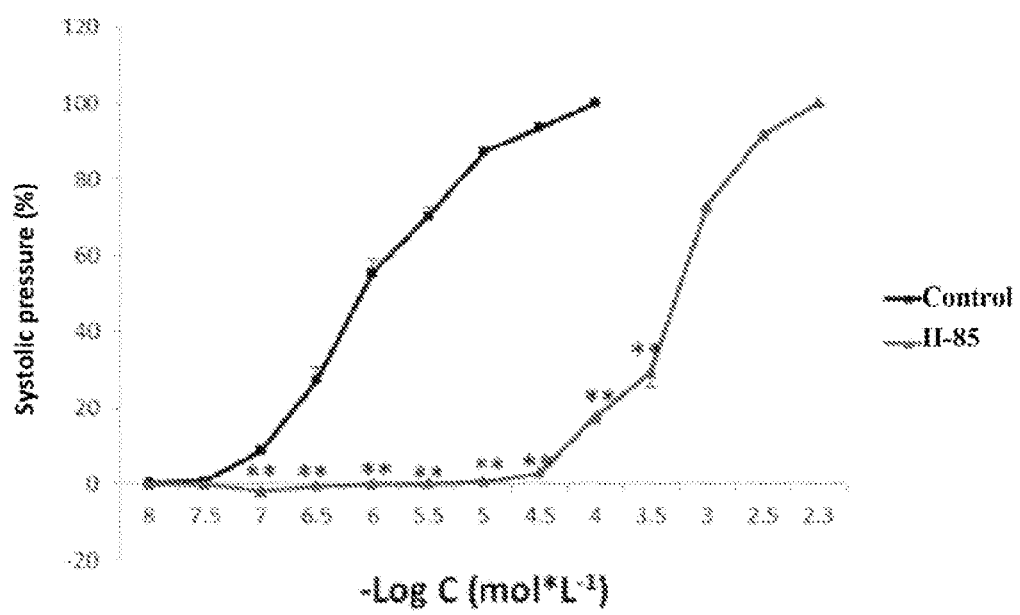
FIG. 20 illustrates the accumulated concentration effect curve of resistance of compound II-85 ($10^{-6}$ mol/L) to vasoconstrictive effects of phenephrine ($10^{-8}$-$6 \times 10^{-3}$ mol/L) on excised blood vessels from rabbits.

From FIG. 20, PE dose effective curve was obviously moved to right in parallel, with maximal response nearly unchanged. Percentages at different concentrations were statistically analyzed by using t test, most P values <0.01, suggesting significant difference. The $PA_2$ value was 8.62±0.11 for compound II-85 to resist constriction of rabbit aorta by PE.

6.1.4 Effects of Positive Reference Drug Doxazosine Mesylate on Dose Effective Curve of Accumulative Constriction by Phenylephrine After sample tension became stable, a piece of waveform was recorded, (R)-phenylephrine hydrochloride (PE) ($10^{-8}$-$3\times10^{-3}$ mol/L) was added into the bath tube until maximal response, then waveform was recorded. Then K-H solution was used to flush the sample repeatedly, after balanced for 1 hour, doxazosine mesylate ($10^{-6}$ mol/L) was added. PE was also added by using the same method 15 min later. The maximal response was considered 100%, PE constriction percentage was used as Y axis, negative logarithms of different concentrations were used as X axis to draw dose effective curve (data were expressed in mean±SEM ( —•— ), *P<0.05, P<0.01, n=7). The curve was shown in FIG. 21** after positive drug doxazosine mesylate ($10^{-7}$ mol/L) was added.

Figure 21:
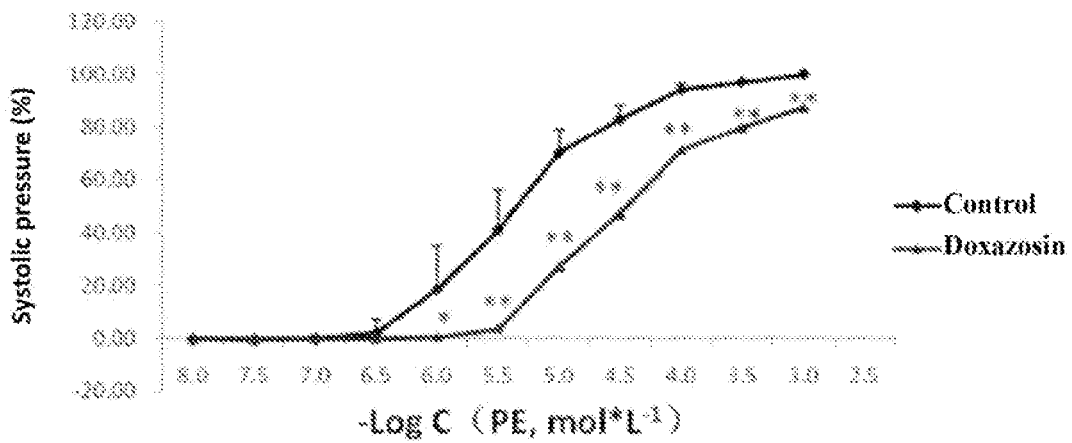
FIG. 21 illustrates the accumulated concentration effect curve of resistance of doxazosine mesylate ($10^{-6}$ mol/L) to vasoconstrictive effects of phenephrine ($10^{-8}$-$3 \times 10^{-3}$ mol/L) on blood vessels from rabbits.

From FIG. 21, PE dose effective curve was obviously moved to right in parallel, with maximal response nearly unchanged. Percentages at different concentrations were statistically analyzed by using t test, most P values <0.01, suggesting significant difference. The $PA_2$ value was 7.43±0.12 for positive drug doxazosin to resist constriction of rabbit aorta by PE.

Statistical t test showed that, for $PA_2$ values of compound II-85 and positive drug doxazosin against PE, P<0.01, suggesting very significant difference between them, which meant that compound II-85 had stronger resisting effects against a receptor agonist than doxazosin.

6.2 Antagonism of Compound II-2 and II-85 on Calcium Channel ($Ca^{2+}$) of Vascular Smooth Muscle of Rabbits 6.2.1 Effects of Compound II-2 on Dose Effect Curve of $CaCl_2$ on Accumulative Constriction of Rabbit Blood Vessels After sample tension became stable, calcium K-H solution was used to flush the sample for 3 times, and incubated with calcium free K-H solution for 40 min. Calcium free high kalium solution was added into the sample for depolarization for 20 min, then $CaCl_2$ ($10^{-6}$-$10^{-2}$ mol/L) was added into bath tube till maximal response was achieved, and then waveform was recorded. Then K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then compound II-2 ($3\times10^{-6}$ mol/L) was added into bath tube, which was incubated for 20 min, then $CaCl_2$ ($10^{-6}$-$10^{-2}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve. The curve was shown in FIG. 5 after compound II-2 ($3\times10^{-6}$ mol/L) was added. Dose effective curve of $CaCl_2$ was obviously moved to right in parallel, with maximal response nearly unchanged. Percentages at different concentrations were statistically analyzed, most P values <0.01, suggesting significant difference. The $PA_2$ value was 5.61±0.04 for compound II-2 to resist constriction of rabbit aorta by $CaCl_2$.

6.2.2 Effects of Positive Reference Drug Amlodipine on Dose Effective Curve of Accumulative Constriction by $CaCl_2$ After sample tension became stable, calcium K-H solution was used to flush the sample for 3 times, and incubated with calcium free K-H solution for 40 min. Calcium free high kalium solution was added into the sample for depolarization for 20 min, then $CaCl_2$ ($10^{-6}$-$10^{-2}$ mol/L) was added into bath tube till maximal response was achieved, and then waveform was recorded. Then K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then amlodipine ($10^{-7}$ mol/L) was added into bath tube, which was incubated for 15 min, then $CaCl_2$ ($10^{-6}$-$10^{-2}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve. The curve was shown in FIG. 6 after amlodipine ($3\times10^{-6}$ mol/L) was added. Dose effective curve of $CaCl_2$ was obviously moved to right in parallel, with maximal response nearly unchanged. Percentages at different concentrations were statistically analyzed, most P values <0.01, suggesting significant difference. The $PA_2$ value was 6.99±0.05 for amlodipine to resist constriction of rabbit aorta by $CaCl_2$.

6.2.3 Effects of Compound II-85 on Dose Effect Curve of $CaCl_2$ on Accumulative Constriction of Rabbit Blood Vessels After sample tension became stable, calcium K-H solution was used to flush the sample for 3 times, and incubated with calcium free K-H solution for 40 min. Calcium free high kalium solution was added into the sample for depolarization for 20 min, then $CaCl_2$ ($10^{-5}$-$10^{-2}$ mol/L) was added into bath tube till maximal response was achieved, and then waveform was recorded. Then K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then compound II-85 ($10^{-6}$ mol/L) was added into bath tube, which was incubated for 20 min, then $CaCl_2$ ($10^{-5}$-$10^{-2}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve (data were expressed in mean±SEM (—•—), *P<0.05, P<0.01, n=7). The results were shown in FIG. 22** after compound II-85 ($10^{-6}$ mol/L) was added.

Figure 22:
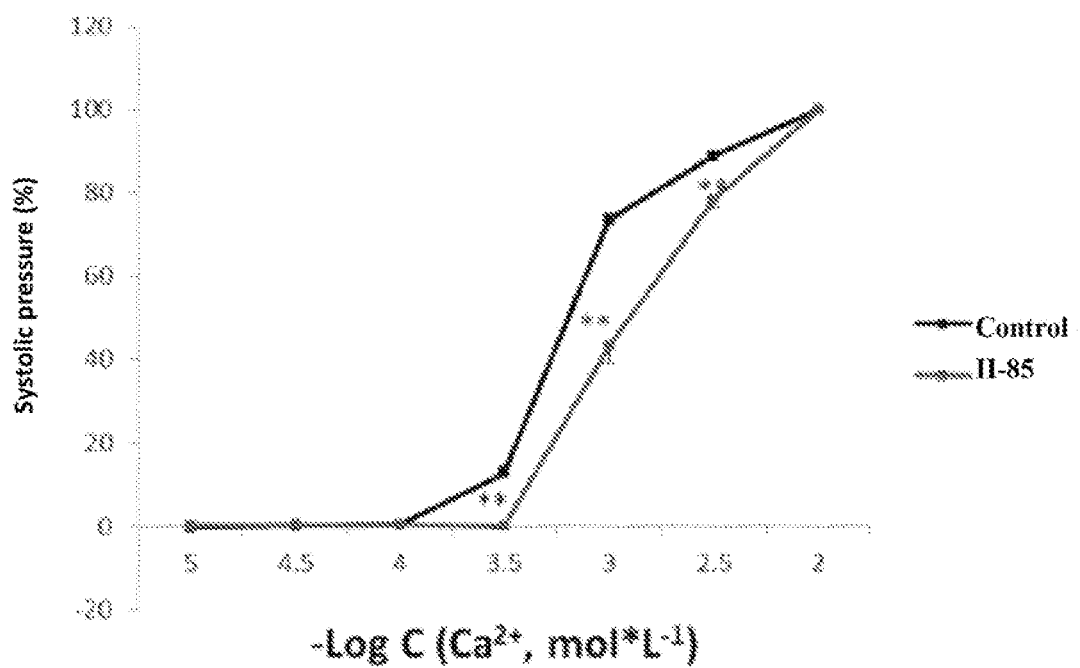
FIG. 22 illustrates the accumulated concentration effect curve of resistance of compound II-85 ($10^{-6}$ mol/L) to vasoconstrictive effects of CaCl$_2$ ($10^{-5}$-$10^{-2}$ mol/L) on excised blood vessels from rabbits.

From FIG. 22, dose effective curve of $CaCl_2$ was obviously moved to right in parallel, with maximal response nearly unchanged. Percentages at different concentrations were statistically analyzed, most P values <0.01, suggesting significant difference. The $PA_2$ value was 6.10±0.13 for compound II-85 to resist constriction of rabbit aorta by $CaCl_2$.

6.2.4 Effects of Amlodipine on Dose Effect Curve of $CaCl_2$ on Accumulative Constriction of Rabbit Blood Vessels After sample tension became stable, calcium K-H solution was used to flush the sample for 3 times, and incubated with calcium free K-H solution for 40 min. Calcium free high kalium solution was added into the sample for depolarization for 20 min, then $CaCl_2$ ($10^{-6}$-$10^{-2}$ mol/L) was added into bath tube till maximal response was achieved, and then waveform was recorded. Then K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then amlodipine ($10^{-7}$ mol/L) was added into bath tube, which was incubated for 15 min, then $CaCl_2$ ($10^{-6}$-$10^{-2}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve (data were expressed in mean±SEM (—•—), *P<0.05, P<0.01, n=5), as shown in FIG. 23**.

Figure 23:
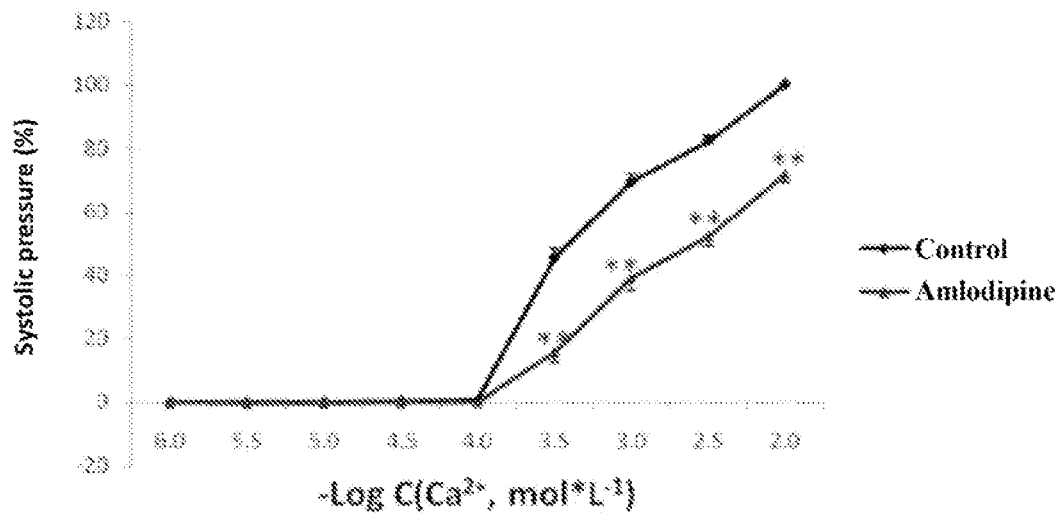
FIG. 23 illustrates the accumulated concentration effect curve of resistance of amlodipine ($10^{-7}$ mol/L) to vasoconstrictive effects of CaCl$_2$ ($10^{-6}$-$10^{-2}$ mol/L) on excised blood vessels from rabbits.

From FIG. 23, dose effective curve of $CaCl_2$ was obviously moved to right in parallel, with maximal response nearly unchanged. Percentages at different concentrations were statistically analyzed, most P values <0.01, suggesting significant difference. The $PA_2$ value was 6.99±0.05 for amlodipine to resist constriction of rabbit aorta by $CaCl_2$.

6.3 Antagonism of Compound II-2 on Hydroxytryptamine (5-HT) Receptor Agonist of Vascular Smooth Muscle of Rabbits After sample tension became stable, a piece of waveform was recorded, 5-HT ($10^{-7}$-$3\times10^{-4}$ mol/L) was added into the bath tube until maximal response, then waveform was recorded. Then K-H solution was used to flush the sample repeatedly, after balanced for 1.5 hour, compound II-2 ($3\times10^{-6}$ mol/L) was added. 5-HT was also added by using the same method 20 min later. The maximal response was considered 100%, 5-HT constriction percentage was used as Y axis, negative logarithms of different concentrations of 5-HT were used as X axis to draw dose effective curve. The curve was shown in FIG. 7 after compound II-2 ($3\times10^{-6}$ mol/L) was added. Dose effective curve of 5-HT was obviously moved to right in parallel, with maximal response nearly unchanged. Percentages at different concentrations were statistically analyzed, P value <0.01, suggesting significant difference. The $PA_2$ value was 5.71±0.08 for compound II-2 to resist constriction of rabbit aorta by 5-HT.

6.4 Antagonism of Compound II-85 on 5-HT Receptor Agonist of Vascular Smooth Muscle of Rabbits After sample tension became stable, a piece of waveform was recorded, 5-HT ($10^{-8}$-$10^{-3}$ mol/L) was added into the bath tube until maximal response, then waveform was recorded. Then K-H solution was used to flush the sample repeatedly, after balanced for 1.5 hour, compound II-85 ($10^{-7}$ mol/L) was added. 5-HT was also added by using the same method 20 min later. The maximal response was considered 100%, 5-HT constriction percentage was used as Y axis, negative logarithms of different concentrations of 5-HT were used as X axis to draw dose effective curve (data were expressed in mean±SEM (—•—), *P<0.05, P<0.01, n=7). The curve was shown in FIG. 8** after compound II-85 ($10^{-7}$ mol/L) was added.

Figure 24:
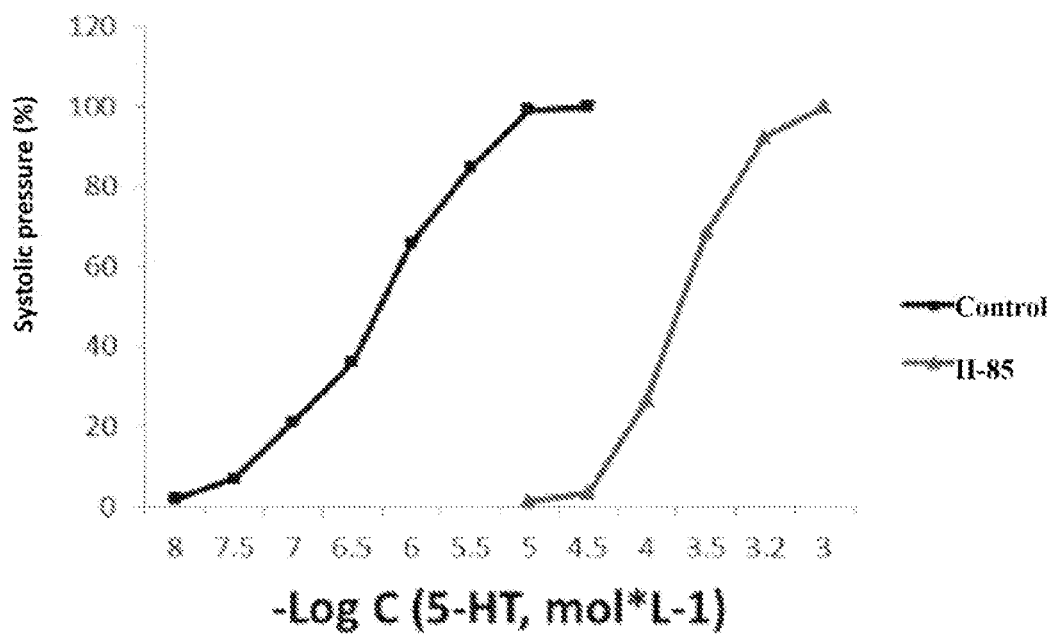
FIG. 24 illustrates the accumulated concentration effect curve of resistance of compound II-85 ($10^{-7}$ mol/L) to vasoconstrictive effects of 5-hydroxytryptamine ($10^{-8}$-$10^{-3}$ mol/L) on excised blood vessels from rabbits.

From FIG. 24, dose effective curve of 5-HT was obviously moved to right in parallel, with maximal response nearly unchanged. Percentages at different concentrations were statistically analyzed, most P values <0.01, suggesting significant difference. The $PA_2$ value was 9.06±0.07 for compound II-85 to resist constriction of rabbit aorta by 5-HT.

Example 136

Study on Mechanism of Relaxing Effects of Compound II-31 on Vascular Smooth Muscle In Vitro 1.1 Antagonism of Compound II-31 on α-Receptor Agonist of Vascular Smooth Muscle of Rabbits 1.1.1 Effects of Compound II-31 on Dose Effective Curve of Accumulative Constriction by Noradrenaline After sample tension became stable, a piece of waveform was recorded, noradrenaline (NA) ($3\times10^{-7}$-$6\times10^{-5}$ mol/L) was added into the bath tube until maximal response, then waveform was recorded. Then K-H solution was used to flush the sample repeatedly, after balanced for 1 hour, compound II-31 ($3\times10^{-6}$ mol/L) was added. NA ($3\times10^{-7}$-$3\times10^{-4}$ mol/L) was also added by using the same method 20 min later. The maximal response was considered 100%, NA constriction percentage was used as Y axis, negative logarithms of different concentrations were used as X axis to draw dose effective curve. The curve was shown in FIG. 10 after compound II-31 ($3\times10^{-6}$ mol/L) was added. Dose effective curve of NA was obviously moved to right in parallel, with maximal response nearly unchanged. Percentages at different concentrations were statistically analyzed by using t test, most P values <0.01, suggesting significant difference. The $PA_2$ value was 6.02±0.13 for compound II-31 to resist constriction of rabbit aorta by NA.

1.1.2 Effects of Positive Reference Drug Doxazosin on Dose Effective Curve of Accumulative Constriction by Noradrenaline Based on the last step, K-H solution was used to flush the sample repeatedly, after balanced for 1 hour, doxazosin ($10^{-7}$ mol/L) was added. NA was also added by using the same method 15 min later. The maximal response was considered 100%, NA constriction percentage was used as Y axis, negative logarithms of different concentrations of NA ($3\times10^{-7}$-$3\times10^{-4}$ mol/L) were used as X axis to draw dose effective curve. The curve was shown in FIG. 12 after doxazosin ($10^{-7}$ mol/L) was added. Dose effective curve of NA was obviously moved to right in parallel, with maximal response nearly unchanged. Percentages at different concentrations were statistically analyzed, most P values <0.01, suggesting significant difference. The $PA_2$ value was 7.76±0.24 for positive drug doxazosin to resist constriction of rabbit aorta by NA.

Statistical t test showed that, for $PA_2$ values of compound II-31 and positive drug doxazosin against NA, P<0.01, suggesting very significant difference between them, which meant that compound II-31 had weaker resisting effects against a receptor agonist than doxazosin.

1.2 Antagonism of Compound II-31 on Calcium Channel ($Ca^{2+}$) of Vascular Smooth Muscle of Rabbits 1.2.1 Effects of Compound II-31 on Dose Effect Curve of $CaCl_2$ on Accumulative Constriction of Rabbit Blood Vessels After sample tension became stable, calcium K-H solution was used to flush the sample for 3 times, and incubated with calcium free K-H solution for 40 min. Calcium free high kalium solution was added into the sample for depolarization for 20 min, then $CaCl_2$ ($10^{-5}$-$3\times10^{-2}$ mol/L) was added into bath tube till maximal response was achieved, and then waveform was recorded. Then K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then compound II-31 ($10^{-5}$ mol/L) was added into bath tube, which was incubated for 20 min, then $CaCl_2$ ($10^{-5}$-$3\times10^{-1}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve. The curve was shown in FIG. 13 after compound II-31 ($10^{-5}$ mol/L) was added. Dose effective curve of $CaCl_2$ was obviously moved to right in parallel, with maximal response nearly unchanged. Percentages at different concentrations were statistically analyzed, most P values <0.01, suggesting significant difference. The $PA_2$ value was 6.56±0.032 for compound II-31 to resist constriction of rabbit aorta by $CaCl_2$.

1.2.2 Effects of Positive Reference Drug Amlodipine on Dose Effective Curve of Accumulative Constriction by $CaCl_2$ Based on the last step, K-H solution was used to flush the sample repeatedly, the K-H solution was changed for every 20 min, and the sample was balanced for 60 min. After sample tension became stable, calcium K-H solution was used to flush the sample for 3 times, and incubated with calcium free K-H solution for 40 min. Calcium free high kalium solution was added into the sample for depolarization for 20 min, then amlodipine ($10^{-7}$ mol/L) was added into bath tube, which was incubated for 15 min, then $CaCl_2$ ($10^{-5}$-$3\times10^{-2}$ mol/L) was added by using the same method till maximal response was achieved, and then waveform was recorded. The maximal response was considered 100%, $CaCl_2$ constriction percentage was used as Y axis, negative logarithms of different concentrations were used as X axis to draw dose effective curve. The curve was shown in FIG. 13 after amlodipine ($10^{-5}$ mol/L) was added. Dose effective curve of $CaCl_2$ was obviously moved to right in parallel, with maximal response nearly unchanged. Percentages at different concentrations were statistically analyzed, most P values <0.01, suggesting significant difference. The $PA_2$ value was 7.51±0.288 for amlodipine to resist constriction of rabbit aorta by $CaCl_2$.

1.3 Antagonism of Compound II-31 on Hydroxytryptamine (5-HT) Receptor Agonist of Vascular Smooth Muscle of Rabbits After sample tension became stable, a piece of waveform was recorded, 5-HT ($10^{-8}$-$3\times10^{-4}$ mol/L) was added into the bath tube until maximal response, then waveform was recorded. Then K-H solution was used to flush the sample repeatedly, after balanced for 1.5 hour, compound II-31 ($3\times10^{-6}$ mol/L) was added. 5-HT was also added by using the same method 20 min later. The maximal response was considered 100%, 5-HT constriction percentage was used as Y axis, negative logarithms of different concentrations of 5-HT were used as X axis to draw dose effective curve. The curve was shown in FIG. 14 after compound II-31 ($3\times10^{-6}$ mol/L) was added. Dose effective curve of 5-HT was obviously moved to right in parallel, with maximal response nearly unchanged. Percentages at different concentrations were statistically analyzed, P value <0.01, suggesting significant difference. The $PA_2$ value was 6.726±0.089 for compound II-31 to resist constriction of rabbit aorta by 5-HT.

Example 137

Experiment on Acute Toxicity of Compound II-2

Kunming mice (Experimental Animal Center, China Medical University) were used, half male and half female, 18-22 g, brief probability unit method was used to test the acute toxicity of the compound. The compound $LD_{50}$ for gastric gavage was 361.88 mg/kg (95% confidential interval 302.96-420.80 mg/kg).

Experiment on Acute Toxicity of Compound II-85

Ten Kunming mice (Experimental Animal Center, China Medical University) were used, half male and half female, 18-22 g, brief probability unit method was used to test the acute toxicity of the compound. The compound $LD_{50}$ was 221.72 mg/kg (95% confidential interval 204.11-239.33 mg/kg) for gastric gavage, and 108.32 mg/kg (95% confidential interval 102.41-114.23 mg/kg) for intraabdominal injection.

Example 138

Marrow Micronucleus Test of Compound II-2 and II-85 on Mice

Ten Kunming mice (Experimental Animal Center, China Medical University), half male and half female, were used. Compound II-2 was administered via gastric gavage at 120 mg/kg/day, and II-85 was administered to 74 mg/kg/day. The drug was administered for 4 days continuously. Marrow micronucleus test was performed on day 5.

Mice in positive control group were administered cyclophosphane at 60 mg/kg/day. Mice in negative control group were administered normal saline at 0.1 ml/10 g/day. The drug was administered for 4 days continuously. Marrow micronucleus test was performed on day 5.

The mice were killed by snapping neck, and then femur and sternum were excised, with blood and muscles removed, epiphysis cut off. Then marrow from sternum was squeezed to clean glassslide with bovine serum by using a pair of hemostatic forceps, or marrow on femur was flushed directly with bovine serum onto clean glassslide. Then the substance on glassslide were mixed well and smeared. Then the prepared and dried marrow smears were put into staining tank with methanol, fixed for 15 min, picked out to dry in the open air. After marrow smears were dried, it would be stained in freshly prepared Giemsa solution (1 volume of Giemsa stock solution and 9 volumes of pH 6.8 phosphate buffer) for 10 min, staining solution was flushed away with little stream. Then the smear was dried in the open air and observed under a microscope.

Experimental Results Suggested that:

In 1000 polychromatic erythrocytes in compound II-2 group, micronuclei cells accounted for 2.0±0.333%; in 1000 polychromatic erythrocytes in blank group, micronuclei cells accounted for 1%; in 1000 polychromatic erythrocytes in cyclophosphane group, micronuclei cells accounted for 12%. The results suggested that, compound II-2 had negative marrow micronucleus test.

In 1000 polychromatic erythrocytes in compound II-85 group, micronuclei cells accounted for 2.5±0.373%; in 1000 polychromatic erythrocytes in blank group, micronuclei cells accounted for 1%; in 1000 polychromatic erythrocytes in cyclophosphane group, micronuclei cells accounted for 12%. The results suggested that, compound II-85 had negative marrow micronucleus test.

Example 139

Effects of Compound II-2 on Blood Pressure of SD Rats

Four SD rats were anesthetized with urethane (1.25 mg/kg), after vital signs became stable, blood pressure was measured by common carotid intubation. After blood pressure became stable, compound II-2 was administered at 4.0 mg/kg via gastric gavage, blood pressure changes with time were observed and recorded. The experimental results were shown in table 4, 5 and 6.

TABLE 4 effects of compound II-2 on diastolic blood pressure (DBP, mmHg) of rats anesthetized with urethane (n = 4)

| Groups | Drug dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 |
| Compound II-2 | 4.0 | 75.92 ± 26.19 | 62.21 ± 19.99** | 61.84 ± 24.65** | 58.04 ± 18.49** | 53.86 ± 20.22** | 69.10 ± 27.71** | 70.79 ± 27.81* | 71.08 ± 29.22* | 75.26 ± 33.42 |

Note:
*$P < 0.05$,
**$P < 0.01$

TABLE 5 effects of compound II-2 on systolic blood pressure (SBP, mmHg) of rats anesthetized with urethane (n = 4)

| Groups | Drug dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 |
| Compound II-2 | 4.0 | 122.66 ± 20.73 | 95.77 ± 16.29** | 99.88 ± 22.77** | 102.22 ± 16.29** | 98.71 ± 13.68** | 111.16 ± 20.37** | 111.82 ± 15.75** | 112.34 ± 15.26** | 115.12 ± 18.81* |

Note:
*$P < 0.05$,
**$P < 0.01$

TABLE 6 effects of compound II-2 on mean artery pressure (MAP, mmHg) of rats anesthetized with urethane (n = 4)

| Groups | Drug dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 |
| Compound II-2 | 4.0 | 91.50 ± 24.15 | 73.40 ± 17.80** | 74.52 ± 23.67** | 72.77 ± 17.52** | 68.81 ± 17.92** | 83.12 ± 25.17** | 84.47 ± 23.17** | 84.83 ± 24.50** | 88.54 ± 28.23* |

Note:
*$P < 0.05$,
**$P < 0.01$

Experimental results indicated that, compound II-2 had obvious hypotensive effects in SD rats anesthetized with urethane (1.25 mg/kg), and blood pressures recovered to those before drug dosing 3.5 hours later.

In summary, the above results indicated that, in animal experiments in vitro, compound II-2 had obvious relaxing effects of vascular smooth muscle. Compound II-2 had equal resisting effects to doxazosin on adrenaline a receptor, and the $PA_2$ value was $7.37\pm0.08$ for compound II to resist noradrenaline (NA), $7.52\pm0.04$ for doxazosin to resist NA, $5.61\pm0.04$ for compound II-2 to resist $CaCl_2$, and $5.71\pm0.08$ to resist 5-HT. In in vivo bulk testing on rats, compound II-2 showed good hypotensive effects, good oral absorption, mild toxicity, great therapeutic index, negative marrow micronucleus test, with protential value in development of multiple target vasodilative drugs, especially as new hypotensive drugs.

Example 140

Effects of Compound II-85 on Blood Pressure of SD Rats

Five SD rats (provided by Experimental Animal Center, China Medical University) were anesthetized with urethane (1.25 mg/kg), after vital signs became stable, blood pressure was measured by common carotid intubation. After blood pressure became stable, compound II-85 was administered at 1.5 mg/kg via gastric gavage, blood pressure changes with time were observed and recorded. The experimental results were shown in table 7, 8 and 9.

TABLE 7 effects of compound II-85 on diastolic blood pressure (DBP, mmHg) of rats anesthetized with urethane (n = 5)

| Groups | Drug dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 | 240 |
| Compound II-85 | 1.5 | 103.06 ± 12.20 | 75.36 ± 23.59* | 68.68 ± 21.71** | 75.49 ± 15.19** | 83.32 ± 23.28* | 83.71 ± 23.71* | 95.06 ± 20.03 | 86.22 ± 23.24 | 97.96 ± 21.62 | 102.84 ± 20.23 |

Note:
*$P < 0.05$,
**$P < 0.01$

TABLE 8 effects of compound II-85 on systolic blood pressure (SBP, mmHg) of rats anesthetized with urethane (n = 5)

| Groups | Dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 | 240 |
| Compound II-85 | 1.5 | 143.77 ± 12.69 | 125.22 ± 16.24** | 115.90 ± 18.14** | 122.75 ± 14.29* | 125.48 ± 22.07* | 122.89 ± 21.94 | 136.08 ± 12.15 | 127.90 ± 19.81 | 137.13 ± 19.48 | 142.19 ± 17.04 |

Note:
*$P < 0.05$,
**$P < 0.01$

TABLE 9 effects of compound II-85 on mean artery pressure (MAP, mmHg) of rats anesthetized with urethane (n = 5)

| Groups | Drug dose (mg/kg) | Post dosing (min) | | | | | | | | |
|---|---|---|---|---|---|---|---|---|---|---|
| | | 0 | 15 | 30 | 60 | 90 | 120 | 150 | 180 | 210 | 240 |
| Compound II-85 | 1.5 | 116.63 12.09 | 91.98 20.84* | 84.42 20.26** | 91.24 14.81** | 97.37 21.70* | 96.77 22.13* | 108.73 16.96 | 100.11 21.82 | 111.02 20.71 | 115.95 18.84 |

Note:
*$P < 0.05$,
**$P < 0.01$

Experimental results indicated that, compound II-85 had obvious hypotensive effects in SD rats anesthetized with urethane (1.25 mg/kg), and blood pressures recovered to those before drug dosing 6 hours later.

In summary, the above results indicated that, in animal experiments in vitro, compound II-85 had obvious relaxing effects of vascular smooth muscle. Compound II-85 had stronger antagonism against a receptor of adrenaline compared to doxazosin, and its $PA_2$ value against PE was 8.62±0.11. The $PA_2$ value was 6.10±0.13 for compound II-85 to resist $CaCl_2$. Compound II-85 had stronger antagonism against 5-$HT_{2A}$ receptor, and its $PA_2$ value against 5-HT was 9.06±0.07. Therefore, compound II-85 can achieve triple effects including obvious $\alpha_1$ receptor resistance, $Ca^{2+}$ channel blockade, and 5-$HT_{2A}$ receptor resistance, thus achieve higher efficacy or less side effects compared to single and combined medication to single target drug. In in vivo bulk testing on rats, compound II-85 showed good hypotensive effects, good oral absorption, mild toxicity, great therapeutic index, and negative marrow micronucleus test.

REFERENCES

1. [Internal Medicine], Ye Rengao, Lu Zaiying, ed. People's Medical Publishing House, version 6, 2007 April.
2. [Pharmacology], Li Rui, ed. People's Medical Publishing House, version 6, 2007 August.
3. Sanders-Bush E, Mayer S E. 5-Hydroxytryptamine (serotonin): Receptor agonists and antagonists. In: Brunton L L. Lazo J S, Parker K L (eds). Goodman & Gilman's The Pharmacological Basis of Therapeutics (11th ed), Philadelphia: The McGraw-Hill Companies, 2006:158
4. Hoyer D, Clarke D E, Fozard J R, et al. Pharmacol Rev, 1994, 46 (2): 158
5. Martin G R. 5-Hydroxytryptamine receptors. In: The IUPHAR Committee on Receptor Nomenclature and Drug Classification (ed), The IUPHAR Compendium of Receptor Characterization and Classification-, London: IUPHAR Media, 1998: p 167.

The invention claimed is:

1. A method of mediating vasodilation in a subject in need thereof, said method comprising administering to said subject a pharmaceutical composition effective for mediating said vasodilation, said pharmaceutical composition comprising a compound of formula (I) or a pharmaceutically acceptable salt thereof:

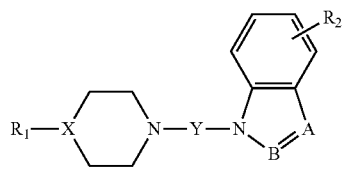

(I)

wherein:

$R_1$ represents an aromatic group or an alicyclic group, each of which is mono- or polysubstituted with $R_3$, wherein, $R_3$ represents H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms;

when $R_3$ are groups for polysubstitution, each $R_3$ is independently selected from the group consisting of H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms;

A, B and X each independently represents CH or N;

$R_2$ represents H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms;

when $R_2$ are groups for polysubstitution group, each $R_2$ is independently selected from the group consisting of H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms; and Y represents a saturated or unsaturated, straight or branched, $C_{1-8}$ hydrocarbon chain optionally substituted with one or more halogen atoms, in which one or more carbon atoms are optionally replaced with heteroatom(s) selected from oxygen, sulfur, and nitrogen.

2. The method of claim 1, wherein the pharmaceutically acceptable salt is hydrochloride salt, hydrobromide salt, sulphate salt, trifluoroacetate salt, mesylate salt, tartrate salt, malate salt, succinate salt, maleate, citrate salt, phosphate salt, lactate salt, pyruvate salt, acetate salt, fumarate salt, oxaloacetate salt, esylate salt, oxalate salt, besylate salt or isethionate salt.

3. The method of claim 1, wherein the aromatic group is phenyl, naphthyl, a benzo-fused five-membered or six-membered heterocyclic ring containing heteroatom(s) selected from N, S and O, or a five-membered or six-membered unsaturated heterocyclic ring.

4. The method of claim 1, wherein $R_3$ is H, halogen, CN, $C_1$-$C_6$ alkyl, $C_1$-$C_6$ alkoxyl, CHO, CO($C_1$-$C_6$ alkyl), COO($C_1$-$C_6$ alkyl) or COOH, each of which alkyl moiety is optionally substituted with one or more halogen atoms.

5. The method of claim 1, wherein $R_2$ is H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH or $NO_2$, each of which alkyl moiety is optionally substituted with one or more halogen atoms.

6. The method of claim 1, wherein Y is an unsubstituted saturated $C_{1-8}$ hydrocarbon group, or an unsubstituted saturated $C_{1-8}$ hydrocarbon group in which one carbon atom is replaced with oxygen or sulfur.

7. The method of claim 1, wherein both A and B represent N.

8. The method of claim 1, wherein
$R_1$ is an aromatic group mono- or disubstituted with $R_3$, wherein
the aromatic group is phenyl, benzisoxazolyl or benzisothiazolyl group;
$R_3$ is H, F, Cl, Br, $OCH_3$ or $CF_3$;
A, B and X each independently represents CH or N;
$R_2$ represents H, F, Cl, Br, CN, $CH_3$ or $OCH_3$; and
Y represents ethylidene, propylidene, butylidene, or ethylideneoxy.

9. The method of claim 1, wherein the compound comprises:

I-1 1-(4-(4-(3-chlorophenyl)piperazin-1-yl)butyl)-1H-benzimidazole,
I-2 1-(4-(4-(3-trifluoromethylphenyl)piperazin-1-yl)butyl)-1H-benzimidazole,
I-3 1-(4-(4-(2,3-dichlorophenyl)piperazin-1-yl)butyl)-1H-benzimidazole,
I-4 1-(4-(4-(2-methoxyphenyl)piperazin-1-yl)butyl)-1H-benzimidazole,
I-5 2-methyl-1-(4-(4-(3-trifluoromethylphenyl)piperazin-1-yl)butyl)-1H-benzimidazole,
I-6 6-fluoro-1-(4-(4-(3-trifluoromethylphenyl)piperazin-1-yl)butyl)-1H-benzimidazole,
I-7 1-(3-(4-phenylpiperazin-1-yl)propyl)-1H-benzimidazole,
I-8 1-(3-(4-(3-fluorophenyl)piperazin-1-yl)propyl)-1H-benzimidazole,
I-9 2-methyl-1-(3-(4-(3-fluorophenyl)piperazin-1-yl)propyl)-1H-benzimidazole,
I-10 1-(4-(4-(3-cyanophenyl)piperazin-1-yl)butyl)-1H-benzimidazole,
I-11 1-(4-(4-(4-methylphenyl)piperazin-1-yl)butyl)-1H-benzimidazole,
I-12 1-(4-(4-(2-furyl)piperazin-1-yl)butyl)-1H-benzimidazole,
I-13 1-(4-(4-(4-pyridyl)piperazin-1-yl)butyl)-1H-benzimidazole,
I-14 1-(4-(4-(2-pyrimidinyl)piperazin-1-yl)butyl)-1H-benzimidazole,
I-15 1-(4-(4-(1-cyclohexyl)piperazin-1-yl)butyl)-1H-benzimidazole,
I-16 1-(4-(4-(1-naphthyl)piperazin-1-yl)butyl)-1H-benzimidazole,
I-17 1-(4-(4-(2-quinoxalinyl)piperazin-1-yl)butyl)-1H-benzimidazole,
I-18 1-(4-(4-(3-(6-fluorobenzisoxazolyl))piperazin-1-yl)butyl)-1H-benzimidazole,
I-19 1-(4-(4-(3-(6-fluorobenzisothiazolyl))piperazin-1-yl)butyl)-1H-benzimidazole,
I-20 1-(4-(4-(3-benzimidazol)piperazin-1-yl)butyl)-1H-benzimidazole,
I-21 1-(4-(4-(3-(6-fluorobenzofuryl))piperazin-1-yl)butyl)-1H-benzimidazole,
I-22 1-(3-(4-(3-(6-fluorobenzisoxazolyl))piperazin-1-yl)propoxyl)-1H-benzimidazole,
I-23 1-(4-(4-(3-trifluoromethylphenyl)piperazin-1-yl)propoxyl)-1H-benzimidazole,
I-24 1-(4-(4-(3-chlorphenyl)piperazin-1-yl)propoxyl)-1H-benzimidazole,
I-25 6-chloro-1-(4-(4-(3-trifluoromethylphenyl)piperazin-1-yl)butyl)-1H-benzimidazole,
I-26 6-cyano-1-(4-(4-(3-trifluoromethylphenyl)piperazin-1-yl)butyl)-1H-benzimidazole,
I-27 6-methoxycarbonyl-1-(4-(4-(3-trifluoromethylphenyl)piperazin-1-yl)butyl)-1H-benzimidazole,
I-28 2-chloro-1-(5-(4-(3-trifluoromethylphenyl)piperazin-1-yl)pentyl)-1H-benzimidazole,
I-29 1-(4-(4-(3-chlorophenyl)piperazin-1-yl)butyl)-1H-benzotriazole,
I-30 1-(4-(4-(3-fluorophenyl)piperazin-1-yl)butyl)-1H-benzotriazole,
I-31 1-(4-(4-(3-trifluoromethylphenyl)piperazin-1-yl)butyl)-1H-benzotriazole,
I-32 6-fluoro-1-(4-(4-(3-trifluoromethylphenyl)piperazin-1-yl)butyl)-1H-benzotriazole,
I-33 5,6-dimethyl-1-(4-(4-(3-trifluoromethylphenyl)piperazin-1-yl)butyl)-1H-benzotriazole,
I-34 3-(4-(4-(1H-benzotriazol-1-yl)butyl)piperazin-1-yl)benzisothiazole,
I-35 3-(4-(4-(1H-benzotriazol-1-yl)butyl)piperazin-1-yl)benzisoxazole,
I-36 6-fluoro-3-(4-(4-(1H-benzotriazol-1-yl)butyl)piperazin-1-yl)benzisoxazole,
I-37 6-fluoro-3-(4-(3-(1H-benzotriazol-1-yl)propyl)piperazin-1-yl)benzisoxazole,
I-38 1-(3-(4-(2,3-dichlorophenyl)piperazin-1-yl)propyl)-1H-benzotriazole,
I-39 1-(3-(4-(3-methylphenyl)piperazin-1-yl)propyl)-1H-benzotriazole,
I-40 1-(4-(4-(3-methoxyphenyl)piperazin-1-yl)butyl)-1H-benzotriazole,
I-41 1-(4-(4-(3-cyanophenyl)piperazin-1-yl)butyl)-1H-benzotriazole,
I-42 1-(5-(4-(3-trifluoromethylphenyl)piperazin-1-yl)pentyl)-1H-benzotriazole,
I-43 1-(4-(4-(2-furyl)piperazin-1-yl)butyl)-1H-benzotriazole,
I-44 1-(4-(4-(4-pyridyl)piperazin-1-yl)butyl)-1H-benzotriazole,
I-45 1-(4-(4-(2-pyrimidinyl)piperazin-1-yl)butyl)-1H-benzotriazole,
I-46 1-(4-(4-cyclohexylpiperazin-1-yl)butyl)-1H-benzotriazole,
I-47 1-(4-(4-(1-naphthyl)piperazin-1-yl)butyl)-1H-benzotriazole,
I-48 1-(4-(4-(2-quinoxalinyl)piperazin-1-yl)butyl)-1H-benzotriazole,
I-49 1-(4-(4-(3-(6-fluoro-benzisothiazolyl))piperazin-1-yl)butyl)-1H-benzotriazole,
I-50 1-(4-(4-(3-benzimidazolyl)piperazin-1-yl)butyl)-1H-benzotriazole,
I-51 1-(3-(4-(3-(6-fluoro-benzofuryl))piperazin-1-yl)propyl)-1H-benzotriazole,
I-52 1-(4-(4-(3-(6-fluoro-benzisoxazolyl))piperazin-1-yl)propoxyl)-1H-benzotriazole,
I-53 6-fluoro-1-(4-(4-(3-(6-fluoro-benzisothiazolyl))piperazin-1-yl) propoxyl)-1H-benzotriazole,
I-54 6-chloro-1-(4-(4-(3-trifluoromethylphenyl)piperazin-1-yl)butyl)-1H-benzotriazole,
I-55 6-cyano-1-(4-(4-(3-trifluoromethylphenyl)piperazin-1-yl)butyl)-1H-benzotriazole,
I-56 6-methoxycarbonyl-1-(4-(4-(3-trifluoromethylphenyl)piperazin-1-yl)butyl)-1H-benzotriazole,
I-57 1-(4-(4-(3-trifluoromethylphenyl)piperazin-1-yl)butyl)-1H-indole,
I-58 6-cyano-1-(4-(4-(3-chlorophenyl)piperazin-1-yl)butyl)-1H-indole,
I-59 1-(3-(4-(3-trifluoromethylphenyl)piperazin-1-yl)propyl)-1H-benzopyrazole,
I-60 6-cyano-1-(3-(4-(2,3-difluorophenyl)piperazin-1-yl) propyl)-1H-benzopyrazole,
I-61 1-[4-(4-(4-fluoro)phenyl)piperazine]butyl-1H-indole,
I-62 1-[4-cyclohexylpiperazine]butyl-1H-indole,
I-63 1-[4-(4-(4-fluoro)phenyl)piperazine]butyl-5-acetyl-1H-indole,
I-64 1-[4-cyclohexylpiperazine]butyl-5-acetyl-1H-indole,
I-65 1-[3-(4-(2,4-difluoro)phenyl)piperazine]butyl-5-acetyl-1H-indole,
I-66 1-[3-(4-(4-methyl)phenyl)piperazine]propyl-1H-indole, I-67 1-[4-(4-(4-chloro)phenyl)piperazine]butyl-1H-indole,
I-68 1-[4-(4-(2-methyl)phenyl)piperazine]butyl-1H-indole,
I-69 1-[4-(4-(3-trifluoromethyl)phenyl)piperazine]butyl-1H-indole,
I-70 1-[3-(4-(4-methyl)phenyl)piperazine]propyl-5-methoxyl-1H-indole,
I-71 1-[4-(4-(4-trifluoromethoxyl)phenyl)piperazine]butyl-5-methoxyl-1H-indole,
I-72 1-[4-(4-(3-trifluoromethyl)phenyl)piperazine]butyl-5-methoxyl-1H-indole,
I-73 1-[3-(4-(2-methyl)phenyl)piperazine]butyl-5-methoxyl-1H-indole,
I-74 1-[3-(4-(2,4-difluoro)phenyl)piperazine]propyl-5-nitro-1H-indole,
I-75 1-[4-(4-(4-chloro)phenyl)piperazine]butyl-5-nitro-1H-indole,
I-76 1-[4-(4-(3-trifluoromethyl)phenyl)piperazine]butyl-5-nitro-1H-indole,
I-77 1-[4-(4-(2-methoxyl)phenyl)piperazine]butyl-5-nitro-1H-indole,
I-78 1-[4-(4-(2-methoxyl)phenyl)piperazine]butyl-5-chloro-1H-indole,
I-79 1-[4-(4-(3-trifluoromethyl)phenyl)piperazine]butyl-5-chloro-1H-indole,
I-80 1-[4-(4-(2,4-difluoro)phenyl)piperazine]butyl-5-chloro-1H-indole,
I-81 1-[2-(4-(2,4-di-trifluoromethoxyl)phenyl)piperazine]ethyl-5-chloro-1H-indole,
I-82 1-[2-(4-(2,4-dimethoxyl)phenyl)piperazine]ethyl-6-nitro-1H-indole,
I-83 1-[2-(4-(2,4-dichloro)phenyl)piperazine]ethyl-6-methoxyl-1H-indole,
I-84 N-(3-(1H-benzotriazol-1-yl)propyl)-4-(3-benzisoxazolyl)piperidine,
I-85 N-(3-(1H-benzotriazol-1-yl)propyl)4-(3-(6-fluorobenzisoxazolyl))piperidine,
I-86 N-(3-(1H-benzotriazol-1-yl)propyl)-4-(3-(6-methoxylbenzisoxazolyl))piperidine,
I-87 N-(3-(1H-benzotriazol-1-yl)propyl)-4-(3-(6-methoxylbenzisoxazolyl))piperidine,
I-88 N-(3-(6-fluoro-1H-benzotriazol-1-yl)propyl)-4-(3-(6-fluorobenzisoxazolyl))piperidine,
I-89 N-(3-(6-chloro-1H-benzotriazol-1-yl)propyl)-4-(3-(6-fluorobenzisoxazolyl))piperidine,
I-90 N-(3-(6-methyl-1H-benzotriazol-1-yl)propyl)-4-(3-(6-fluorobenzisoxazolyl))piperidine,
I-91 N-(3-(6-methoxyl-1H-benzotriazol-1-yl)propyl)-4-(3-(6-fluorobenzisoxazolyl))piperidine,
I-92 N-(3-(6-formyl-1H-benzotriazol-1-yl)propyl)-4-(3-(6-fluorobenzisoxazolyl))piperidine,
I-93 N-(3-(6-methoxylbenzotriazolyl)propyl)-4-(3-benzisoxazolyl)piperidine,
I-94 N-(2-(1-benzotriazolyl)ethyl)-4-(3-(6-fluorobenzisoxazolyl))piperidine,
I-95 N-(4-(1-benzotriazolyl)butyl)-4-(3-(6-fluorobenzisoxazolyl))piperidine,
I-96 N-(4-(6-cyanobenzotriazolyl)butyl)-4-(3-(6-fluorobenzisoxazolyl))piperidine,
I-97 N-(4-(6-cyanobenzotriazolyl)butyl)-4-(3-(6-methoxylbenzisoxazolyl))piperidine,
I-98 N-(2-(6-methoxylbenzotriazolyl)ethoxyl)-4-(3-(6-fluorobenzisoxazolyl))piperidine,
I-99 N-(2-(1-benzotriazolyl)ethoxyl)-4-(3-(6-fluorobenzisoxazolyl))piperidine,
I-100 N-(3-(6-methoxylbenzotriazolyl)propyl)-4-(3-benzisothiazolyl)piperidine,
I-101 N-(3-(6-methoxylbenzotriazolyl)propyl)-4-(3-benzopyrazol)piperidine,
I-102 N-(3-(6-methoxylbenzotriazolyl)propyl)-4-(3-benzofuryl)piperidine,
I-103 N-(3-(1-benzopyrazol)propyl)-4-(3-(6-fluorobenzisoxazolyl))piperidine,
I-104 N-(4-(6-cyanobenzopyrazolyl)butyl)-4-(3-(6-fluorobenzisoxazolyl))piperidine,
I-105 N-(2-(6-fluorobenzotriazolyl)ethoxyl)-4-(3-(6-fluorobenzisoxazolyl))piperidine,
I-106 N-(3-(6-fluorobenzotriazolyl)propoxyl)-4-(3-(6-fluorobenzisoxazolyl))piperidine,
I-107 N-(4-(1H-benzimidazol-1-yl)butyl)-4-(3-chlorophenyl)piperidine,
I-108 N-(4-(1H-benzotriazol-1-yl)butyl)-4-(3-chlorophenyl)piperidine,
I-109 N-(4-(1H-benzimidazol-1-yl)butyl)-4-(3-trifluoromethylphenyl)piperidine,
I-110 N-(4-(1H-benzotriazol-1-yl)butyl)-4-(3-trifluoromethylphenyl)piperidine,
I-111 N-(4-(1H-benzimidazol-1-yl)butyl)-4-(3-fluorophenyl)piperidine,
I-112 N-(4-(1H-benzimidazol-1-yl)butyl)-4-(2-methoxylphenyl)piperidine,
I-113 N-(4-(6-fluoro-1H-benzotriazol-1-yl)butyl)-4-(3-trifluoromethylphenyl)piperidine,
I-114 N-(4-(6-methoxyl-1H-benzotriazol-1-yl)butyl)-4-(3-trifluoromethylphenyl)piperidine,
I-115 N-(4-(6-cyano-1H-benzotriazol-1-yl)butyl)-4-(3-trifluoromethylphenyl)piperidine,
I-116 N-(4-(1H-benzotriazol-1-yl)propoxyl)-4-(3-trifluoromethylphenyl)piperidine,
I-117 N-(4-(1H-benzimidazol-1-yl)propoxyl)-4-(3-trifluoromethylphenyl)piperidine,
I-118 N-(4-(1H-benzimidazol-1-yl)butyl)-4-(2-furyl)piperidine,
I-119 N-(4-(1H-benzimidazol-1-yl)butyl)-4-(4-pyridyl)piperidine,
I-120 N-(4-(1H-benzimidazol-1-yl)butyl)-4-(2-pyrimidinyl)piperidine,
I-121 N-(4-(1H-benzimidazol-1-yl)butyl)-4-(4-cyclohexyl)piperidine,
I-122 N-(4-(1H-benzimidazol-1-yl)butyl)-4-(1-naphthyl)piperidine,
I-123 N-(4-(1H-benzimidazol-1-yl)butyl)-4-(2-quinoxalinyl)piperidine,
I-124 N-(4-(1H-benzimidazol-1-yl)butyl)-4-(3-chlorophenyl)piperidine,
I-125 N-(4-(1H-benzotriazol-1-yl)butyl)-4-(3-chlorophenyl)piperidine,
I-126 N-(4-(1H-benzimidazol-1-yl)butyl)-4-(3 trifluoromethylphenyl)piperidine,
I-127 N-(4-(1H-benzotriazol-1-yl)butyl)-4-(3-trifluoromethylphenyl)piperidine,
I-128 N-(4-(1H-benzimidazol-1-yl)butyl)-4-(3-fluorophenyl)piperidine,
I-129 N-(4-(1H-benzimidazol-1-yl)butyl)-4-(2-methoxylphenyl)piperidine,
I-130 N-(4-(6-fluoro-1H-benzotriazol-1-yl)butyl)-4-(3-trifluoromethylphenyl)piperidine,
I-131 N-(4-(6-methoxyl-1H-benzotriazol-1-yl)butyl)-4-(3-trifluoromethylphenyl)piperidine,
I-132 N-(4-(6-cyano-1H-benzotriazol-1-yl)butyl)-4-(3-trifluoromethylphenyl)piperidine, I-133 N-(4-(1H-benzotriazol-1-yl)propoxyl)-4-(3-trifluoromethylphenyl)piperidine,
I-134 N-(4-(1H-benzimidazol-1-yl)propoxyl)-4-(3-trifluoromethylphenyl)piperidine,
I-135 N-(3-(1H-benzotriazol-1-yl)propyl)-4-(3-(6-methylbenzisoxazolyl))piperidine,
I-136 N-(3-(1H-benzotriazol-1-yl)propyl)-4-(3-(6-methoxylbenzisoxazolyl))piperidine,
I-137 N-(3-(6-fluoro-1H-benzotriazol-1-yl)propyl)-4-(3-(6-fluorobenzisoxazolyl))piperidine,
I-138 N-(3-(6-chloro-1H-benzotriazol-1-yl)propyl)-4-(3-(6-fluorobenzisoxazolyl))piperidine,
I-139 N-(3-(6-methyl-1H-benzotriazol-1-yl)propyl)-4-(3-(6-fluorobenzisoxazolyl))piperidine,
I-140 N-(3-(6-methoxyl-1H-benzotriazol-1-yl)propyl)-4-(3-(6-fluorobenzisoxazolyl))piperidine,
I-141 N-(3-(6-formyl-1H-benzotriazol-1-yl)propyl)-4-(3-(6-fluorobenzisoxazolyl))piperidine,
I-142 N-(3-(6-methoxybenzotriazolyl)propyl)-4-(3-benzisoxazolyl)piperidine,
I-143 N-(2-(1-benzotriazolypethyl)-4-(3-(6-fluorobenzisoxazolyl))piperidine,
I-144 N-(4-(1-benzotriazolyl)butyl)-4-(3-(6-fluorobenzisoxazolyl))piperidine,
I-145 N-(4-(6-cyanobenzotriazolyl)butyl)-4-(3-(6-fluorobenzisoxazolyl))piperidine,
I-146 N-(4-(6-cyanobenzotriazolyl)butyl)-4-(3-(6-methoxylbenzisoxazolyl))piperidine,
I-147 N-(2-(6-methoxybenzotriazolyl)ethoxyl)-4-(3-benzisoxazolyl)piperidine,
I-148 N-(2-(1-benzotriazolyl)ethoxyl)-4-(3-fluorobenzisoxazolyl)piperidine,
I-149 N-(3-(6-methoxybenzotriazolyl)propyl)-4-(3-(6-fluorobenzisothiazolyl))piperidine,
I-150 N-(3-(6-methoxybenzotriazolyl)propyl)-4-(3-(6-fluorobenzopyrazol))piperidine,
I-151 N-(3-(6-methoxybenzotriazolyl)propyl)-4-(3-(6-fluorobenzofuranyl))piperidine,
I-152 N-(4-(1H-benzimidazol-1-yl)butyl)-4-(2-furyl)piperidine,
I-153 N-(4-(1H-benzimidazol-1-yl)butyl)-4-(4-pyridyl)piperidine,
I-154 N-(4-(1H-benzimidazol-1-yl)butyl)-4-(2-pyrimidinyl)piperidine,
I-155 N-(4-(1H-benzotriazol-1-yl)butyl)-4-cyclohexylpiperidine,
I-156 N-(4-(1H-benzotriazol-1-yl)butyl)-4-(1-naphthyl)piperidine, or
I-157 N-(4-(1H-benzotriazol-1-yl)butyl)-4-(2-quinoxalinyl)piperidine.

10. The method of claim 1, wherein the pharmaceutical composition is administered for treatment of hypertension, heart failure, angina pectoris, coronary heart disease, cerebral ischemic disease induced by vascular spasm, myocardial ischemic disease, shock, renal ischemia, renal dysfunction due to renal vascular spasm, or peripheral vascular spasmodic disease.

11. The method of claim 2, wherein the pharmaceutically acceptable salt contains crystal water.

12. The method of claim 2, wherein the pharmaceutically acceptable salt is hydrochloride salt, hydrobromide salt, sulfate salt or mesylate salt.

13. The method of claim 3, wherein the aromatic group is phenyl, naphthyl, benzothiazolyl, benzisothiazolyl, benzoxazolyl, benzisoxazolyl, benzimidazoyl, benzopyrazol, benzofuryl, benzopyrimidinyl, benzopyridyl, quinoxalinyl, furyl, pyridyl or pyrimidinyl group.

14. The method of claim 3, wherein the aromatic group is phenyl or benzisoxazolyl group, wherein (i) the aromatic group is phenyl, and X is N, or (ii) the aromatic group is benzisoxazolyl, X is CH, and A is N.

15. The method of claim 1, wherein the alicyclic group is cyclopentyl, cyclohexyl, tetrahydrofuryl, piperidyl or piperazinyl group.

16. The method of claim 4, wherein (i) X is N, and $R_3$ is H, F, Cl, or $OCH_3$, or (ii) X is CH, and $R_3$ is H, F, or $CF_3$.

17. The method of claim 5, wherein (i) X is N, and $R_2$ is H, F Cl, CN, $CH_3$ or $COOCH_3$, or (ii) X is CH, and $R_2$ is H or $OCH_3$.

18. The method of claim 6, wherein (i) Y is butylidene, and X is N, or (ii) Y is propylidene, and X is CH.

19. A method of inducing in a subject in need thereof, relaxation of vascular smooth muscle, said method comprising administering to the subject a pharmaceutical composition effective for such relaxation, said pharmaceutical composition comprising a compound of formula (I) or a pharmaceutically acceptable salt thereof:

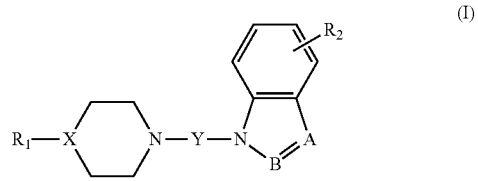

wherein:
$R_1$ represents an aromatic group or an alicyclic group, each of which is mono- or polysubstituted with $R_3$, wherein, $R_3$ represents H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms; when $R_3$ are groups for polysubstitution, each $R_3$ is independently selected from the group consisting of H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O) ($C_1$-$C_6$ alkyl), —S(O)$_2$H or —S(O)$_2$($C_1$-$C_6$ alkyl), each of which alkyl moiety is optionally substituted with one or more halogen atoms;

A, B and X each independently represents CH or N;
$R_2$ represents H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms; when $R_2$ are groups for polysubstitution group, each $R_2$ is independently selected from the group consisting of H, halogen, CN, $C_1$-$C_6$ alkyl, $C_1$-$C_6$ alkoxyl, CHO, CO($C_1$-$C_6$ alkyl), COO($C_1$-$C_6$ alkyl), COOH, $NO_2$, $NH_2$, NH($C_1$-$C_6$ alkyl), N($C_1$-$C_6$ alkyl)$_2$, SH, S($C_1$-$C_6$ alkyl), —S(O)($C_1$-$C_6$ alkyl), —S(O)$_2$H or —S(O)$_2$($C_1$-$C_6$ alkyl), each of which alkyl moiety is optionally substituted with one or more halogen atoms; and Y represents a saturated or unsaturated, straight or branched, $C_{1-8}$ hydrocarbon chain optionally substituted with one or more halogen atoms, in which one or more carbon atoms are optionally replaced with heteroatom(s) selected from oxygen, sulfur, and nitrogen,
wherein the compound of formula (I) or a pharmaceutically acceptable salt thereof is at least one of an $\alpha_1$ receptor antagonist, a $Ca^{2+}$ channel blocker, and a $5\text{-}HT_{2A}$ receptor antagonist.

* * * * *